(12) United States Patent
Chiu et al.

(10) Patent No.: US 8,969,594 B2
(45) Date of Patent: Mar. 3, 2015

(54) FULLERENE-CONTAINING HEMICARCEPLEXES AND A METHOD OF PURIFYING FULLERENES BY USING THE SAME

(71) Applicant: National Taiwan University, Taipei (TW)

(72) Inventors: Sheng-Hsien Chiu, Taipei (TW); Ming-Jhe Li, Hualien County (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 14/197,284

(22) Filed: Mar. 5, 2014

(65) Prior Publication Data

US 2014/0187800 A1     Jul. 3, 2014

Related U.S. Application Data

(63) Continuation-in-part of application No. 13/653,539, filed on Oct. 17, 2012, now abandoned.

(51) Int. Cl.
    *C07D 321/00*     (2006.01)
    *C07D 323/00*     (2006.01)
    *C01B 31/04*     (2006.01)

(52) U.S. Cl.
    CPC ............... *C07D 323/00* (2013.01); *C01B 31/04* (2013.01)
    USPC ........................................................ 549/348

(58) Field of Classification Search
    USPC ........................................................ 549/348
    See application file for complete search history.

(56) References Cited

U.S. PATENT DOCUMENTS 5,711,927 A     1/1998     Atwood et al.
7,771,691 B2     8/2010     Mendoza et al.

FOREIGN PATENT DOCUMENTS

AU     2120695     10/1995
CA     2185443 C     9/1995
WO     9525067     9/1995

OTHER PUBLICATIONS

Li et al., "Hemicarceplex Formation With a Cyclotriveratrylene-Based Molecular Cage Allows Isolation of High-Purity (•99.0%) C70 Directly from Fullerene Extracts." Organic Letters (2012), vol. 14, No. 24, p. 6146-6149.

*Primary Examiner* — Nizal Chandrakumar
(74) *Attorney, Agent, or Firm* — McClure, Qualey & Rodack, LLP

(57) ABSTRACT

Fullerene⊙CTV complexes, comprising fullerene⊙CTV hemicarceplexes, formed by various cyclotriveratrylene (CTV)-based molecular cages and various fullerene guests are disclosed. A method of direct isolating at least a fullerene from fullerene mixtures by using the above fullerene CTV hemicarceplexes but without using crystallization or HPLC is also disclosed.

2 Claims, 25 Drawing Sheets

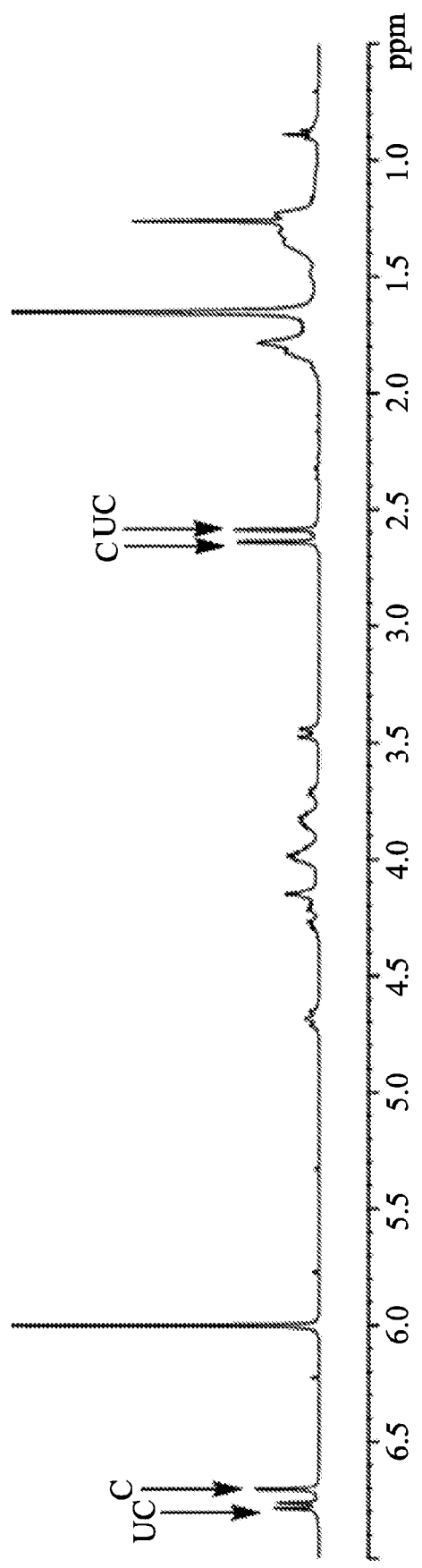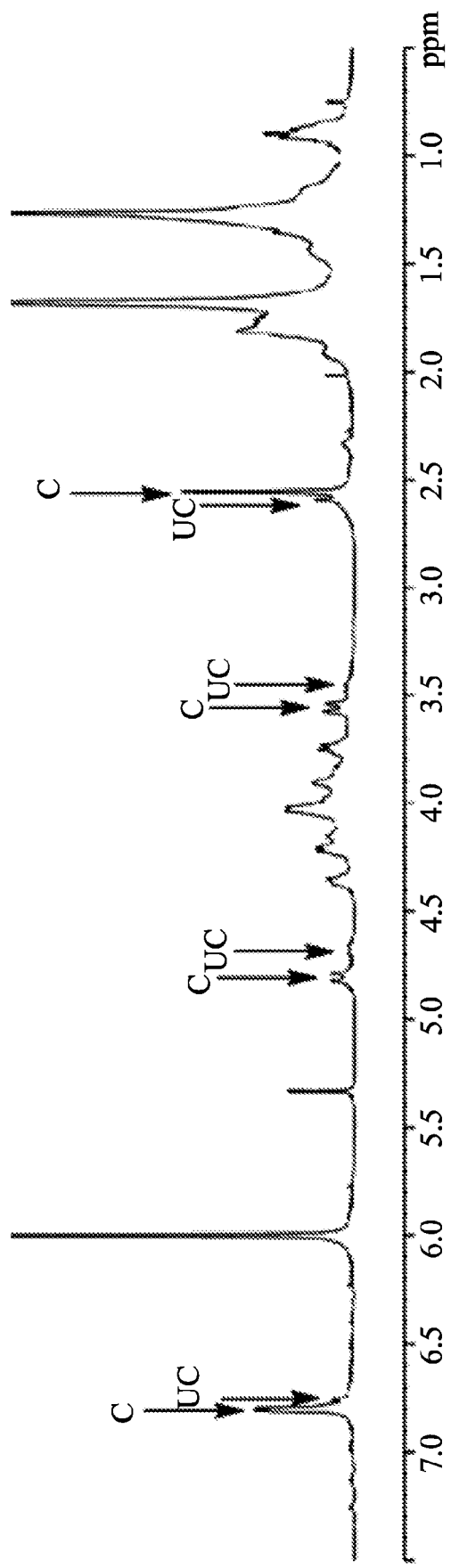
FIG. 18A
FIG. 18B

FULLERENE-CONTAINING HEMICARCEPLEXES AND A METHOD OF PURIFYING FULLERENES BY USING THE SAME

CROSS-REFERENCE TO RELATED APPLICATION

This application is a continuation-in-part of U.S. application Ser. No. 13/653,539, filed Oct. 17, 2012, the full disclosure of which is incorporated herein by reference.

BACKGROUND

1. Technical Field

The disclosure relates to several fullerene-containing hemicarceplexes and a method of purifying fullerenes by using the same.

2. Description of Related Art

Because of their versatile configurations and attractive properties, fullerenes, including cylindrical carbon nanotubes (CNTs) and spherical and spheroidal buckyballs, have found applications in a wide range of fields, including materials science, chemistry, super- and semi-conducting physics, and biology. Ignoring CNTs, which lack uniform diameters or lengths, the most abundant structurally distinct species in a typical fullerene extract are two buckyballs, i.e. $C_{60}$ and $C_{70}$. Even though they have been investigated widely since their discovery in the 1980s, the practical applications of buckyballs have been limited by their poor solubilities in organic solvents; this characteristic has also seriously complicated their isolation and purification.

Several elegant methods have been developed for the isolation of the more-abundant $C_{60}$ from fullerene extracts; in contrast, isolating the lower-in-symmetry and photovoltaically-more-interesting $C_{70}$ in high purity from the same mixtures has been less straightforward. Indeed, tedious purification involving crystallization and/or high-performance liquid chromatography (HPLC) is frequently required to obtain high-purity $C_{70}$, making it much less affordable than $C_{60}$ of the same quality; accordingly, relatively limited research has been undertaken to discover and expand the practical applications of $C_{70}$.

One attractive approach for the selective isolation of $C_{70}$ involves exploiting its host-guest complexation behavior. Although a few judiciously designed synthetic host molecules do form complexes with $C_{60}$ and $C_{70}$ in solution, using such host-guest complexes as a means of separating mixtures of buckyballs (i.e., with high degrees of selectivity and stability) remains a challenge.

Unlike carcerands, which cannot release their entrapped guests, hemicarcerands allow sequestration of complementary guests (forming room temperature-isolatable hemicarceplexes) as well as their release at elevated temperatures. Although Cram first proposed, in 1995, that the internal space of a cavitand dimer might be a suitable host for $C_{60}$ (Hemicarcerands with interiors potentially capable of binding large guests. *J. Chem. Soc., Chem. Commun.* 1085-1087 (1995)), hemicarcerands that can selectively imprison guests as big as $C_{60}$ and $C_{70}$ have never been realized previously, presumably because of difficulties in balancing the steric sizes and free energies of complexation of the host and guest components to allow selective sequestration and release of the guests.

SUMMARY

In one aspect, the present invention is directed to a fullerene⊙CTV complex, comprising a hemicarceplex, formed by trapping a fullerene guest or a derivative thereof (abbreviated as a guest molecule below) in a cyclotriveratrylene-based molecular cage (abbreviated as CTV below) having a chemical structure below, and LS1 and LS2 are first and second linking spacers respectively having a first chain length and a second chain length, and the first chain length is shorter or equal to the second chain length. The first chain length of the first linking spacers determines an interior space of the CTV cage for accommodating the guest molecule, and the second chain length of the second linking spacers determines an opening size of the CTV cage for entering the guest molecule.

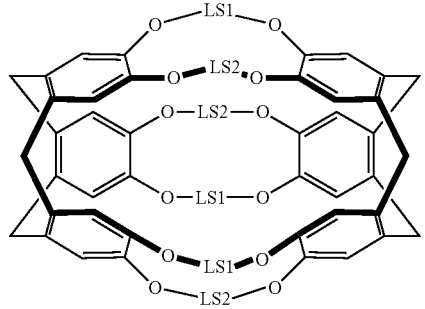

CTV

According to an embodiment, the first linking spacers or the second linking spacers are straight alkyl chains containing at least 10 carbons for accommodating a guest molecule having at least 60 atoms in the CTV.

According to another embodiment, the first linking spacers or the second linking spacers are straight alkyl chains containing 10-15 carbons for accommodating the guest molecule having 60-84 carbons in the CTV.

For example, the cyclotriveratrylene-based molecular cage may be

CTV1
$(LS1 = LS2 = —(CH_2)_{12}—)$,

CTV2
$(LS1 = —(CH_2)_{11}—, LS2 = —(CH_2)_{12}—)$,

CTV3
$(LS1 = —(CH_2)_{10}—, LS2 = —(CH_2)_{12}—)$,

CTV4
$(LS1 = —(CH_2)_{12}—,$
$LS2 = (CH_2)_4—O—\underset{O}{\overset{}{C}}—\underset{H_2}{\overset{}{C}}—\underset{}{\overset{H_2}{C}}—\underset{O}{\overset{}{C}}—O—(CH_2)_4—)$, CTV5
$(LS1 = —(CH_2)_{11}—,$
$LS2 = (CH_2)_4—O—\underset{O}{\overset{}{C}}—\underset{H_2}{\overset{}{C}}—\underset{}{\overset{H_2}{C}}—\underset{O}{\overset{}{C}}—O—(CH_2)_4—)$, CTV6
$(LS1 = —(CH_2)_{10}—,$
$LS2 = (CH_2)_4—O—\underset{O}{\overset{}{C}}—\underset{H_2}{\overset{}{C}}—\underset{}{\overset{H_2}{C}}—\underset{O}{\overset{}{C}}—O—(CH_2)_4—)$,

CTV7
$(LS1 = —(CH_2)_{12}—, LS2 = —(CH_2)_{13}—)$,

CTV8
$(LS1 = —(CH_2)_{12}—, LS2 = —(CH_2)_{14}—)$,

CTV9
$(LS1 = —(CH_2)_{12}—, LS2 = —(CH_2)_{15}—)$,

CTV10
$(LS1 = —(CH_2)_{13}—, LS2 = —(CH_2)_{14}—)$,

-continued $$(LS1 = LS2 = -(CH_2)_{10}-), \text{ or} \quad \text{CTV11}$$

$$(LS1 = -(CH_2)_{10}-, LS2 = -(CH_2)_{11}-). \quad \text{CTV12}$$

According to another embodiment, at least one of the first and the second linking spacers containing a diester linkage. For example, the cyclotriveratrylene-based molecular cage may be

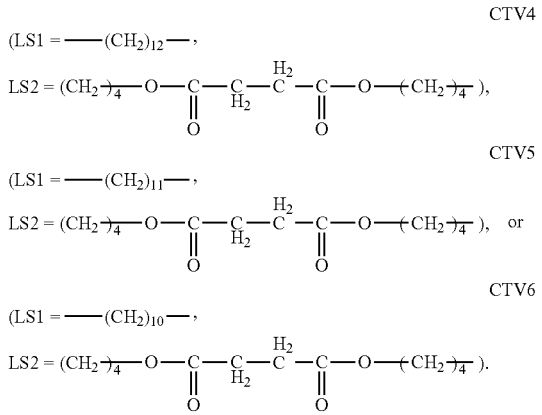

According to yet another embodiment, the complex may be $C_{60}\odot CTV1$, $C_{70}\odot CTV1$, $C_{76}\odot CTV1$, $C_{78}\odot CTV1$, $C_{70}\odot CTV2$, $C_{60}\odot CTV2$, $C_{60}\odot CTV3$, $Sc_3N@C_{80}\odot CTV4$, $C_{60}\odot CTV5$, $C_{70}\odot CTV5$, $C_{76}\odot CTV5$, $C_{78}\odot CTV5$, $C_{60}\odot CTV6$, $C_{70}CTV7$, $C_{76}\odot CTV7$, $C_{78}\odot CTV7$, $C_{82}\odot CTV7$, $C_{84}\odot CTV7$, $C_{86}\odot CTV7$, $C_{70}CTV8$, $C_{76}\odot CTV8$, $C_{78}\odot CTV8$, $C_{82}\odot CTV8$, $C_{84}\odot CTV8$, $C_{86}\odot CTV8$, $C_{70}\odot CTV9$, $C_{60}\odot CTV11$, or $C_{60}\odot CTV12$.

According to yet another embodiment, the complex may be $C_{70}\odot CTV1$, $C_{76}\odot CTV1$, $C_{78}\odot CTV1$, $C_{70}\odot CTV2$, $C_{60}\odot CTV3$, $Sc_3N@C_{80}\odot CTV4$, $C_{76}\odot CTV5$, $C_{78}\odot CTV5$, $C_{70}\odot CTV7$, $C_{76}\odot CTV7$, $C_{78}\odot CTV7$, $C_{82}\odot CTV7$, $C_{84}\odot CTV7$, $C_{86}\odot CTV7$, $C_{70}\odot CTV8$, $C_{76}\odot CTV8$, $C_{78}\odot CTV8$, $C_{82}\odot CTV8$, $C_{84}\odot CTV8$, $C_{86}\odot CTV8$, $C_{60}\odot CTV11$, or $C_{60}\odot CTV12$ when the complex is room temperature isolatable.

In another aspect, the present invention directs to a method of forming a fullerene⊙CTV hemicarceplex. The method comprises the following steps. A fullerene or a derivative thereof, and a cyclotriveratrylene-based molecular cage described above are mixed in a solvent to form a mixture solution. Then, the mixture solution is heated to form a fullerene⊙CTV hemicarceplex.

According to an embodiment, the solvent can majorly contain $CS_2$, $CH_2Cl_2$, $CHCl_3$ or $CHCl_2CHCl_2$, for example.

In yet another aspect, the present invention directs to a method of isolating at least a fullerene by using a fullerene⊙CTV hemicarceplex. The method comprises the following steps. First, a fullerene or a derivative thereof, and a cyclotriveratrylene-based molecular cage described above are mixed in a first solvent to form a mixture solution. Next, the fullerene⊙CTV hemicarceplexe is isolated by column chromatography without using crystallization or high performance liquid chromatography (HPLC). Then, the fullerene⊙CTV hemicarceplexe is dissociated in a second solvent.

According to an embodiment, the first solvent has less tendency than the fullerenes to occupy an inner space of the cyclotriveratrylene-based molecular cage. For example, the first solvent can majorly contain $CS_2$, $CH_2Cl_2$, $CHCl_3$, or $CHCl_2CHCl_2$.

According to another embodiment, the second solvent can dissolve fullerene⊙CTV hemicarceplex and allow its dissociation to release fullerene. For example, the second solvent can majorly contain $CS_2$, $CH_2Cl_2$, $CHCl_3$, $CHCl_2CHCl_2$, benzene, toluene, or dichlorobenzene.

The forgoing presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later. Many of the attendant features will be more readily appreciated as the same becomes better understood by reference to the following detailed description considered in connection with the accompanying drawings.

BRIEF DESCRIPTION OF THE DRAWINGS

FIGS. 18A and 18B are $^1$H NMR (400 MHz, CDCl$_3$, 298 K) spectra of the equimolar mixture of CTV5 to C$_{60}$ and C$_{70}$, respectively.

DETAILED DESCRIPTION

Figure 1A:
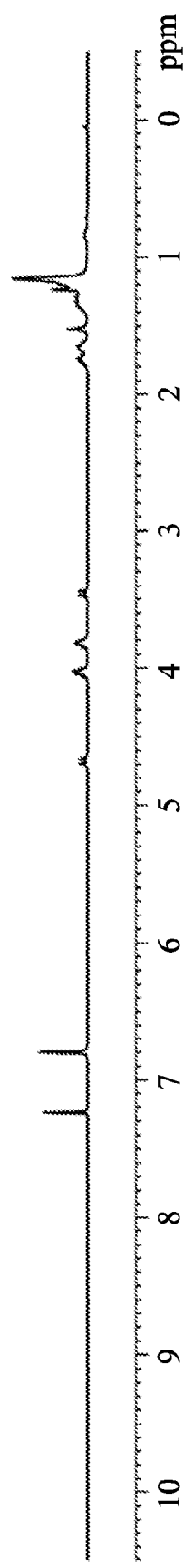
FIGS. 1A and 1B are $^1$H NMR (400 MHz, CDCl$_3$, 298 K) and $^{13}$C NMR (100 MHz, CDCl$_3$, 298 K) spectra of CTV1, respectively.

In the following detailed description, for purposes of explanation, numerous specific details are set forth in order to provide a thorough understanding of the disclosed embodiments. It will be apparent, however, that one or more embodiments may be practiced without these specific details.

Synthesizing Cyclotriveratrylenes (CTVs) for Forming Fullerene CTV Hemicarceplexes Cyclotriveratrylene-based molecular cages (abbreviated as CTVs below) for forming fullerene CTV complexes or hemicarceplexes were synthesized first. The CTV host molecule has a chemical structure shown below, wherein LS1 and LS2 represent first and second linking spacers.

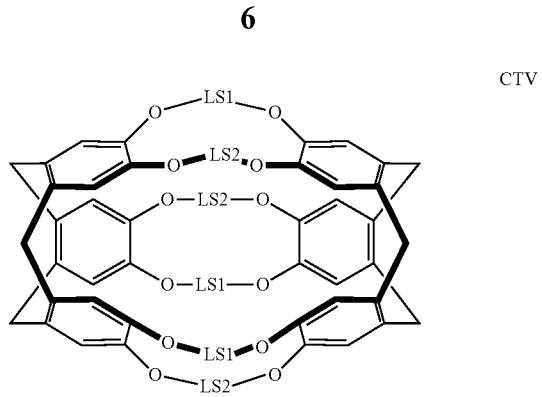

According to an embodiment, at least three of the first and second linking spacers are alkyl chains containing at least 10 carbons, such as 10-15 carbons. According to another embodiment, at least one of the first and second linking spacers containing a diester linkage. Six CTV host molecules were synthesized, and the first and the second linking spacers are listed in the table below. Please note that the first linking spacers LS1 and the second linking spacers LS2 listed below are exchangeable, since it is the chain length of the first and the second linking spacers that are matters about the accommodation of a guest fullerene or a derivative thereof.

| CTV host | LS1 | LS2 |
|---|---|---|
| CTV1 | —(CH$_2$)$_{12}$— | —(CH$_2$)$_{12}$— |
| CTV2 | —(CH$_2$)$_{11}$— | —(CH$_2$)$_{12}$— |
| CTV3 | —(CH$_2$)$_{10}$— | —(CH$_2$)$_{12}$— |
| CTV4 | —(CH$_2$)$_{12}$— | —(CH$_2$)$_4$—O—C(=O)—CH$_2$—C(=O)—O—(CH$_2$)$_4$— |
| CTV5 | —(CH$_2$)$_{11}$— | —(CH$_2$)$_4$—O—C(=O)—CH$_2$—C(=O)—O—(CH$_2$)$_4$— |
| CTV6 | —(CH$_2$)$_{10}$— | —(CH$_2$)$_4$—O—C(=O)—CH$_2$—C(=O)—O—(CH$_2$)$_4$— |
| CTV7 | —(CH$_2$)$_{12}$— | —(CH$_2$)$_{13}$— |
| CTV8 | —(CH$_2$)$_{12}$— | —(CH$_2$)$_{14}$— |
| CTV9 | —(CH$_2$)$_{12}$— | —(CH$_2$)$_{15}$— |
| CTV10 | —(CH$_2$)$_{13}$— | —(CH$_2$)$_{14}$— |
| CTV11 | —(CH$_2$)$_{10}$— | —(CH$_2$)$_{10}$— |
| CTV12 | —(CH$_2$)$_{10}$— | —(CH$_2$)$_{11}$— |

Synthesis of CTV1

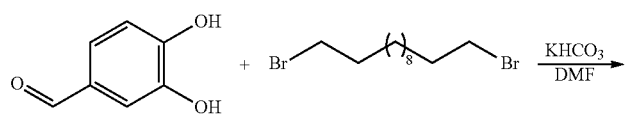

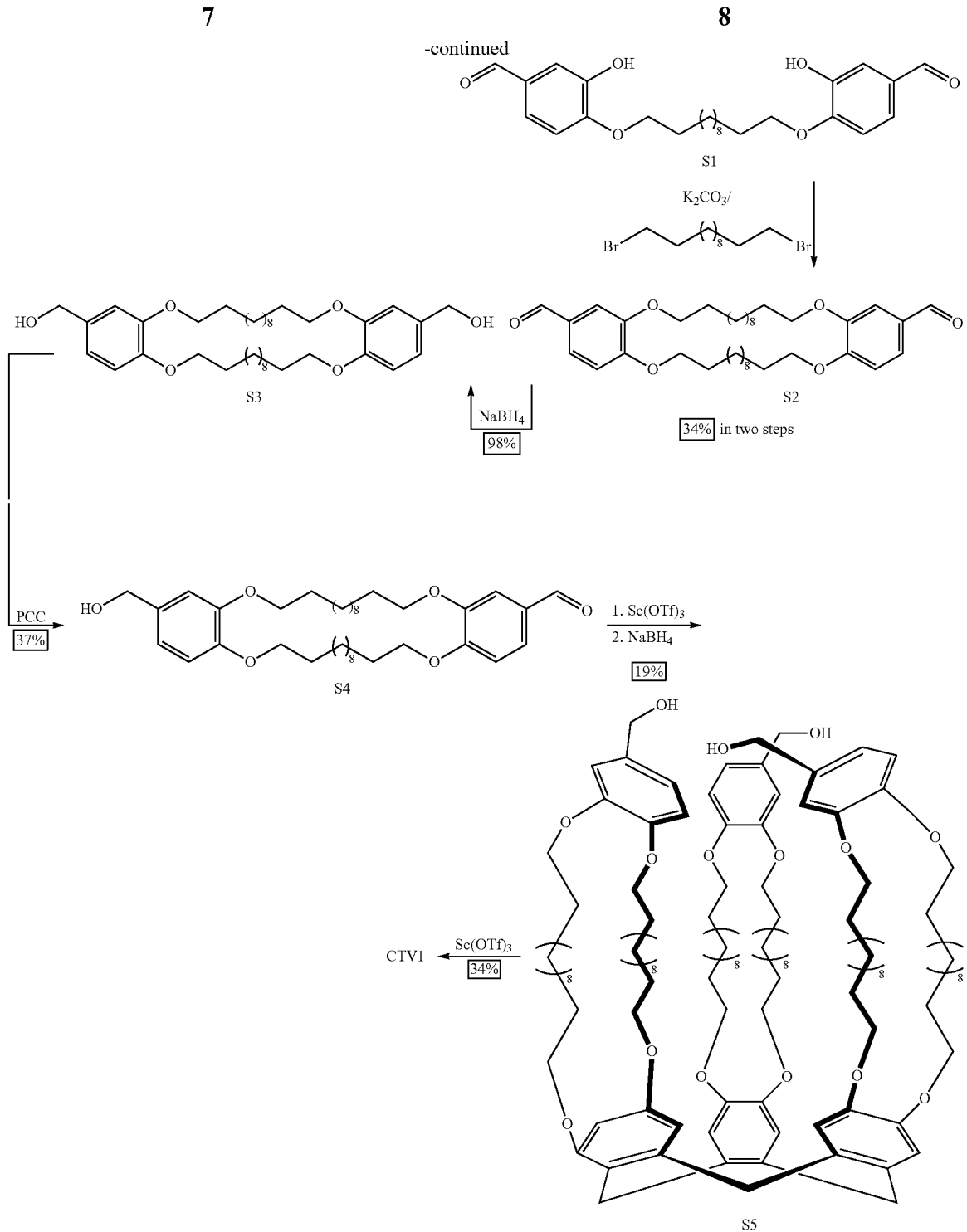

Dialdehyde S2:

The reaction of 3,4-dihydroxybenzaldehyde (5.17 g, 37.4 mmol), 1,12-dibromododecane (5.58 g, 17.0 mmol), and KHCO$_3$ (3.74 g, 37.4 mmol) in DMF (75 mL) at 65° C. for 3 days afforded the monoalkylated-dialdehyde S1, which was dissolved with 1,12-dibromodecane (3.71 g, 11.3 mmol) in DMF (130 mL) and reacted with K$_2$CO$_3$ (9.37 g, 67.8 mmol) in DMF (1 L) to afford a white solid S2 (2.35 g, 34%).

Mp: 175-176° C.; $^1$H NMR (400 MHz, CDCl$_3$, 298 K): δ=1.25-1.39 (m, 24H), 1.45-1.55 (m, 8H), 1.75-1.86 (m, 8H), 4.03 (t, J=5.6 Hz, 4H), 4.06 (t, J=5.6 Hz, 4H), 6.92 (d, J=8 Hz, 2H), 7.37 (d, J=2 Hz, 2H), 7.40 (dd, J=8, 2 Hz, 2H), 9.81 (s, 2H); $^{13}$C NMR (100 MHz, CDCl$_3$, 298 K): δ=26.4, 26.4, 29.2, 29.3, 29.6, 29.6, 29.8, 29.8, 29.8, 29.8, 69.0, 69.1, 111.2, 111.9, 126.6, 129.9, 149.6, 154.9, 191.0; HR-MS (ESI): calcd for C$_{38}$H$_{56}$O$_6$Na$^+$ [M+Na]$^+$, m/z 631.3975. found, m/z 631.3972.

Diol S3:

Following the procedure described above for S2, the reaction of the dialdehyde S2 (1.92 g, 3.16 mmol) and NaBH$_4$ (0.36 g, 9.47 mmol) in isopropyl alcohol (79 mL) and CH$_2$Cl$_2$ (79 mL) under reflux for 16 h afforded a white solid S3 (1.89 g, 98%).

Mp: 153-154° C.; $^1$H NMR (400 MHz, CDCl$_3$, 298 K): δ=1.18-1.38 (m, 24H), 1.43-1.53 (m, 8H), 1.73-1.82 (m, 8H), 3.97 (t, J=6.4 Hz, 4H), 3.98 (t, J=6.4 Hz, 4H), 4.58 (s, 4H), 6.84 (s, 4H), 6.91 (s, 2H); $^{13}$C NMR (100 MHz, CDCl$_3$, 298 K): δ=26.1, 26.3, 26.4, 29.4, 29.5, 29.5, 29.6, 29.7, 29.8, 29.8, 65.4, 69.3, 69.5, 113.2, 114.2, 119.7, 133.8, 149.0, 149.6; HR-MS (ESI): calcd for C$_{38}$H$_{60}$O$_6$Na$^+$ [M+Na]$^+$, m/z 635.4288. found, m/z 635.4285.

Mono-Alcohol S4:

Following the procedure described above for S3, the reaction of the diol S3 (0.1 g, 0.163 mmol), pyridinium chlorochromate (53 mg, 245 μmole), 4-Å molecular sieves (0.75 g), and Celite (1.49 g) in CH$_2$Cl$_2$ (5.2 mL) and DMF (3 mL) at 60° C. for 3 h afforded a white solid S4 (39 mg, 37%).

Mp: 166-168° C.; $^1$H NMR (400 MHz, CDCl$_3$, 298 K): δ=1.25-1.39 (m, 24H), 1.44-1.55 (m, 8H), 1.73-1.86 (m, 8H), 3.93-4.01 (m, 4H), 4.01-4.09 (m, 4H), 4.58 (d, J=5.2 Hz, 2H), 6.84 (s, 2H), 6.91-6.93 (m, 2H), 7.36-7.42 (m, 2H), 9.81 (s, 1H); $^{13}$C NMR (100 MHz, CDCl$_3$, 298 K): δ=26.4, 29.2, 29.3, 29.6, 29.6, 29.7, 29.8, 29.8, 65.4, 69.1, 69.1, 69.3, 69.5 (12 signals are missing, possibly because of signal overlapping), 111.2, 111.9, 113.2, 114.2, 119.7, 126.6, 129.9, 133.9, 148.9, 149.6, 149.6, 154.9, 191.0; HR-MS (ESI): calcd for C$_{38}$H$_{58}$O$_6$Na$^+$ [M+Na]$^+$, m/z 633.4131. found, m/z 633.4141.

Triol S5:

Following the procedure described above for S4, the reaction of the mono-alcohol S4 (1.33 g, 2.18 mmol) and Sc(OTf)$_3$ (54 mg, 0.11 mmol) in CHCl$_3$ (11 mL) for 16 h afforded the trialdehyde as a light yellow solid, which was reacted with NaBH$_4$ (50 mg, 1.21 mmole) in isopropyl alcohol (30 mL) and CH$_2$Cl$_2$ (30 mL) at room temperature for 16 h to afford a white solid S5 (0.25 g, 19%).

Mp: 117-119° C.; $^1$H NMR (400 MHz, CDCl$_3$, 298 K): δ=1.20-1.52 (m, 96H), 1.67-1.81 (m, 24H), 3.46 (d, J=13.6 Hz, 3H), 3.82-3.89 (m, 6H), 3.92-3.99 (m, 18H), 4.56 (s, 6H), 4.68 (d, J=13.6 Hz, 3H), 6.80 (s, 6H), 6.83 (s, 6H), 6.89 (s, 3H); $^{13}$C NMR (100 MHz, CDCl$_3$, 298 K): δ=26.3, 26.3, 26.4, 29.5, 29.6, 29.6, 29.8, 29.8, 29.8, 36.4, 65.3, 69.2, 69.5, 69.7, 113.2, 114.2, 116.2, 119.7, 132.3, 133.9, 148.0, 148.9, 149.6 (12 aliphatic and 3 aromatic signals are missing, possibly because of signal overlapping); HR-MS (ESI): calcd for C$_{114}$H$_{174}$O$_{15}^+$ [M]$^+$, m/z 1783.2853. found, m/z 1783.2791.

Figure 1B:
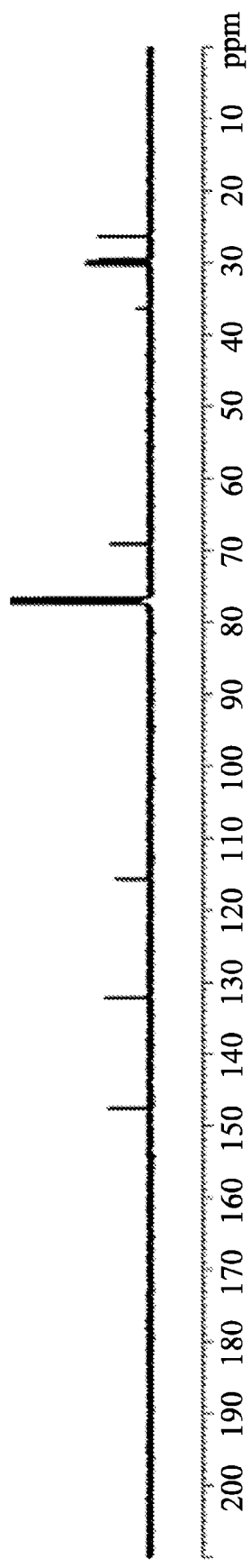

CTV1:

Following the procedure described above for S5, the reaction of the triol S5 (0.10 g, 0.056 mmol) and scandium triflate (60 mg, 0.12 mmol) in CHCl$_3$ (25 mL/30 mL) at 60° C. for 2 days afforded a white solid CTV1 (33 mg, 34%). The $^1$H NMR and $^{13}$C NMR spectra of CTV1 are shown in FIGS. 1A and 1B. All related spectral data are listed below.

Mp: 258° C. (dec); $^1$H NMR (400 MHz, CDCl$_3$, 298 K): δ=1.12-1.42 (m, 96H), 1.60-1.83 (m, 24H), 3.46 (d, J=13.6 Hz, 6H), 3.77-3.86 (m, 12H), 4.00-4.07 (m, 12H), 4.68 (d, J=13.6, 6H), 6.80 (s, 12H); $^{13}$C NMR (100 MHz, CDCl$_3$, 298 K): δ=26.3, 29.4, 29.8, 30.2, 30.2, 36.4, 69.1, 115.6, 132.1, 147.6; HR-MS (ESI): calcd for C$_{114}$H$_{168}$O$_{12}$Na$^+$ [M+Na]$^+$, m/z 1752.2432. found, m/z 1752.2488.

Synthesis of CTV2

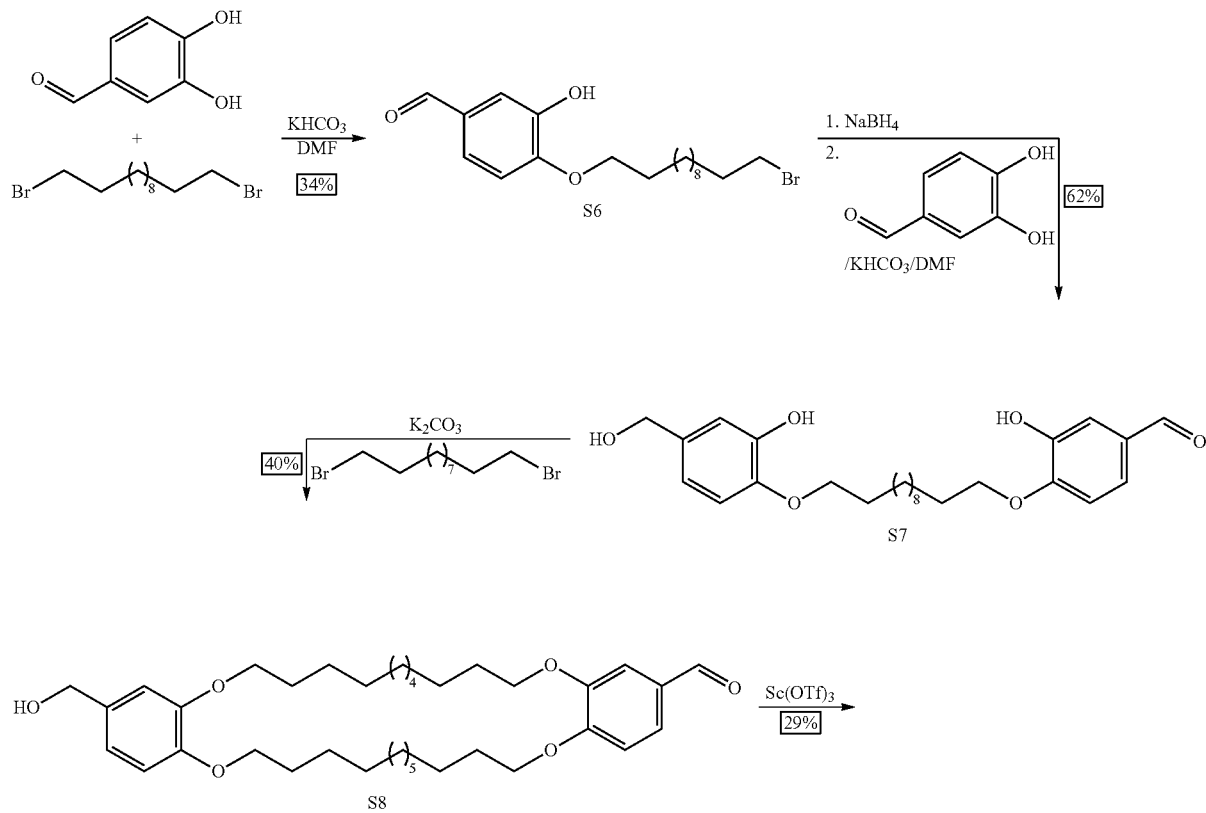

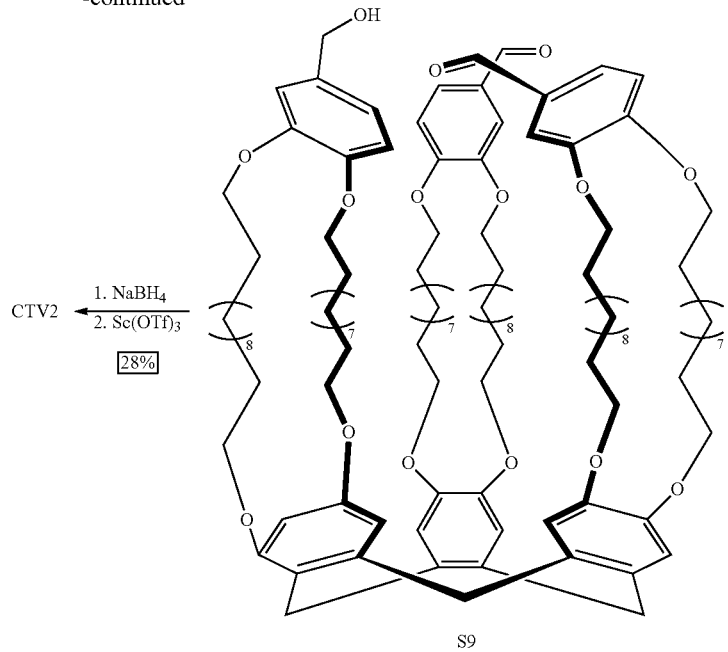

S9

Aldehyde S6:

The reaction of potassium bicarbonate (0.67 g, 6.70 mmol), 3,4-dihydroxybenzaldehyde (0.93 g, 6.70 mmol), and 1,12-dibromododecane (2.00 g, 6.09 mmol) in DMF (60 mL) at 55° C. for 40 h afforded aldehyde S6 as a white solid (0.81 g, 34%).

Mp: 74-75° C.; $^1$H NMR (400 MHz, CDCl$_3$, 298 K): δ=1.20-1.46 (m, 16H), 1.75-1.84 (m, 4H), 3.34 (t, J=6.8 Hz, 2H), 4.07 (t, J=6.6 Hz, 2H), 6.04 (s, 1H), 6.89 (d, J=8.2 Hz, 1H), 7.35 (dd, J=8.2, 2.0 Hz, 1H), 7.38 (d, J=2 Hz, 1H), 9.77 (s, 1H); $^{13}$C NMR (100 MHz, CDCl$_3$, 298 K): δ=25.8, 28.0, 28.6, 28.8, 29.1, 29.2, 29.3, 32.7, 33.9, 69.2 (2 signals are missing, possibly because of signal overlapping), 110.8, 113.9, 124.4, 130.2, 146.1, 151.3, 190.9; HR-MS (ESI): calcd for C$_{19}$H$_{30}$BrO$_3$$^+$ [M+H]$^+$, m/z 385.1373. found, m/z 385.1380.

Alcohol S7:

Following the procedure described above for S6, the reaction of the aldehyde S6 (0.81 g, 2.10 mmol) and NaBH$_4$ (40 mg, 1.05 mmol) in methanol (200 mL) at room temperature for 2 h afforded a white solid (0.79 g, 97%). The white solid was then reacted with 3,4-dihydroxybenzaldehyde (0.31 g, 2.24 mmol) and potassium bicarbonate (0.23 g, 2.25 mmol) in DMF DMF (50 mL) at 55° C. for 36 h to afford a white solid S7 (0.58 g, 64%).

Mp: 136-137° C.; $^1$H NMR (400 MHz, CDCl$_3$, 298 K): δ=1.25-1.50 (m, 16H), 1.73-1.89 (m, 4H), 4.01 (t, J=6.4 Hz, 2H), 4.11 (t, J=6.7 Hz, 2H), 4.56 (s, 2H), 5.67 (br, 2H), 6.80 (s, 2H), 6.90-6.96 (m, 2H), 7.36-7.44 (m, 2H), 9.81 (s, 1H); $^{13}$C NMR (100 MHz, CDCl$_3$, 298 K): δ=25.9, 26.0, 29.0, 29.2, 29.2, 29.3, 29.5, 29.5, 65.1, 69.1, 69.3 (2 signals are missing, possibly because of signal overlapping), 110.9, 111.6, 113.5, 114.1, 118.8, 124.4, 130.5, 134.2, 145.5, 145.9, 146.2, 151.3, 191.0; HR-MS (ESI): calcd for C$_{26}$H$_{35}$O$_6$$^-$ [M−H]$^-$, m/z 443.2439. found, m/z 443.2445.

Macrocycle S8:

Following the procedure described above for S7, the reaction of the diol S7 (3.74 g, 8.4 mmol), 1,11-dibromoundecane (2.64 g, 8.4 mmol) and K$_2$CO$_3$ (13.9 g, 101 mmol) in DMF (840 mL) at 60° C. for 5 days afforded a white solid S8 (2.01 g, 40%).

$^1$H NMR (400 MHz, CDCl$_3$, 298 K): δ=1.25-1.40 (m, 22H), 1.44-1.57 (m, 8H), 1.74-1.87 (m, 8H), 3.94-3.99 (m, 4H), 4.00-4.09 (m, 4H), 4.58 (s, 2H), 6.83 (s, 2H), 6.88-6.94 (m, 2H), 7.34-7.41 (m, 2H), 9.78 (s, 1H); $^{13}$C NMR (100 MHz, CDCl$_3$, 298 K): $^{13}$C NMR (100 MHz, CDCl$_3$, 298 K): δ=26.4, 26.4, 26.5, 26.6, 29.3, 29.4, 29.6, 29.6, 29.6, 29.7, 29.7, 29.8, 29.8, 29.8, 29.9, 30.0, 30.1, 65.3, 69.0, 69.1, 69.4, (3 signals missing, possibly because of signal overlap), 111.8, 111.6, 112.8, 113.9, 119.4, 126.5, 129.7, 133.7, 148.6, 149.3, 149.3, 154.6, 190.7; HR-MS (ESI): calcd for C$_{37}$H$_{56}$O$_6$Na$^+$ [M+Na]$^+$, m/z 619.40. found, m/z 619.39746.

Trialdehyde S9:

Following the procedure described above for S8, the reaction of the macrocycle S8 (0.2 g, 0.34 mmol) and Sc(OTf)$_3$ (8.4 mg, 0.017 mmol) in CHCl$_3$ (3.35 mL) at 70° C. for 16 h afforded a light-yellow solid S9 (55 mg, 29%).

$^1$H NMR (400 MHz, CDCl$_3$, 298 K): δ=1.20-1.55 (m, 90H), 1.68-1.87 (m, 24H), 3.46 (d, J=14.0 Hz, 3H), 3.82-4.10 (m, 24H), 4.68 (d, J=14.0 Hz, 3H), 6.80-6.83 (m, 6H), 6.89-6.94 (m, 3H), 7.34-7.41 (m, 6H), 9.79 (s, 3H); $^{13}$C NMR (100 MHz, CDCl$_3$, 298 K): δ=29.2, 29.3, 29.5, 29.6, 29.7, 29.7, 29.7, 29.9, 29.9, 29.9, 36.5, 69.1, 69.1, 69.5, 69.7 (9 signals are missing, possibly because of signal overlapping), 111.0, 111.8, 116.0, 116.3, 126.6, 129.9, 132.2, 132.3, 147.9, 148.0, 149.6, 154.8, 191.0; HR-MS (ESI): calcd for C$_{111}$H$_{162}$O$_{15}$Na$^+$ [M+Na]$^+$, m/z 1758.1811. found, m/z 1758.1812.

Figure 2A:
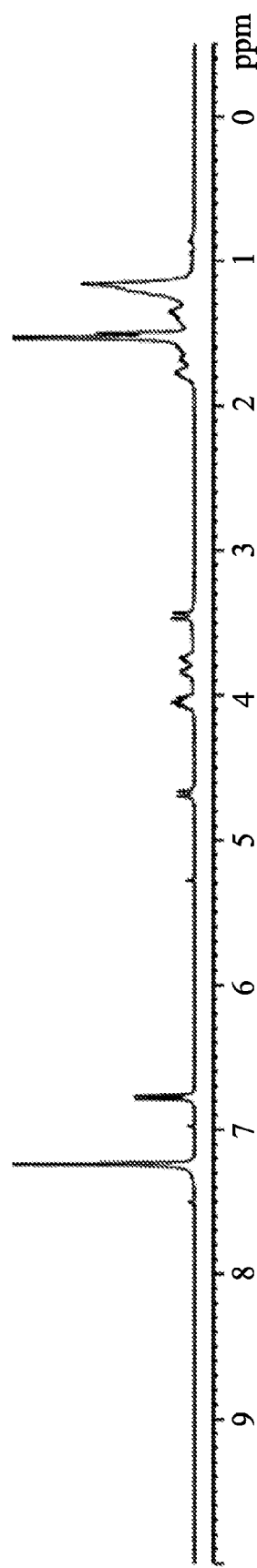
FIGS. 2A and 2B are $^1$H NMR (400 MHz, CDCl$_3$, 298 K) and $^{13}$C NMR (100 MHz, CDCl$_3$, 298 K) spectra of CTV2, respectively.
Figure 2B:
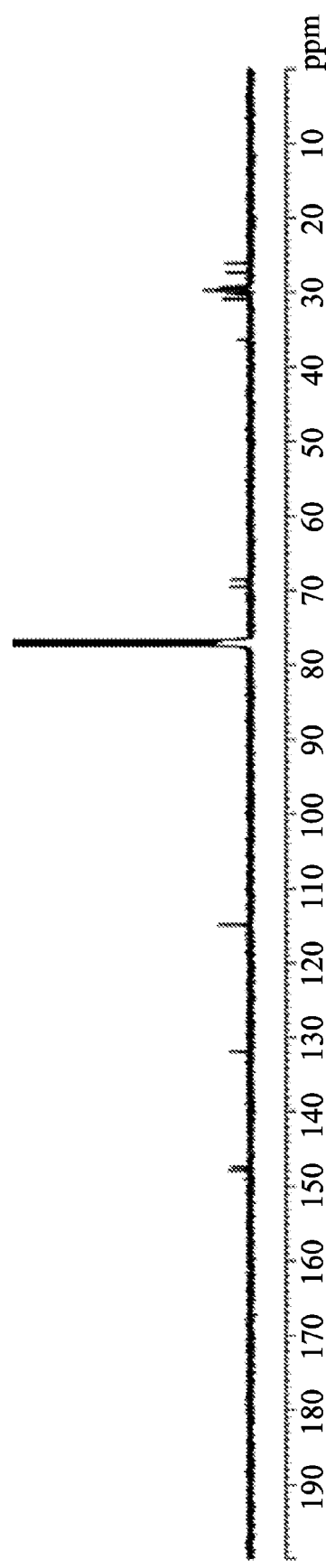

CTV2:

Following the procedure described above for S9, the reaction of the trialdehyde S9 (55 mg, 32 µmol) and NaBH$_4$ (4.84 mg, 0.13 mmol) in isopropyl alcohol (1 mL) and CH$_2$Cl$_2$ (1 mL) at room temperature for 16 h afford a white solid. The white solid was ten reacted with scandium triflate (11 mg, 23 µmol) in CHCl$_3$ (10 mL) at 60° C. for 3 days to afford a white solid CTV2 (15 mg, 28%). The $^1$H NMR and $^{13}$C NMR spectra of CTV2 are shown in FIGS. 2A and 2B. All related spectral data are listed below.

Mp: >261° C. (dec.); $^1$H NMR (400 MHz, CDCl$_3$, 298 K): δ=1.11-1.46 (m, 90H), 1.57-1.85 (m, 24H), 3.45 (d, J=13.8 Hz, 6H), 3.71-3.88 (m, 12H), 4.00-4.10 (m, 12H), 4.68 (d, J=13.7, 6H), 6.77 (s, 6H), 6.79 (s, 6H); $^{13}$C NMR (100 MHz, CDCl$_3$, 298 K): δ=26.0, 27.3, 29.2, 29.3, 29.6, 29.7, 30.1, 30.3, 30.8, 36.3, 68.5, 69.5, 114.9, 131.9, 147.4, 147.8 (3 signals missing, possibly because of signal overlap); HR-MS (ESI): calcd for C$_{111}$H$_{162}$O$_{12}$Na$^+$ [M+Na]$^+$, m/z 1710.20. found, m/z 1710.19641.

Synthesis of CTV3

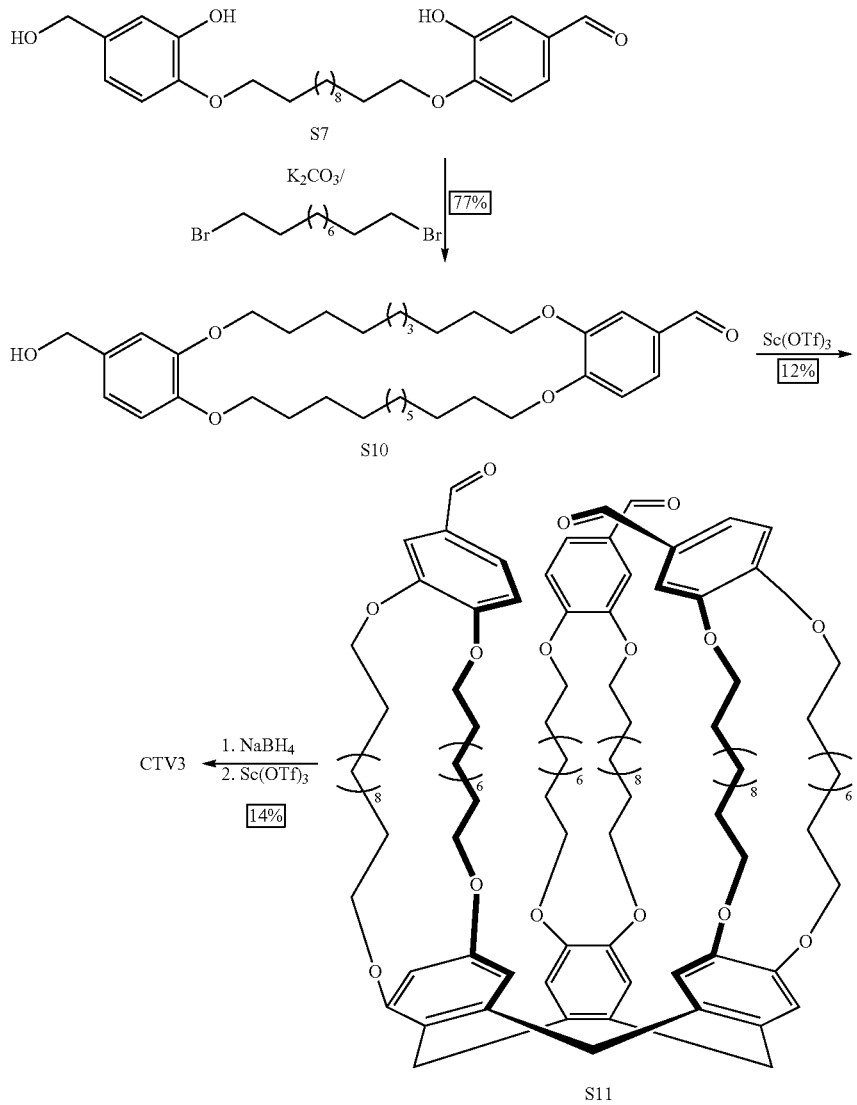

Macrocycle S10:

Following the procedure described above for S7, the reaction of the diol S7 (3.74 g, 8.4 mmol), 1,10-dibromodecane (2.52 g, 8.4 mmol) and K$_2$CO$_3$ (13.9 g, 101 mmol) in DMF (840 mL) at 60° C. for 5 days afforded a white solid S10 (1.88 g, 77%).

Macrocycle S10: $^1$H NMR (400 MHz, CDCl$_3$, 298 K): δ=1.26-1.40 (m, 20H), 1.45-1.53 (m, 8H), 1.73-1.86 (m, 8H), 3.95-4.00 (m, 4H), 4.01-4.09 (m, 4H), 4.58 (s, 2H), 6.83 (s, 2H), 6.89-6.94 (m, 2H), 7.36-7.41 (m, 2H), 9.80 (s, 1H); $^{13}$C NMR (100 MHz, CDCl$_3$, 298 K): δ=26.2, 26.3, 26.5, 26.5, 29.2, 29.4, 29.5, 29.6, 29.7, 29.7, 29.8, 29.9, 29.9, 65.4, 69.0, 69.1, 69.5, (7 signals missing, possibly because of signal overlap) 111.1, 111.8, 113.0, 114.2, 119.6, 126.6, 129.9, 133.8, 148.9, 149.6, 154.9, 191.0 (1 signals missing, possibly because of signal overlap); HR-MS (ESI): calcd for C$_{36}$H$_{54}$O$_6^+$ [M]$^+$, m/z 582.3920. found, m/z 582.3901.

Trialdehyde S11:

Following the procedure described above for S10, the reaction of the macrocycle S10 (1.88 g, 3.23 mmol) and Sc(OTf)$_3$ (79.6 mg, 0.16 mmol) in CHCl$_3$ (18.8 mL) at 70° C. for 16 h afforded a light-yellow solid S11 (215.2 mg, 12%).

$^1$H NMR (400 MHz, CDCl$_3$, 298 K): δ=1.20-1.56 (m, 88H), 1.68-1.88 (m, 24H), 3.47 (d, J=13.8 3H), 3.84-4.10 (m, 24H), 4.68 (d, J=13.6 Hz, 3H), 6.79-6.82 (m, 6H), 6.89-6.94 (m, 3H), 7.35-7.41 (m, 6H), 9.79 (s, 3H); $^{13}$C NMR (100 MHz, CDCl$_3$, 298 K): δ=26.2, 26.3, 26.4, 26.5, 29.2, 29.2, 29.4, 29.5, 29.5, 29.6, 29.6, 29.7, 29.8, 29.9, 36.4, 69.0, 69.1, 69.5, 69.7, (4 signals are missing, possibly because of signal overlapping), 111.0, 111.8, 116.0, 116.3, 126.6, 129.9, 132.2, 132.3, 147.9, 148.0, 149.6, 154.8, 191.0; HR-MS (ESI): calcd for C$_{108}$H$_{156}$O$_{15}^+$ [M]$^+$, m/z 1693.1444. found, m/z 1693.1444.

Figure 3A:
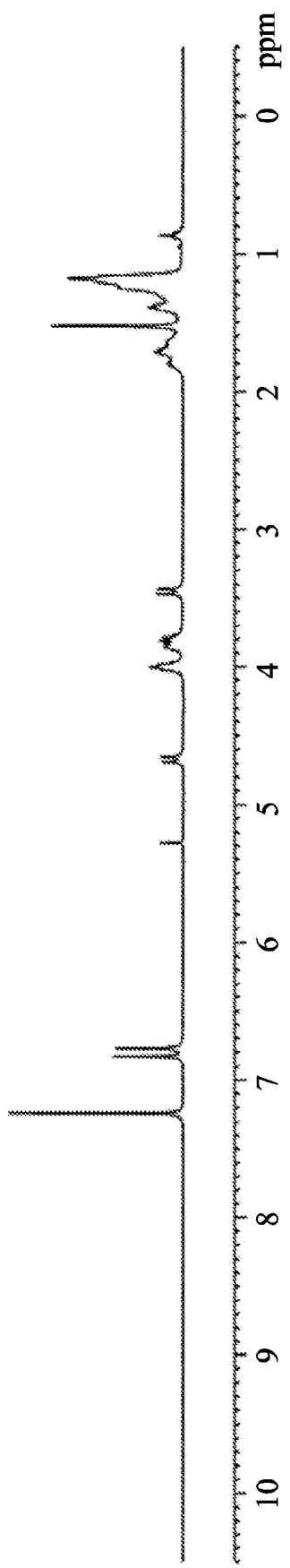
FIGS. 3A and 3B are $^1$H NMR (400 MHz, CDCl$_3$, 298 K) and $^{13}$C NMR (100 MHz, CDCl$_3$, 298 K) spectra of CTV3, respectively.
Figure 3B:
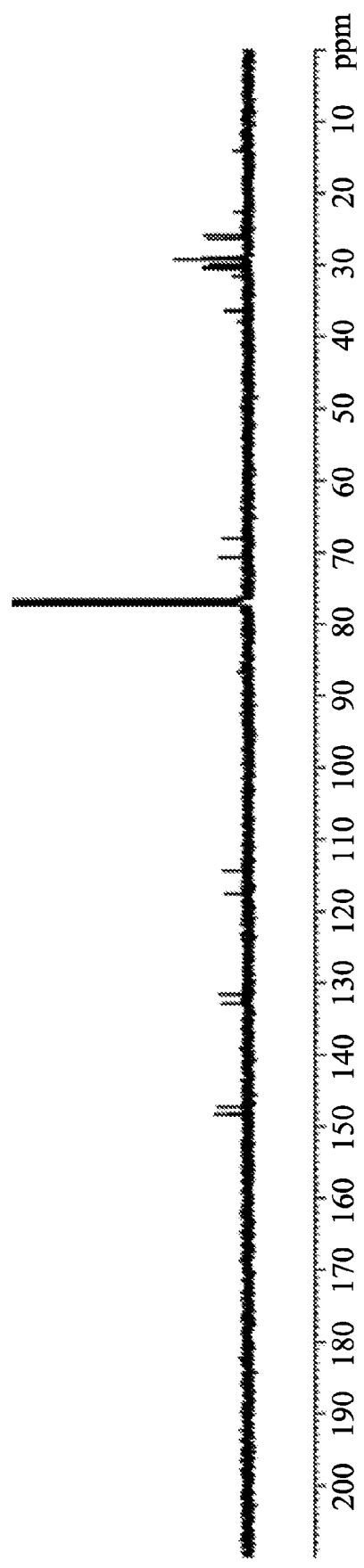

CTV3:

Following the procedure described above for S11, the reaction of the trialdehyde S11 (215 mg, 130 ⌈mol) and NaBH$_4$ (19.2 mg, 0.51 mmol) in isopropyl alcohol (5.5 mL) and CH$_2$Cl$_2$ (5.5 mL) at room temperature for 16 h afford a white solid. The white solid was ten reacted with scandium triflate (81.4 mg, 165 ⌈mol) in CHCl$_3$ (94 mL) at 60° C. for 3 days to afford a white solid CTV3 (30 mg, 14%). The $^1$H NMR and $^{13}$C NMR spectra of CTV3 are shown in FIGS. 3A and 3B. All related spectral data are listed below.

$^1$H NMR (400 MHz, CDCl$_3$, 298 K): δ=1.12-1.44 (m, 84H), 1.57-1.87 (m, 24H), 3.45 (d, J=13.6 Hz, 6H), 3.77-3.90 (m, 12H), 3.96-4.06 (m, 12H), 4.67 (d, J=13.6, 6H), 6.77 (s, 6H), 6.83 (s, 6H); $^{13}$C NMR (100 MHz, CDCl$_3$, 298 K): δ=25.9, 26.3, 29.0, 29.2, 29.9, 30.2, 30.5, 31.6, 36.4, 68.0, 70.7, (1 signals are missing, possibly because of signal overlapping), 114.3, 117.6, 131.6, 132.9, 147.2, 148.3; HR-MS (ESI): calcd for C$_{108}$H$_{156}$O$_{12}$ [M]$^+$, m/z 1645.1597. found, m/z 1645.1632.

Synthesis of CTV4

Macrocycle S12:

Following the procedure described above for S7, the reaction of the diol S7 (2.00 g, 4.50 mmol), bis(4-bromobutyl) succinate (1.75 g, 4.50 mmol) and K$_2$CO$_3$ (3.73 g, 26.99 mmol) in DMF (400 mL) at 60° C. for 6 days afforded a white solid S12 (0.59 g, 19%).

$^1$H NMR (400 MHz, CDCl$_3$, 298 K): δ=1.21-1.41 (m, 12H), 1.42-1.55 (m, 4H), 1.56-2.00 (m, 12H), 2.60 (s, 4H), 3.40-4.06 (m, 8H), 4.18-4.21 (m, 4H), 4.58 (s, 2H), 6.81-6.93 (m, 4H), 7.35 (d, J=1.6 Hz, 1H), 7.40 (dd, J=8.4, 1.8 Hz, 1H), 9.79 (s, 1H); $^{13}$C NMR (100 MHz, CDCl$_3$, 298 K): δ=26.2, 26.3, 29.2, 29.2, 29.4, 29.5, 29.5, 29.6, 29.6, 64.6, 64.7, 65.3, 68.7, 68.7, 69.0, 69.2, 110.9, 111.5, 113.1, 113.5, 119.8, 126.8, 129.6, 133.5, 148.7, 148.8, 149.0, 154.6, 171.9, 172.0, 190.7 (seven aliphatic signals are missing, possibly because of signal overlapping); HR-MS (ESI): calcd for C$_{38}$H$_{54}$O$_{10}$Na$^+$ [M+Na]$^+$, m/z 693.3615. found, m/z 693.3625.

Trialdehyde S13:

Following the procedure described above for S12, the reaction of the mono-alcohol S12 (1.82 g, 2.71 mmol) and

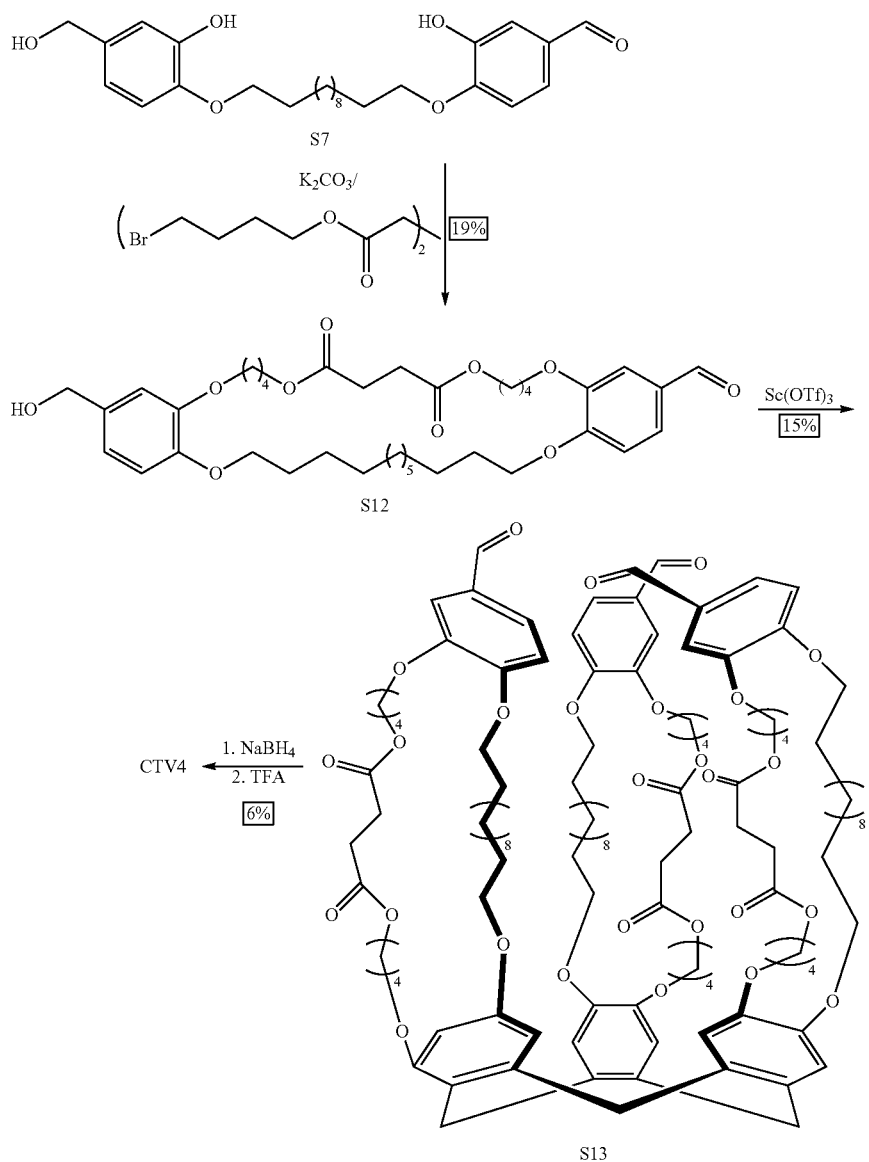

Sc(OTf)$_3$ (67 mg, 0.140 mmol) in CHCl$_3$ (14 mL) at 70° C. for 16 h afforded the trialdehyde as a light-yellow oil S13 (274 mg, 15%).

$^1$H NMR (400 MHz, CDCl$_3$, 298 K): δ=1.16-1.52 (m, 42H), 1.67-1.94 (m, 42H), 2.56 (s, 12H), 3.46 (d, J=13.6 Hz, 3H), 3.78-4.00 (m, 12H), 4.00-4.09 (m, 12H), 4.09-4.24 (m, 12H), 4.67 (d, J=13.6, 3H), 6.79 (s, 3H), 6.80 (s, 3H), 6.91 (d, J=8.0 Hz, 3H), 7.35 (d, J=1.6 Hz, 3H), 7.39 (dd, J=8.2, 1.8 Hz, 3H), 9.79 (s, 3H); $^{13}$C NMR (100 MHz, CDCl$_3$, 298 K): δ=25.6, 25.7, 26.0, 26.1, 29.0, 29.2, 29.3, 29.3, 29.4, 29.4, 29.5, 36.3, 64.5, 68.5, 68.9, 69.2, 69.3, 110.8, 111.5, 115.6, 116.4, 126.9, 130.0, 132.0, 132.5, 147.5, 148.0, 149.1, 154.7, 172.1, 190.8 (six aliphatic and one aromatic signals are missing, possibly because of signal overlapping); HR-MS (ESI): calcd for C$_{114}$H$_{156}$O$_{27}$Na$^+$ [M+Na]$^+$, m/z 1980.0732. found, m/z 1980.0764.

Figure 4A:
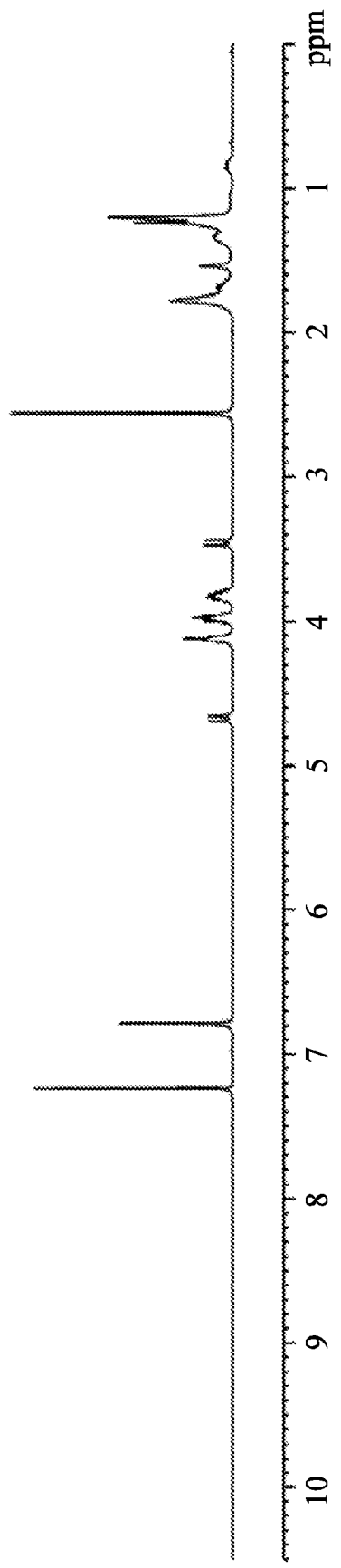
FIGS. 4A and 4B are $^1$H NMR (400 MHz, CDCl$_3$, 298 K) and $^{13}$C NMR (100 MHz, CDCl$_3$, 298 K) spectra of CTV4, respectively.
Figure 4B:
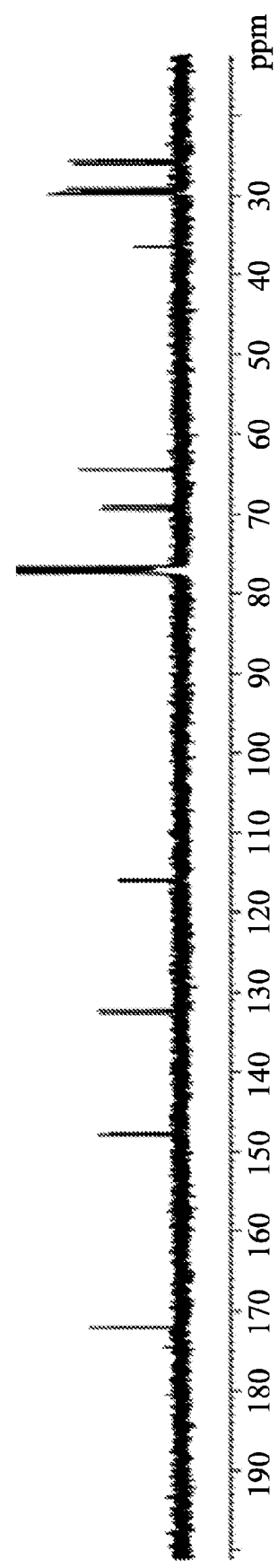

CTV4:

Following the procedure described above for S13, the reaction of the trialdehyde S13 (274 mg, 0.14 mmol) and NaBH$_4$ (16 mg, 0.42 mmol) in methanol (4.7 mL) and CH$_2$Cl$_2$ (9.3 mL) at −15° C. for 3.5 h afford a white solid. The white solid was then reacted with 10% TFA (15 mL) in CHCl$_3$ (102 mL) at room temperature for 2 days to afford a white solid CTV4 (16 mg, 6%). The $^1$H NMR and $^{13}$C NMR spectra of CTV4 are shown in FIGS. 4A and 4B. All related spectral data are listed below.

$^1$H NMR (400 MHz, CDCl$_3$, 298 K): δ=1.13-1.45 (m, 42H), 1.59-1.89 (m, 42H), 2.56 (s, 12H), 3.45 (d, J=13.6 Hz, 6H), 3.75-3.91 (m, 12H), 3.91-4.05 (m, 12H), 4.06-4.21 (br, 12H), 4.67 (d, J=14.0, 6H), 6.78 (s, 6H), 6.79 (s, 6H); $^{13}$C NMR (100 MHz, CDCl$_3$, 298 K): δ=25.7, 26.1, 26.1, 29.2, 29.5, 29.7, 29.7, 29.8, 36.4, 64.4, 69.0, 69.4, 115.9, 116.1, 132.2, 132.5, 147.7, 147.9, 172.0; HR-MS (ESI): calcd for C$_{114}$H$_{156}$NaO$_{24}$$^+$ [M+Na]$^+$, m/z 1932.0884. found, m/z 1931.9346.

Synthesis of CTV5

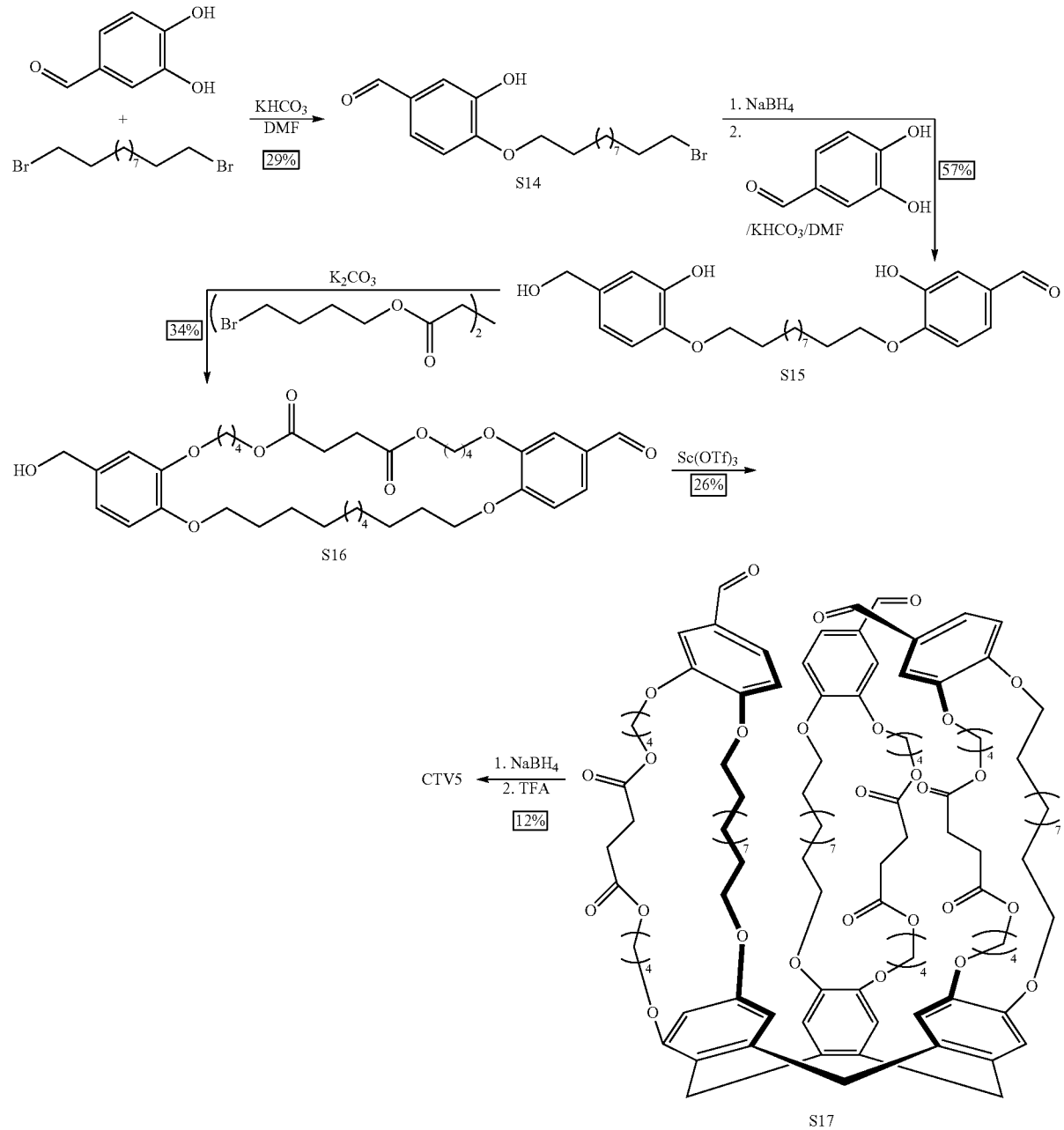

S17

Aldehyde S14:

The reaction of potassium bicarbonate (7.16 g, 70.8 mmol), 3,4-dihydroxybenzaldehyde (8.15 g, 59.0 mmol), and 1,11-dibromoundecane (22.3 g, 70.8 mmol) in DMF (393 mL) at 60° C. for 2 days afforded aldehyde S14 as a white solid (6.38 g, 29%).

Mp: 60-61° C.; $^1$H NMR (400 MHz, CDCl$_3$, 298 K): δ=1.28-1.48 (m, 14H), 1.79-1.87 (m, 4H), 3.38 (t, J=6.8 Hz, 2H), 4.11 (t, J=6.4 Hz, 2H), 5.75 (s, 1H), 6.93 (d, J=8.4 Hz, 1H), 7.39 (dd, J=8.4, 2 Hz, 1H), 7.42 (d, J=2 Hz, 1H), 9.81 (s, 1H); $^{13}$C NMR (100 MHz, CDCl$_3$, 298 K): δ=25.9, 28.1, 28.7, 29.0, 29.2, 29.3, 29.4, 29.4, 32.8, 34.0, 69.3, 110.9, 114.0, 124.4, 130.5, 146.2, 151.2, 190.9; HR-MS (ESI): calcd for C$_{18}$H$_{26}$O$_3$Br$^-$ [M−H]$^-$, m/z 369.1065. found, m/z 369.1062.

Alcohol S15:

Following the procedure described above for S14, the reaction of the aldehyde S14 (6.38 g, 17.19 mmol) and NaBH$_4$ (650 mg, 17.19 mmol) in methanol (30 mL) and CH$_2$Cl$_2$ (60 mL) at room temperature for 2 h afforded a white solid (1.89 g, 98%). The white solid was then reacted with 3,4-dihydroxybenzaldehyde (2.62 g, 18.94 mmol) and potassium bicarbonate (1.92 g, 18.94 mmol) in DMF (115 mL) at 60° C. for 2 days to afford a white solid S15 (4.19 g, 57%).

Mp: 94-97° C.; $^1$H NMR (400 MHz, CDCl$_3$, 298 K): δ=1.29-1.48 (m, 14H), 1.75-1.87 (m, 4H), 4.01 (t, J=6.4 Hz, 2H), 4.11 (t, J=6.8 Hz, 2H), 4.56 (s, 2H), 5.68 (s, 1H), 5.81 (s, 1H), 6.78-6.82 (m, 2H), 6.91-6.93 (m, 2H), 7.38 (dd, J=8, 2 Hz, 1H), 7.41 (d, J=2 Hz, 1H), 9.81 (s, 1H); $^{13}$C NMR (100 MHz, CDCl$_3$, 298 K): δ=25.9, 25.9, 29.0, 29.2, 29.2, 29.3, 29.4, 29.4, 29.4, 65.1, 69.0, 69.3, 110.9, 111.6, 113.5, 114.1, 118.8, 124.4, 130.5, 134.2, 145.5, 145.9, 146.2, 151.3, 191.0; HR-MS (ESI): calcd for C$_{25}$H$_{33}$O$_6$$^-$ [M−H]$^-$, m/z 429.2277. found, m/z 429.2272.

Macrocycle S16:

Following the procedure described above for S15, the reaction of the diol S15 (3.64 g, 8.46 mmol), Bis(4-bromobutyl)succinate (3.28 g, 8.46 mmol) and K$_2$CO$_3$ (7.02 g, 50.77 mmol) in DMF (846 mL) at 60° C. for 5 days afforded a white solid S16 (1.83 g, 34%).

Mp: 125-127° C.; $^1$H NMR (400 MHz, CDCl$_3$, 298 K): δ=1.29-1.33 (m, 10H), 1.42-1.49 (m, 4H), 1.70-1.89 (m, 12H), 2.59 (s, 4H), 3.93-4.05 (m, 8H), 4.17-4.20 (m, 4H), 4.56 (s, 2H), 6.80-6.93 (m, 4H), 7.35 (d, J=1.6 Hz, 1H), 7.40 (dd, J=8.4, 1.6 Hz, 1H), 9.79 (s, 1H); $^{13}$C NMR (100 MHz, CDCl$_3$, 298 K): δ=25.6, 25.7, 25.8, 25.9, 26.2, 26.2, 29.1, 29.2, 29.4, 29.4, 29.5, 29.6, 29.6, 64.5, 64.6, 65.2, 68.6, 68.7, 69.0, 69.2, 111.0, 111.6, 113.2, 113.6, 119.9, 126.9, 129.8, 133.7, 148.8, 149.0, 149.2, 154.8, 172.1, 172.1, 190.9; HR-MS (ESI): calcd for C$_{37}$H$_{52}$O$_{10}$Na$^+$ [M+Na]$^+$, m/z 679.3458. found, m/z 679.3466.

Trialdehyde S17:

Following the procedure described above for S16, the reaction of the macrocycle S16 (700 mg, 1.07 mmol) and Sc(OTf)$_3$ (26 mg, 0.053 mmol) in CHCl$_3$ (14 mL) at room temperature for 16 h afforded a light-yellow oil (180 mg, 26%).

$^1$H NMR (400 MHz, CDCl$_3$, 298 K): δ=1.32-1.48 (m, 36H), 1.69-1.86 (m, 42H), 2.56 (s, 12H), 3.45 (d, J=14 Hz, 3H), 3.83-4.05 (m, 24H), 4.14-4.19 (m, 12H), 4.67 (d, J=13.6 Hz, 3H), 6.79 (s, 3H), 6.79 (s, 3H), 6.91 (d, J=8.4 Hz, 3H), 7.35 (d, J=1.6 Hz, 3H), 7.39 (dd, J=8.4, 1.6 Hz, 3H), 9.79 (s, 3H); $^{13}$C NMR (100 MHz, CDCl$_3$, 298 K): δ=25.6, 25.6, 25.7, 26.0, 26.1, 26.2, 29.0, 29.4, 29.4, 29.5, 29.6, 36.3, 64.4, 68.6, 69.0, 69.2, 69.4, 111.0, 111.6, 115.8, 116.5, 126.8, 129.8, 132.1, 132.6, 147.6, 148.0, 149.1, 154.7, 172.0, 190.7 (four aliphatic and one aromatic signals are missing, possibly because of signal overlapping); HR-MS (ESI): calcd for C$_{111}$H$_{150}$O$_{27}$Na$^+$ [M+Na]$^+$, m/z 1938.0261. found, m/z 1938.0191.

Figure 5A:
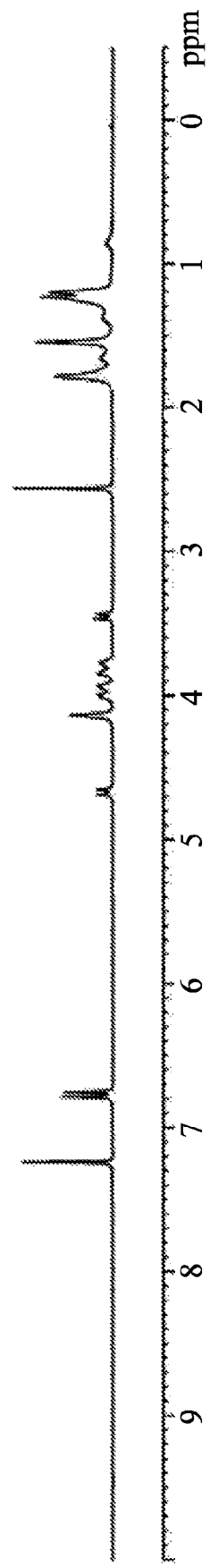
FIGS. 5A and 5B are $^1$H NMR (400 MHz, CDCl$_3$, 298 K) and $^{13}$C NMR (100 MHz, CDCl$_3$, 298 K) spectra of CTV5, respectively.
Figure 5B:
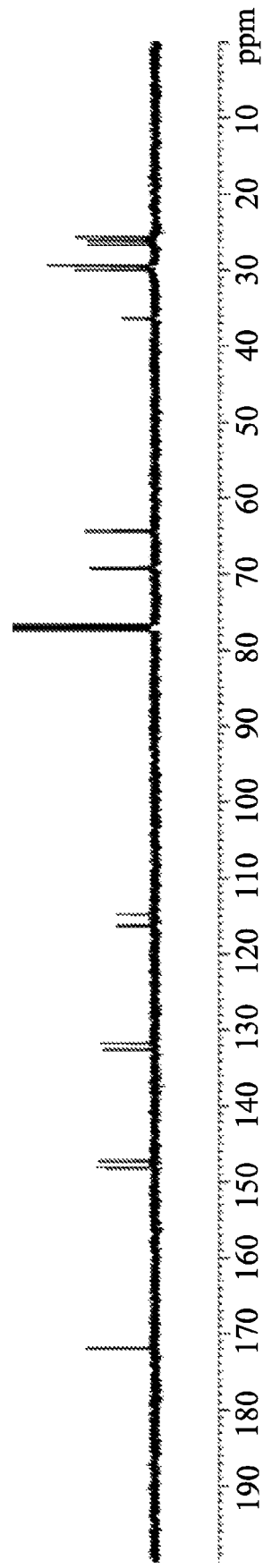

CTV5:

Following the procedure described above for S17, the reaction of the trialdehyde S17 (100 mg, 0.052 mmol) and NaBH$_4$ (4 mg, 0.1 mmol) in methanol (1.7 mL) and CH$_2$Cl$_2$ (3.4 mL) at −15° C. for 1.5 h afford a white solid. The white solid was then reacted with TFA (8 mL) in CHCl$_3$ (57 mL) at room temperature for 2 days to afford a white solid CTV5 (12 mg, 12%). The $^1$H NMR and $^{13}$C NMR spectra of CTV5 are shown in FIGS. 5A and 5B. All related spectral data are listed below.

$^1$H NMR (400 MHz, CDCl$_3$, 298 K): δ=1.20-1.38 (m, 36H), 1.55-1.78 (m, 42H), 2.56 (s, 12H), 3.45 (d, J=13.6 Hz, 6H), 3.75-3.85 (m, 12H), 3.93-4.03 (m, 12H), 4.14 (br, 12H), 4.67 (d, J=13.6 Hz, 6H), 6.75 (s, 6H), 6.79 (s, 6H); $^{13}$C NMR (100 MHz, CDCl$_3$, 298 K): δ=25.7, 26.1, 26.7, 29.3, 29.4, 29.6, 30.0 (one signal missing, possibly because of signal overlap), 36.3, 64.4, 69.1, 69.3, 114.8, 116.3, 131.8, 132.6, 147.3, 148.1, 172.0; HR-MS (ESI): calcd for C$_{111}$H$_{150}$NaO$_{24}$+[M+Na]$^+$, m/z 1890.0414. found, m/z 1890.0342.

Synthesis of CTV6

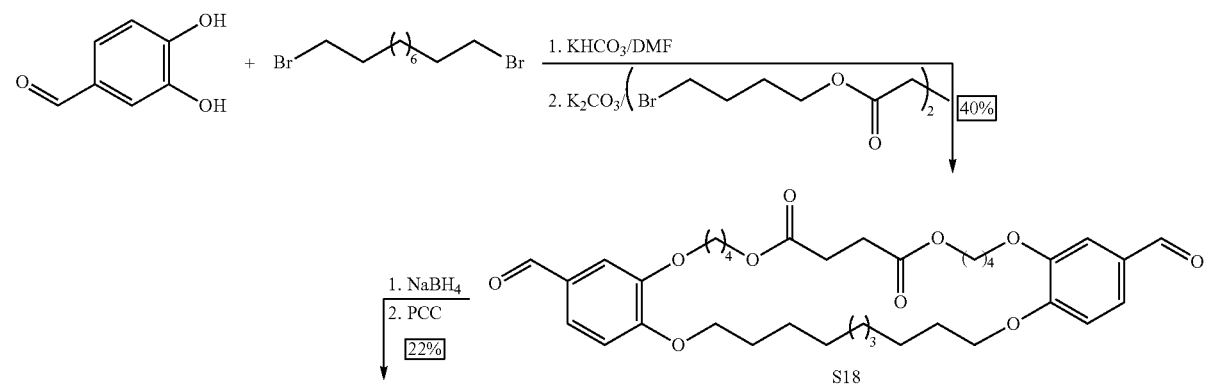

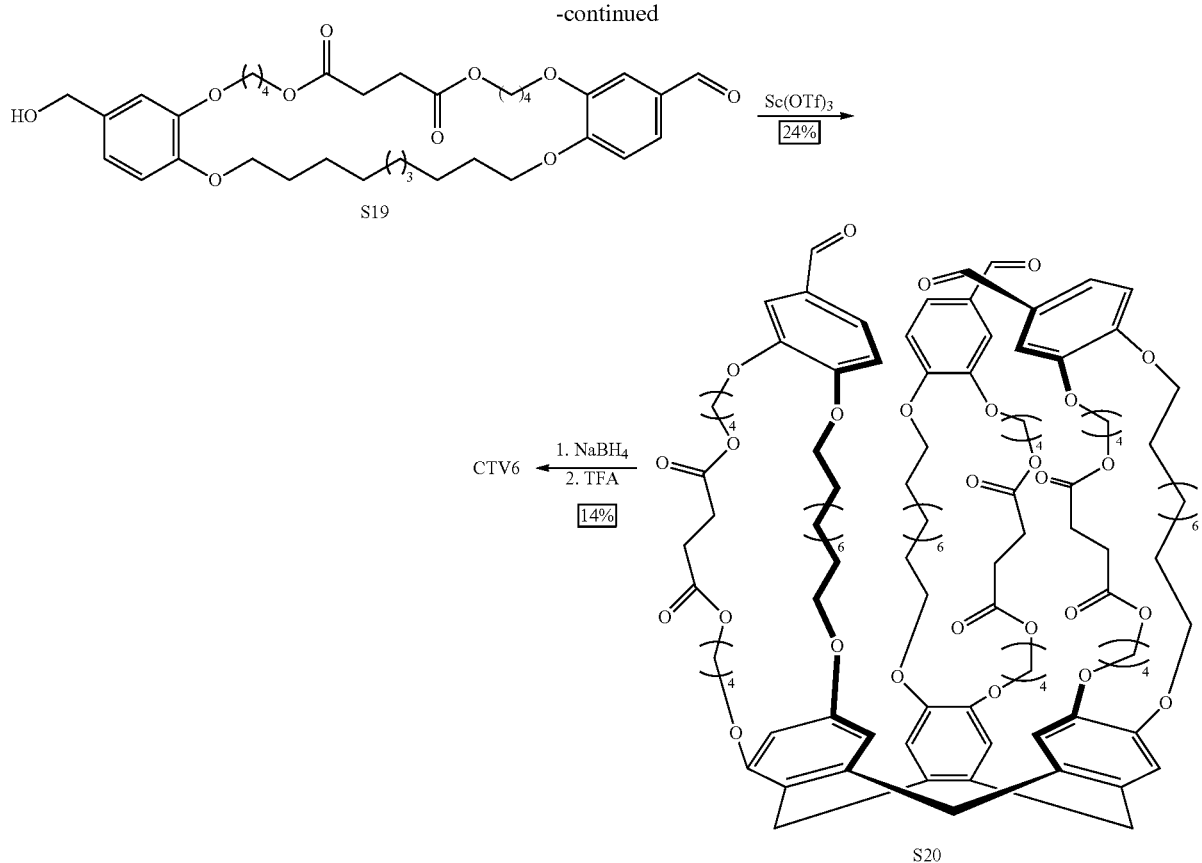

Macrocycle S18:

The reaction of the potassium bicarbonate (1.22 g, 12.03 mmol), 3,4-dihydroxybenzaldehyde (1.66 g, 12.03 mmol), and 1,10-dibromodecane (1.64 g, 5.47 mmol) in DMF (11 mL) at 65° C. for 2 days afforded a white solid. The white solid was then reacted with (bis(4-bromobutyl) succinate) (1.66 g, 4.28 mmol) and $K_2CO_3$ in DMF (427 mL) to afford a white solid S18 (3.64 g, 40%).

$^1$H NMR (400 MHz, CDCl$_3$, 298 K): δ=1.33-1.50 (m, 12H), 1.79-1.87 (m, 12H), 2.59 (s, 4H), 4.02-4.05 (m, 8H), 4.18-4.21 (m, 4H), 6.92 (d, J=8.4 Hz, 2H), 7.35 (d, J=1.6 Hz, 2H), 7.40 (dd, J=8, 1.2 Hz, 2H), 9.80 (s, 2H); $^{13}$C NMR (100 MHz, CDCl$_3$, 298 K): δ=25.6, 25.9, 26.2, 29.1, 29.1, 29.4, 29.5, 64.6, 68.7, 69.0, 110.9, 111.6, 126.9, 129.8, 149.2, 154.7, 172.1, 190.9; HR-MS (ESI): calcd for $C_{36}H_{48}O_{10}Na^+$ [M+Na]$^+$, m/z 663.3145. found, m/z 663.3177.

Alcohol S19:

Following the procedure described above for S18, the reaction of the dialdehyde S18 (2.13 g, 3.33 mmol) and NaBH$_4$ (126 mg, 3.33 mmol) in methanol (50 mL) and CH$_2$Cl$_2$ (50 mL) at 0° C. for 2 h afforded a white solid. The following reaction of the white solid, pyridinium chlorochromate (669 mg, 3.10 mmol) and 4-Å molecular sieves (2 g) in CH$_2$Cl$_2$ (124 mL) at room temperature for 3 h afforded a white solid S19 (712 mg, 22%).

$^1$H NMR (400 MHz, CDCl$_3$, 298 K): δ=1.32 (br, 8H), 1.43-1.48 (m, 4H), 1.74-1.89 (m, 12H), 2.59 (s, 4H), 3.93-4.07 (m, 8H), 4.19-4.21 (m, 4H), 4.57 (s, 2H), 6.80-6.93 (m, 4H), 7.35 (d, J=1.6 Hz, 1H), 7.40 (dd, J=8, 1.6 Hz, 1H), 9.80 (s, 1H); $^{13}$C NMR (100 MHz, CDCl$_3$, 298 K): δ=25.6, 25.8, 25.9, 25.9, 26.1, 26.2, 29.0, 29.2, 29.3, 29.4, 29.5, 29.5, (two signals missing, possibly because of signal overlap), 64.6, 64.6, 65.2, 68.7, 68.7, 69.0, 69.2, 110.9, 111.6, 113.1, 113.5, 119.9, 126.9, 129.8, 133.7, 148.8, 149.0, 149.2, 154.8, 172.1, (one signal missing, possibly because of signal overlap), 190.9; HR-MS (ESI): calcd for $C_{36}H_{50}O_{10}Na^+$ [M+Na]$^+$, m/z 665.3302. found, m/z 665.3344.

Trialdehyde S20:

Following the procedure described above for S19, the reaction of the mono-alcohol S19 (500 mg, 0.78 mmol) and Sc(OTf)$_3$ (19 mg, 0.039 mmol) in CHCl$_3$ (8 mL) at 70° C. for 16 h afforded the trialdehyde as a light-yellow oil S20 (118 mg, 24%).

$^1$H NMR (400 MHz, CDCl$_3$, 298 K): δ=1.30-1.47 (m, 30H), 1.69-1.85 (m, 42H), 2.55 (s, 12H), 3.45 (d, J=13.6 Hz, 3H), 3.82-4.04 (m, 24H), 4.14-4.20 (m, 12H), 4.67 (d, J=13.6 Hz, 3H), 6.78 (s, 3H), 6.79 (s, 3H), 6.91 (d, J=8.4 Hz, 3H), 7.34 (s, 3H), 7.39 (d, J=8.4, 3H), 9.79 (s, 3H); $^{13}$C NMR (100 MHz, CDCl$_3$, 298 K): δ=25.5, 25.7, 25.8, 25.9, 26.1, 26.2, 29.0, 29.0, 29.3, 29.3, 29.4, 29.4, 29.5, 36.3, 64.5, 64.5, 68.6, 68.9, 69.2, 69.3, 110.8, 111.5, 115.6, 116.4, 126.8, 129.7, 132.0, 132.5, 147.5, 148.0, 149.1, 154.7, 172.0, 172.0, 190.8 (one aliphatic signal is missing, possibly because of signal overlap); HR-MS (ESI): calcd for $C_{108}H_{144}O_{27}Na^+$ [M+Na]$^+$, m/z 1895.9793. found, m/z 1895.9826.

Figure 6A:
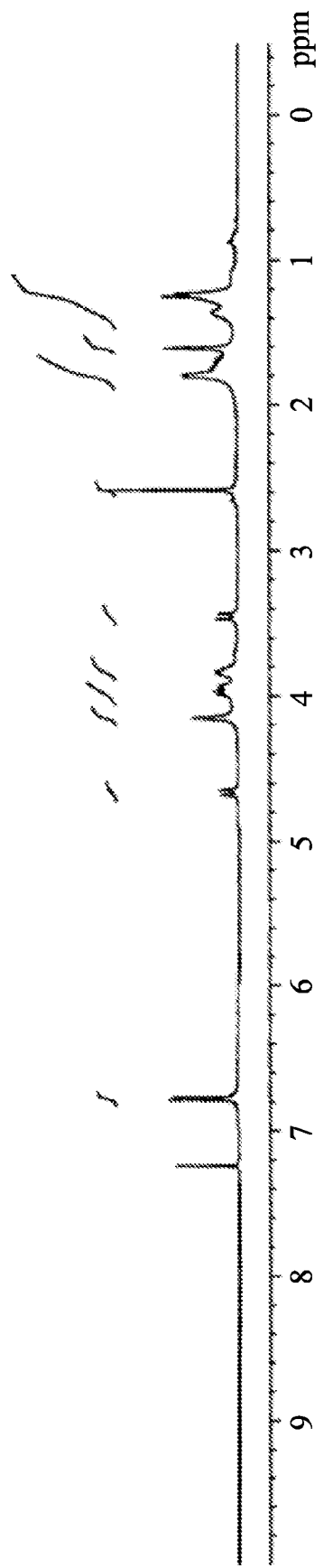
FIGS. 6A and 6B are $^1$H NMR (400 MHz, CDCl$_3$, 298 K) and $^{13}$C NMR (100 MHz, CDCl$_3$, 298 K) spectra of CTV6, respectively.
Figure 6B:
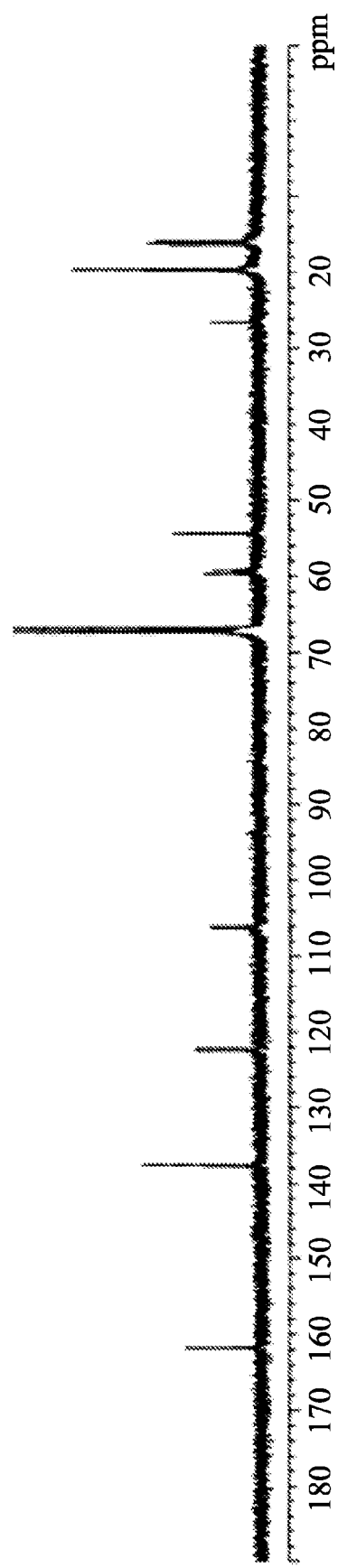

CTV6:

Following the procedure described above for S20, the reaction of the trialdehyde S20 (58 mg, 0.031 mmol) and NaBH$_4$ (4 mg, 0.047 mmol) in methanol (1.5 mL) and CH$_2$Cl$_2$ (1.5 mL) at 0° C. for 1.5 h afford a white solid. The white solid was then reacted with TFA (3 mL) in CHCl$_3$ (50 mL) at room temperature for 2 days to afford a white solid CTV6 (8 mg, 14%). The $^1$H NMR and $^{13}$C NMR spectra of CTV6 are shown in FIGS. 6A and 6B. All related spectral data are listed below.

$^1$H NMR (400 MHz, CDCl$_3$, 298 K): δ=1.23-1.39 (m, 30H), 1.64-1.82 (m, 42H), 2.58 (s, 12H), 3.45 (d, J=13.6 Hz, 6H), 3.79-3.87 (m, 12H), 3.91-4.00 (m, 12H), 4.15-4.16 (br, 12H), 4.66 (d, J=13.2 Hz, 6H), 6.77 (s, 6H), 6.78 (s, 6H); $^{13}$C NMR (100 MHz, CDCl$_3$, 298 K): δ=25.8, 26.1, 26.3, 29.5, 29.6, 29.7, 29.8, 36.5, 64.4, 69.1, 69.6, 116.0, 116.3, 132.2, 132.4, 147.6, (one signal missing, possibly because of signal overlap), 171.7; HR-MS (ESI): calcd for $C_{108}H_{144}NaO_{24}^+$ [M+Na]$^+$, m/z 1847.9945. found, m/z 1848.0018.

Synthesis of CTV7

Figure 7A:
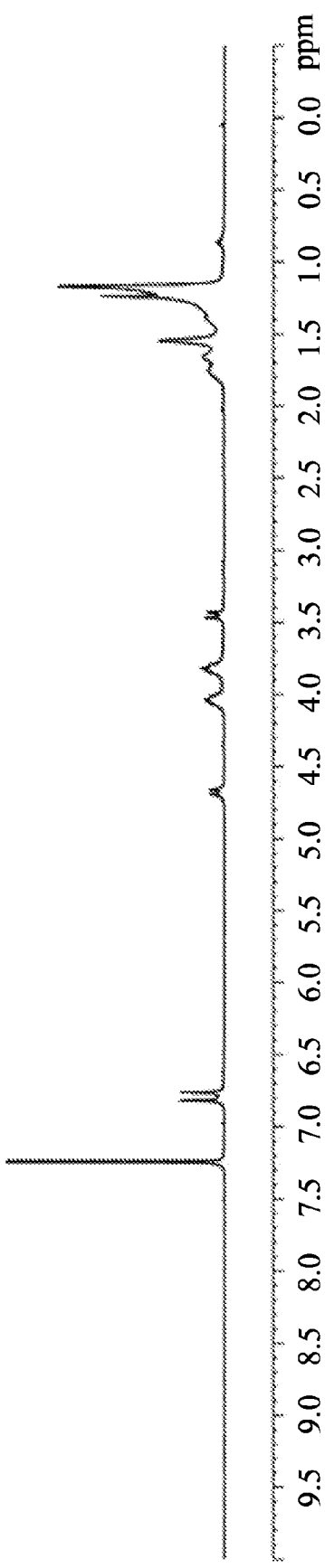
FIGS. 7A and 7B are $^1$H NMR and $^{13}$C NMR spectra of CTV7, respectively.
Figure 7B:
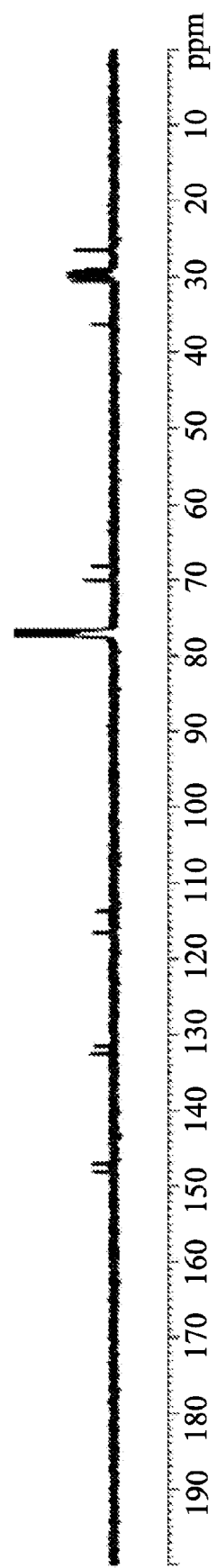

Following similar synthetic procedure described above for CTV2, a CHCl$_3$ (30 mL) solution of the corresponding triol (273 mg, 0.149 mmol) was added into a CHCl$_3$/CH$_3$NO$_2$ solution mixture (9/1; 200 mL) of TFA (18 mL) and stirred at room temperature for 60 h to afford CTV7 (43 mg, 16%). The $^1$H NMR and $^{13}$C NMR spectra of CTV7 are shown in FIGS. 7A and 7B, respectively. All related spectral data are listed below.

$^1$H NMR (400 MHz, CDCl$_3$, 298 K): δ=1.14-1.45 (m, 102H), 1.60-1.84 (m, 24H), 3.45 (d, J=13.8 Hz, 6H), 3.76-3.90 (m, 12H), 3.98-4.10 (m, 12H), 4.67 (d, J=13.6 Hz, 6H), 6.76 (s, 6H), 6.82 (s, 6H); $^{13}$C NMR (100 MHz, CDCl$_3$, 298 K): δ=26.4, 26.5, 29.1, 29.5, 29.7, 29.9, 30.1, 30.5, 30.5, 36.4, 68.2, 70.0 (one carbon signal was missing possibly because of signal overlap), 113.8, 116.5, 131.4, 132.5, 147.1, 148.1. HR-MS (ESI): calcd for $C_{117}H_{174}O_{12}^+$ [M]$^+$, m/z 1771.3005. found, m/z 1771.3946.

Synthesis of CTV8

Figure 8:
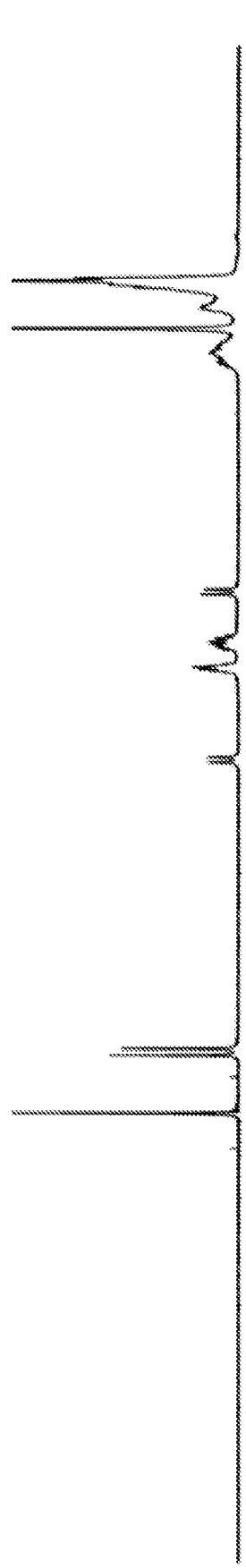
FIG. 8 is $^1$H NMR spectrum of CTV8.

Following similar synthetic procedure described above for CTV2, the reaction of the corresponding trialdehyde (157 mg, 843 μmol) and NaBH$_4$ (10 mg, 264 μmol) in isopropyl alcohol (5 mL) and CH$_2$Cl$_2$ (10 mL) at room temperature for 16 h afford a white solid. The white solid was then reacted with scandium triflate (44 mg, 894 μmol) in CHCl$_3$ (30 mL) at 60° C. for 3 days to afford CTV8 (22 mg, 14%). The $^1$H NMR spectrum of CTV8 is shown in FIG. 8. All related spectral data are listed below.

$^1$H NMR (400 MHz, CDCl$_3$, 298 K): δ=1.14-1.47 (m, 108H), 1.60-1.93 (m, 24H), 3.46 (d, J=14.0 Hz, 6H), 3.76-3.90 (m, 12H), 3.96-4.08 (m, 12H), 4.68 (d, J=13.6 Hz, 6H), 6.77 (s, 6H), 6.82 (s, 6H); HR-MS (ESI): calcd for $C_{120}H_{180}O_{12}$ [M], m/z 1813.3475. found, m/z 1813.3495.

Synthesis of CTV9

Figure 9:
FIG. 9 is $^1$H NMR spectrum of CTV9.

Following similar synthetic procedure described above for CTV2, the reaction of the corresponding trialdehyde (624 mg, 328 mol) and NaBH$_4$ (37 mg, 978 μmol) in isopropyl alcohol (10 mL) and CH$_2$Cl$_2$ (30 mL) at room temperature for 16 h afford a white solid. The white solid was then reacted with scandium triflate (176 mg, 358 μmol) in CHCl$_3$ (119 mL) at 60° C. for 3 days to afford CTV9 (27 mg, 4%). The $^1$H NMR spectrum of CTV9 is shown in FIG. 9. All related spectral data are listed below.

$^1$H NMR (400 MHz, CDCl$_3$, 298 K): δ=1.15-1.47 (m, 114H), 1.60-1.86 (m, 24H), 3.46 (d, J=13.6 Hz, 6H), 3.77-3.92 (m, 12H), 3.95-4.07 (m, 12H), 4.68 (d, J=13.6 Hz, 6H), 6.77 (s, 6H), 6.82 (s, 6H); HR-MS (ESI): calcd for $C_{123}H_{186}O_{12}$ [M]$^+$, m/z 1855.3944. found, m/z 1855.3911.

Synthesis of CTV10

Figure 10A:
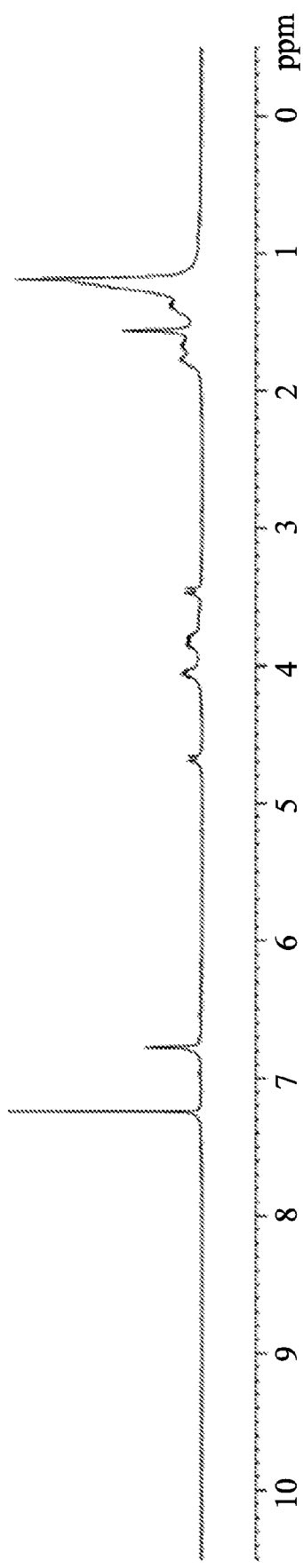
FIGS. 10A and 10B are $^1$H NMR and $^{13}$C NMR spectra of CTV10, respectively.
Figure 10B:
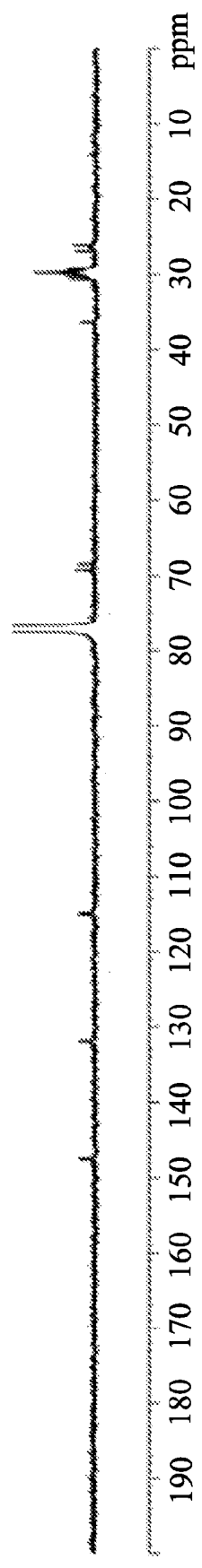

Following similar synthetic procedure described above for CTV2, the reaction of the corresponding trialdehyde (498 mg, 261 μmol) and NaBH$_4$ (30 mg, 0.793 mmol) in isopropyl alcohol (10 mL) and CH$_2$Cl$_2$ (20 mL) at room temperature for 16 h afforded a white solid. The white solid was then reacted with scandium triflate (86 mg, 175 μmol) in CHCl$_3$ (59 mL) at 60° C. for 3 days to afford CTV10 (15 mg, 3%). The $^1$H NMR and $^{13}$C NMR spectra of CTV10 are shown in FIGS. 10A and 10B, respectively. All related spectral data are listed below.

$^1$H NMR (400 MHz, CDCl$_3$, 298 K): δ=1.12-1.45 (m, 114H), 1.57-1.84 (m, 24H), 3.44 (d, J=13.6 Hz, 6H), 3.76-3.87 (m, 12H), 3.99-4.10 (m, 12H), 4.69 (d, J=13.6, 6H), 6.77 (s, 6H), 6.78 (s, 6H); $^{13}$C NMR (100 MHz, CDCl$_3$, 298 K): δ=26.1, 26.9, 29.2, 29.3, 29.6, 29.7, 29.9, 30.2, 30.6, 36.4, 68.6, 69.4, 114.8, 115.1, 132.0, 147.4, 147.6 (four signals were missing, possibly because of signal overlapping); HR-MS (ESI): calcd for $C_{120}H_{180}O_{12}$ [M]$^+$, m/z 1855.3944. found, m/z 1855.3902.

Synthesis of CTV11

Figure 11A:
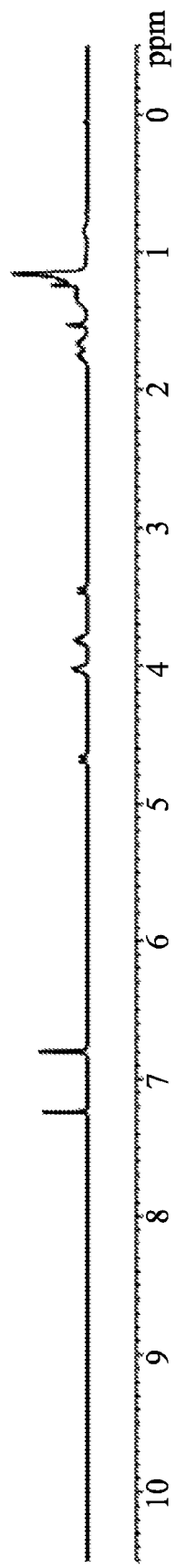
FIGS. 11A and 11B are $^1$H NMR and $^{13}$C NMR spectra of CTV11, respectively.
Figure 11B:
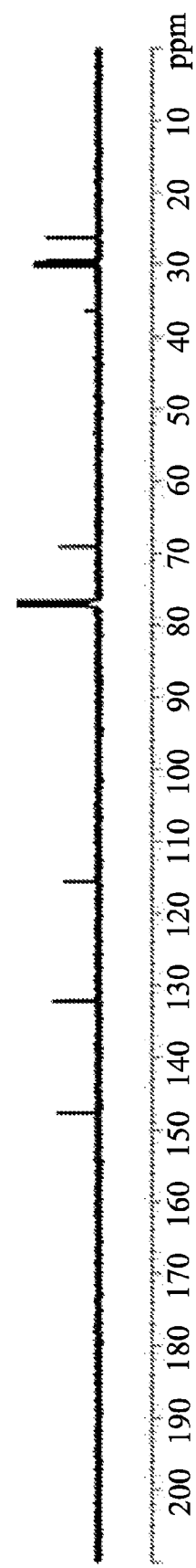

Following similar synthetic procedure described above for CTV1, the reaction of the corresponding triol (0.49 g, 0.3 mmol) and scandium triflate (0.3 g, 0.6 mmol) in CHCl$_3$ (250 mL) at 60° C. for 2 days to afford CTV11 (0.14 g, 30%). The $^1$H NMR and $^{13}$C NMR spectra of CTV11 are shown in FIGS. 11A and 11B, respectively. All related spectral data are listed below.

$^1$H NMR (400 MHz, CDCl$_3$, 298 K): δ=1.11-1.41 (m, 72H), 1.58-1.81 (m, 24H), 3.43 (d, J=13.8 Hz, 6H), 3.78-3.86 (m, 12H), 4.00-4.07 (m, 12H), 4.65 (d, J=13.8, 6H), 6.78 (s, 12H); $^{13}$C NMR (100 MHz, CDCl$_3$, 298 K): δ=26.1, 29.3, 29.6, 30.0, 36.3, 69.0, 115.8, 132.3, 147.4; HR-MS (ESI): calcd for $C_{102}H_{144}O_{12}Na^+$ [M+Na]$^+$, m/z 1584.0555. found, m/z 1584.0594.

Synthesis of CTV12

Figure 12A:
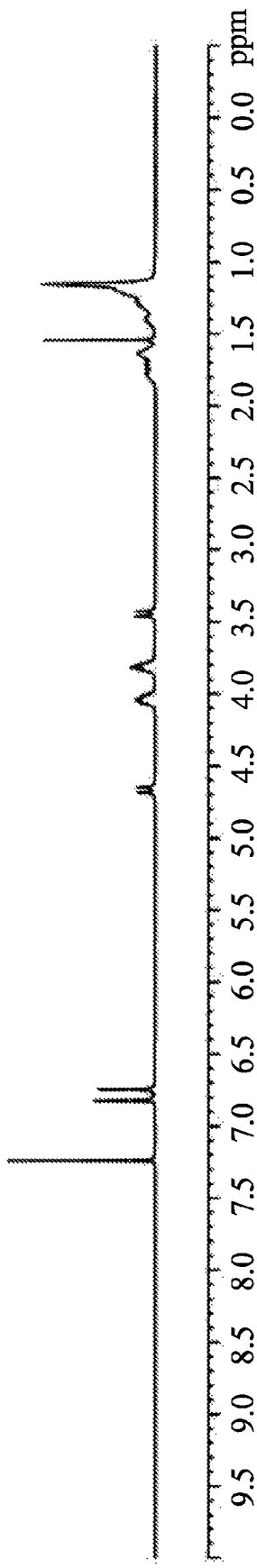
FIGS. 12A and 12B are $^1$H NMR and $^{13}$C NMR spectra of CTV12, respectively.
Figure 12B:
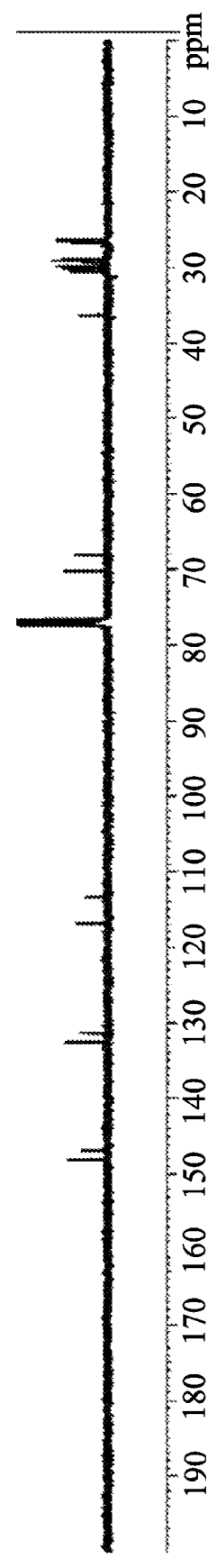

Following similar synthetic procedure described above for CTV2, the reaction of the corresponding triol (1.0608 g, 0.640 mmol) in CHCl$_3$ (50 mL) and TFA (64 mL) in CHCl$_3$/CH$_3$NO$_2$=4:1 (512/128 mL) was stirred at room temperature for 2 days to afford CTV12 (0.41 g, 40%). The $^1$H NMR and $^{13}$C NMR spectra of CTV12 are shown in FIGS. 12A and 12B, respectively. All related spectral data are listed below.

$^1$H NMR (400 MHz, CDCl$_3$, 298 K): δ=1.11-1.48 (m, 78H), 1.57-1.86 (m, 24H), 3.44 (d, J=13.6 Hz, 6H), 3.76-3.86 (m, 12H), 3.98-4.10 (m, 12H), 4.67 (d, J=13.6, 6H), 6.75 (s, 6H), 6.82 (s, 6H); $^{13}$C NMR (100 MHz, CDCl$_3$, 298 K): δ=26.4, 26.6, 29.0, 29.0, 29.3, 29.7, 29.9, 30.1, 30.5, 36.3, 68.0, 70.2, 113.4, 116.8, 131.3, 132.7, 146.8, 148.1; HR-MS (ESI): calcd for $C_{105}H_{150}O_{12}^+$ [M]$^+$, m/z 1603.1127. found, m/z 1603.1162.

Synthesis of Fullerene CTV Complexes

Fullerene CTV complexes, comprising fullerene⊙CTV hemicarceplexes, formed by various cyclotriveratrylene-based molecular cages, and various fullerene guests or derivatives thereof are disclosed below. Generally, fullerene⊙CTV complexes are formed by mixing a fullerene or a fullerene mixture with a CTV host in a less-polar solvent being capable of dissolving fullerene CTV complexes at or above room temperature, such as 25-80° C.

The meaning of "a complex" above is a supramolecular host-guest assembly, in which the fullerene guest is located inside the cavity of the CTV host. The meaning of "a hemicarceplex" above is a room temperature-isolatable complex. The meaning of "room temperature" is without heating at all. The meaning of "a fullerene" comprises an unmodified fullerene and a derivative thereof. The meaning of "a fullerene's derivative" comprises a fullerene molecule trapping an atom, an ion, a molecule or a metal cluster therein, such as Sc$_3$N@C$_{80}$.

Generally, the size of the inner space of the CTV host is strongly related to its shortest linking spacer(s). The size of the CTV host's openings may be adjusted by changing the length of its longer linking spacer(s). Thus, the selectivity of fullerene for entering the CTV host and its entering easiness may be controlled by adjusting the lengths of both linking spacers.

Formation of $C_{60}$ CTV1 Complex $C_{60}$ CTV1 complex was synthesized by mixing equimolar of the CTV1 and purified $C_{60}$ in $CDCl_2CDCl_2$.

Figure 13:
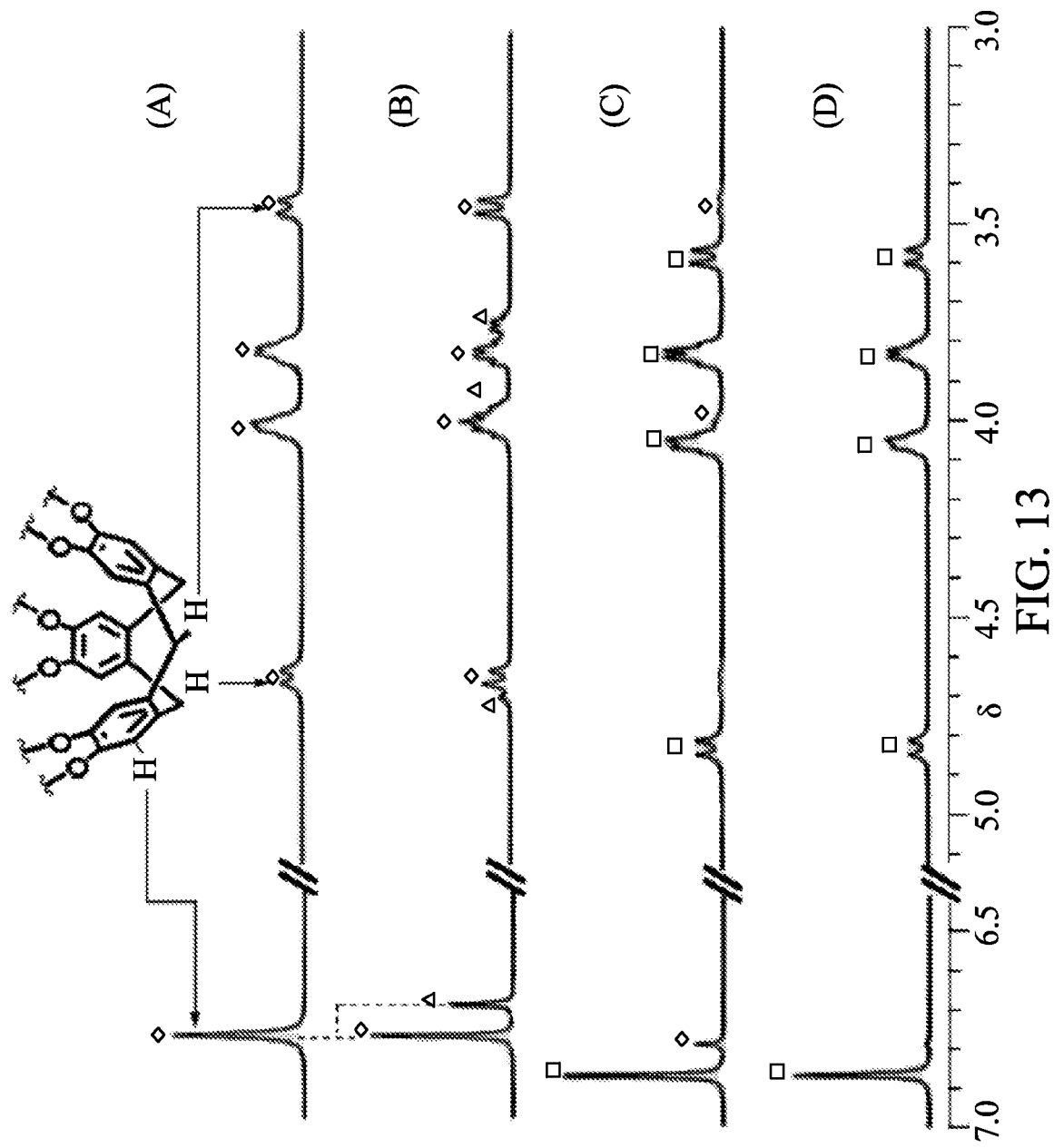
FIGS. 13(A), 13(B), 13(C), and 13(D) are $^1$H NMR spectrum (400 MHz, CDCl$_2$CDCl$_2$, 298 K) of CTV1, an equimolar mixture of $C_{60}$ and CTV1, an equimolar mixture of $C_{70}$ and CTV1, and purified $C_{70}$ CTV1 hemicarceplex, respectively.
Figure 14:
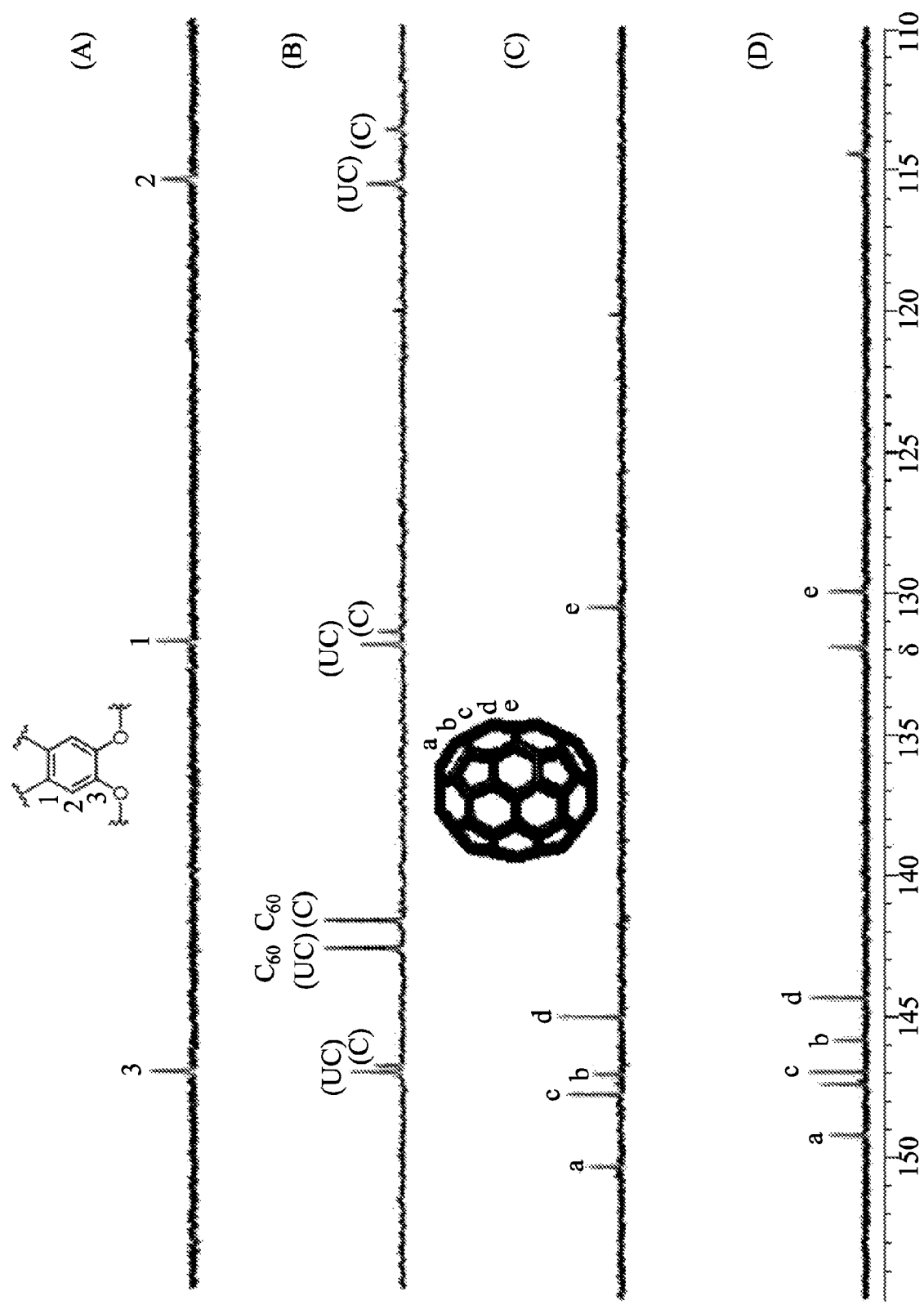
FIGS. 14(A), 14(B), 14(C), and 14(D) are $^{13}$C NMR spectrum (400 MHz, CDCl$_2$CDCl$_2$, 298 K) of CTV1, an equimolar mixture of $C_{60}$ and CTV1, purified $C_{70}$, and purified $C_{70}$ CTV1 hemicarceplex, respectively.

The $^1H$ NMR and $^{13}C$ NMR spectra of the equimolar mixture of $C_{60}$ and CTV1 are respectively shown in FIGS. 13B and 14B. In FIG. 13B, the descriptors (c) and (uc) respectively refer to the complexed and uncomplexed states of the corresponding components. For comparison, the $^1H$ NMR and $^{13}C$ NMR spectra of CTV1 are also respectively shown in FIGS. 13A and 14A.

In FIG. 13B, the $^1H$ NMR spectrum of the 3 mM equimolar mixture of $C_{60}$ and CTV1 shows a new set of signals corresponding to the $C_{60}$ CTV1 complex. Therefore, $C_{60}$ CTV1 complex was not sufficiently stable for isolation through column chromatography at ambient temperature, and thus cannot be called as hemicarceplex. However, the $^1H$ NMR spectrum of the equimolar mixture of $C_{60}$ and CTV1 suggests that the rates for $C_{60}$ guest entry into and exit from the internal cavity of CTV1 were slow on the timescale of $^1H$ NMR spectroscopy at 400 MHz.

In FIG. 14B, the $^{13}C$ NMR spectra of the 2.5 mM equimolar mixture of $C_{60}$ and CTV1 shows an upfield shifting of the signals of $C_{60}$ within $C_{60}$ CTV1 complex. This implied that the spherical fullerene could also be positioned favorably within the cavity of CTV1.

Synthesis of $C_{70}$ CTV1 Hemicarceplex $C_{70}$ CTV1 hemicarceplex was synthesized by the following steps. First, equimolar of the CTV1 and $C_{70}$ were mixed in $CDCl_2CDCl_2$. Then, the mixture was heated at 60° C. for 48 hours to form $C_{70}$ CTV1 hemicarceplex. The $^1H$ NMR spectrum of the 3 mM equimolar mixture of $C_{70}$ and CTV1 is shown in FIG. 13C.

Another solution of the CTV1 (40 mg, 23 μmol) and $C_{70}$ (19.4 mg, 23 μmol) in $CHCl_2CHCl_2$ (5 mL) was stirred at 60° C. for 24 hours and then the solvent was evaporated under reduced pressure. The residue was purified chromatographically ($SiO_2$; $CS_2$ then $CH_2Cl_2$/hexanes, 1:1 in volume ratio) to afford a black solid of $C_{70}$ CTV1 hemicarceplex (32 mg, 54%).

All related spectral data of the purified $C_{70}$ CTV1 hemicarceplex are provided below. Mp: >300° C.; $^1H$ NMR (400 MHz, $CDCl_2CDCl_2$, 298 K): δ=1.12-1.57 (m, 96H), 1.68-1.88 (m, 24H), 3.58 (d, J=13 Hz, 6H), 3.78-3.88 (m, 12H), 4.01-4.11 (m, 12H), 4.84 (d, J=13 Hz, 6H), 6.87 (s, 12H); $^{13}C$ NMR (100 MHz, $C_2D_2Cl_4$, 298 K): δ=26.8, 29.7, 29.9, 30.1, 30.2, 36.9, 68.7, 114.5, 130.0, 131.9, 144.3, 145.8, 147.0, 147.4, 149.2; HR-MS (ESI): calcd for $C_{184}H_{168}O_{12}^+$ [M]$^+$, m/z 2569.2536. found, m/z 2569.2704.

Accordingly, unlike complex $C_{60}$ CTV1, the $C_{70}$ CTV1 could be purified chromatographically, and thus may be called as a hemicarceplex. An electrospray ionization (ESI) mass spectrum of the purified $C_{70}$ CTV1 revealed intense peaks at m/z 2569.3 corresponding to the ions $[C_{70}$ CTV1]$^+$. The good matches between the observed and calculated isotope patterns for the ion support the successful synthesis of the hemicarceplex $C_{70}$ CTV1.

The $^1H$ NMR and $^{13}C$ NMR spectra of the purified $C_{70}$ CTV1 hemicarceplex is shown in FIGS. 13D and 14D. In FIG. 14D, the $^{13}C$ NMR spectrum of the isolated hemicarceplex $C_{70}$ CTV1 displays all five signals belonging to $C_{70}$, shifted upfield by 0.6-1.2 ppm relative to those of the free $C_{70}$ (FIG. 14C), suggesting encapsulation of spheroidal $C_{70}$ within the cavity of CTV1.

Figure 15A:
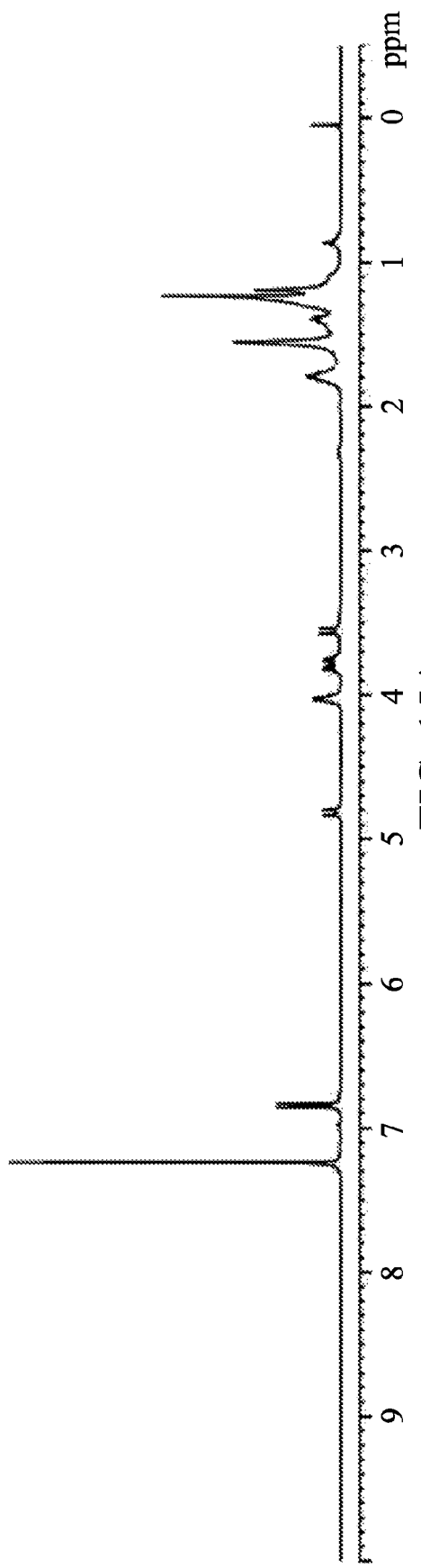
FIGS. 15A and 15B are $^1$H NMR (400 MHz, CDCl$_3$, 298 K) and $^{13}$C NMR (100 MHz, CDCl$_3$, 298 K) spectra of hemicarceplex $C_{70}$ CTV2, respectively.
Figure 15B:
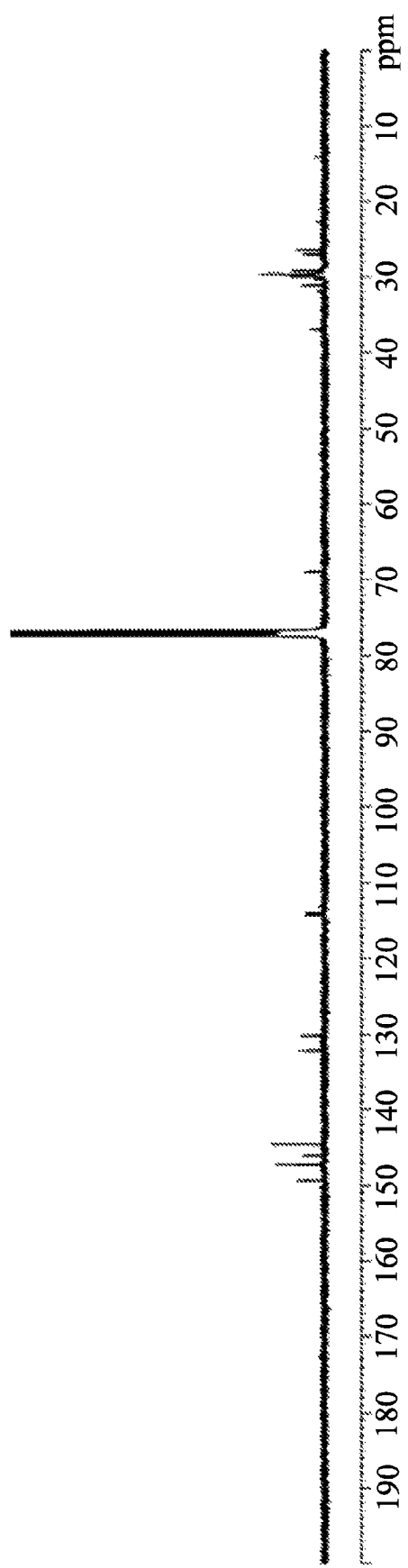

Synthesis of $C_{70}$⊙CTV2 Hemicarceplex $C_{70}$⊙CTV2 hemicarceplex was synthesized by the following steps. First, CTV2 (40 mg, 23.6 μmol) and $C_{70}$ (40 mg, 48 μmol) were mixed in $CHCl_2CHCl_2$ (2 mL) and stirred at 60° C. for 2 days. Then, the residue was purified chromatographically ($SiO_2$; $CS_2$ then $CH_2Cl_2$/hexanes, 4:1) to afford $C_{70}$⊙CTV2 hemicarceplex as a black solid (28.6 mg, 46%). The $^1H$ NMR and $^{13}C$ NMR spectra of the purified $C_{70}$⊙CTV2 hemicarceplex is shown in FIGS. 15A and 15B. An electrospray ionization (ESI) mass spectrum of the purified $C_{70}$⊙CTV2 revealed intense peaks at m/z 2528.2144 corresponding to the ions $[C_{70}$⊙CTV2+H]$^+$.

Comparing CTV1 and CTV2, since the carbon number of three alkyl chains between two cyclotriveratrylenes of CTV2 were decreased from 12 to 11, the size of the inner space and openings of CTV2 were both reduced, too. However, complex $C_{60}$⊙CTV2 still not stable enough to be chromatographically isolated in pure, thus, cannot be considered as a hemicarceplex. $C_{70}$⊙CTV1 and the $C_{70}$⊙CTV2 may be purified chromatographically, and thus may be called as hemicarceplex.

All related spectral data of the purified $C_{70}$ CTV2 hemicarceplex are provided below. Mp: >300° C. (dec.); $^1H$ NMR (400 MHz, $CDCl_3$, 298 K): δ=1.12-1.50 (m, 90H), 1.72-1.88 (m, 26H), 3.56 (d, J=13.6 Hz, 6H), 3.71-3.85 (m, 12H), 3.99-4.07 (m, 12H), 4.84 (d, J=13.6 Hz, 6H), 6.83 (s, 6H), 6.86 (s, 6H); $^{13}C$ NMR (100 MHz, $CDCl_3$, 298 K): δ=26.4, 27.0, 29.2, 29.7, 29.8, 29.9, 30.0, 30.1, 30.4, 31.1, 37.0, 68.8, 68.9, 113.9, 114.3, 130.2, 132.1, 132.2, 144.6, 146.1, 147.2, 147.3, 147.4, 149.4; HR-MS (ESI): calcd for $C_{184}H_{168}O_{12}^+$ [M+H]$^+$, m/z 2528.2066 found, m/z 2528.2144.

Figure 16A:
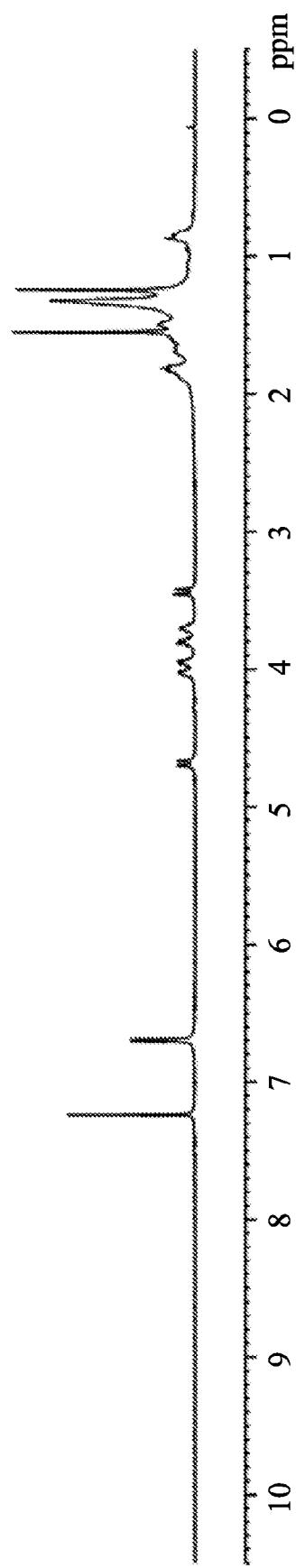
FIGS. 16A and 16B are $^1$H NMR (400 MHz, CDCl$_3$, 298 K) and $^{13}$C NMR (200 MHz, CDCl$_3$, 298 K) spectra of hemicarceplex $C_{60}$ CTV3, respectively.
Figure 16B:
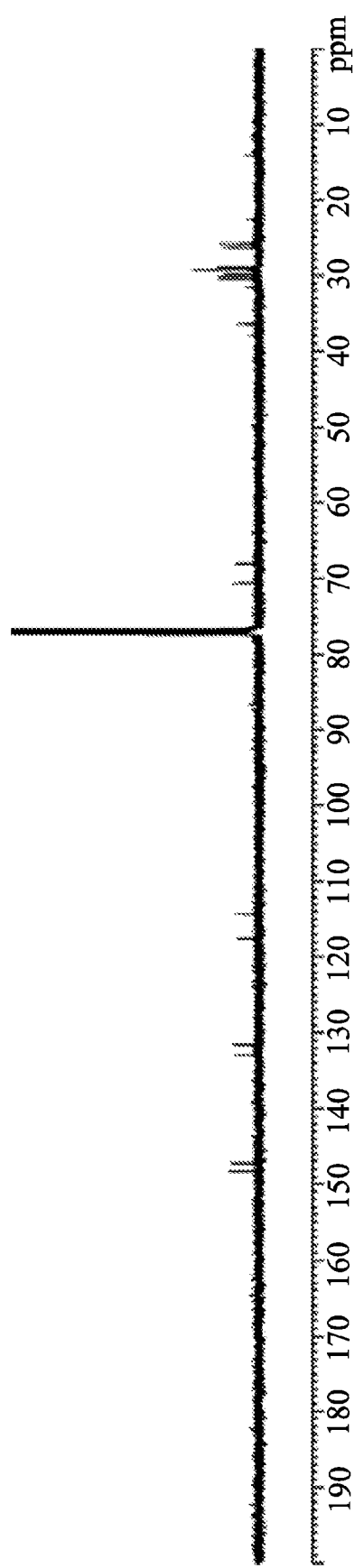

Synthesis of $C_{60}$⊙CTV3 Hemicarceplex $C_{60}$⊙CTV3 hemicarceplex was synthesized by the following steps. First, CTV3 (10 mg, 6.07 μmol) and $C_{60}$ (10 mg, 13.9 μmol) were mixed in $CHCl_2CHCl_2$ (2 mL) and stirred at 50° C. for 20 h. Then, the residue was purified chromatographically ($SiO_2$; $CS_2$ then $CH_2Cl_2$/hexanes, 4:1) to afford $C_{60}$⊙CTV3 hemicarceplex as a black solid (4.3 mg, 30%). The $^1H$ NMR and $^{13}C$ NMR spectra of the purified $C_{60}$⊙CTV3 hemicarceplex are shown in FIGS. 16A and 16B.

Comparing CTV2 and CTV3, since the carbon number of three alkyl chains between two cyclotriveratrylenes of CTV3 were further decreased from 11 to 10, the size of the inner space and openings of CTV3 was further reduced, too. Thus, it appeared that the more sizable $C_{70}$ is not capable to enter the cavity of CTV3 but the smaller $C_{60}$ can form stable hemicarceplex $C_{60}$⊙CTV3 with CTV3.

All related spectral data of the purified $C_{60}$ CTV3 hemicarceplex are provided below. $^1H$ NMR (400 MHz, $CDCl_3$, 298 K): δ=1.29-1.53 (m, 84H), 1.77-1.93 (m, 24H), 3.44 (d, J=13.6 Hz, 6H), 3.66-3.86 (m, 12H), 3.91-4.07 (m, 12H), 4.69 (d, J=14 Hz, 6H), 6.69 (s, 6H), 6.71 (s, 6H); $^{13}C$ NMR (200 MHz, $CDCl_3$, 298 K): δ=25.8, 27.0, 28.3, 28.8, 29.1, 29.2, 30.1, 30.8, 31.0, 37.0, 68.7, 68.8, 114.1, 114.2, 131.9, 132.0, 142.1, 147.3, 147.4; HR-MS (ESI): calcd for $C_{168}H_{156}O_{12}^+$ [M]$^+$, m/z 2365.1597 found, m/z 2365.1649.

As $C_{70}$ CTV1 and $C_{70}$ CTV2, $C_{60}$ CTV3 could also be purified chromatographically, and thus may be called as hemicarceplex. An electrospray ionization (ESI) mass spectrum of the purified $C_{60}$ CTV3 revealed intense peaks at m/z 2365.1649 corresponding to the ions $[C_{60}$ CTV3]$^+$.

Figure 17:
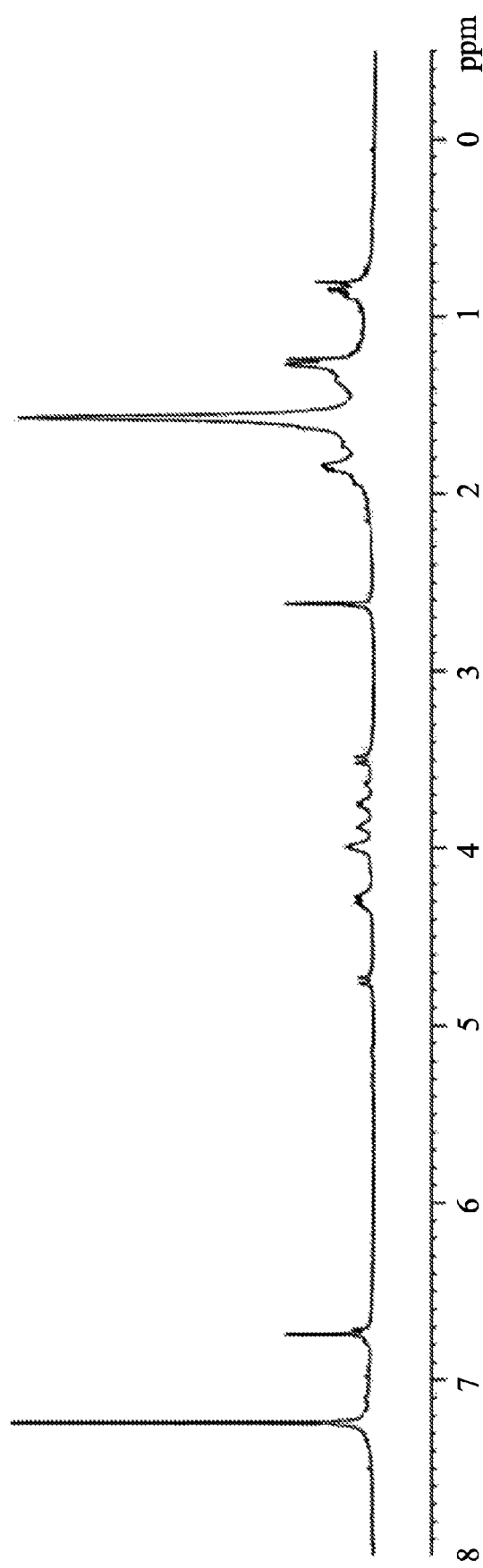
FIG. 17 is the $^1$H NMR (400 MHz, CDCl$_3$, 298 K) spectrum of hemicarceplex Sc3N@C$_{80}$ CTV4.

Synthesis of $Sc_3N@C_{80}$⊙CTV4 Hemicarceplex $Sc_3N@C_{80}$⊙CTV4 hemicarceplex was synthesized by the following steps. First, equimolar of the CTV4 and $Sc_3N@C_{80}$ were mixed in $CDCl_2CDCl_2$ to form an equimolar mixture (6 mM). Then, the mixture stirred at room temperature for 20 hours to form $Sc_3N@C_{80}$⊙CTV4 hemicarceplex. The $^1H$ NMR spectrum of the purified $Sc_3N@C_{80}\odot CTV4$ hemicarceplex is shown in FIG. 17. An electrospray ionization (ESI) mass spectrum of the purified $Sc_3N@C_{80}\odot CTV4$ revealed intense peaks at m/z 3020.1055 corresponding to the ions $[Sc_3N@C_{80}\odot CTV4+H]^+$.

All related spectral data of the purified $Sc_3N@C_{80}\odot CTV4$ hemicarceplex are provided below. $^1H$ NMR (400 MHz, $CDCl_3$, 298 K): δ=1.11-1.45 (m, 42H), 1.77-2.07 (m, 42H), 2.62 (s, 12H), 3.50 (d, J=13.6 Hz, 6H), 3.71-3.80 (m, 6H), 3.84-3.91 (m, 6H), 3.96-4.04 (m, 12H), 4.23-4.36 (m, 12H), 4.74 (d, J=13.2, 6H), 6.74 (s, 12H); HR-MS (ESI): calcd for $C_{194}H_{157}NO_{24}Sc_3$ $[M+H]^+$, m/z 3020.1745. found, m/z 3020.1055.

The Formation of $C_{60}\odot CTV5$ and $C_{70}\odot CTV5$ Complexes $C_{60}\odot CTV5$ and $C_{70}\odot CTV5$ complexes were synthesized by mixing equimolar of the CTV5 and purified $C_{60}$ and $C_{70}$ in $CDCl_2CDCl_2$, respectively.

The $^1H$ NMR spectra of the equimolar mixture of CTV5 to $C_{60}$ and $C_{70}$ are respectively shown in FIGS. 18A and 18B. In FIGS. 18A and 18B, the descriptors (c) and (uc) respectively refer to the complexed and uncomplexed states of the corresponding components.

Comparing CTV2 and CTV5, the atom numbers of the three alkyl chains between two cyclotriveratrylenes were the same (11 atoms), but the atom numbers of the other three chains were increase from 12 to 14, the size of the openings of the CTV5 was increased. Therefore, $C_{60}$ and $C_{70}$ could both enter the inner space of the CTV5 but the complexes formed are not stable enough to be isolated through column chromatography and cannot be called as hemicarceplexes.

Figure 19:
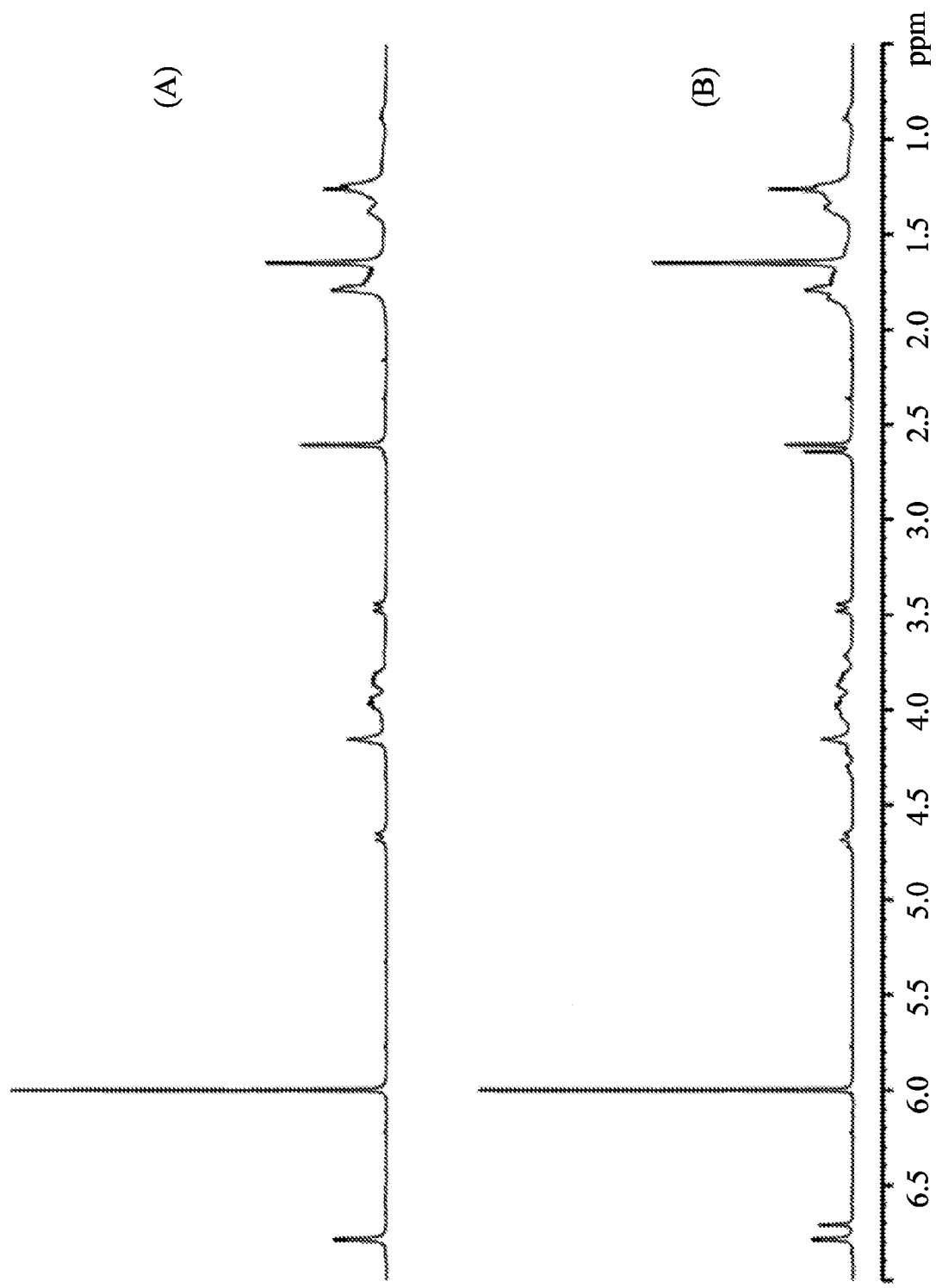
FIGS. 19(A) and 19(B) are the $^1$H NMR (400 MHz, CDCl$_3$, 298 K) spectra of free CTV6, and the equimolar mixture of CTV6 and C$_{60}$, respectively.

The Formation of $C_{60}\odot CTV6$ Complexes $C_{60}\odot CTV6$ complexes were synthesized by mixing equimolar of the CTV6 and $C_{60}$ in $CDCl_2CDCl_2$. The $^1H$ NMR spectra of the equimolar mixture of CTV6 and $C_{60}$ are shown in FIG. 19B. For comparison, the $^1H$ NMR spectrum of CTV6 is also shown in FIG. 19A.

In FIG. 19B, the $^1H$ NMR spectrum of the 4 mM equimolar mixture of $C_{60}$ and CTV6 shows a new set of signals corresponding to the $C_{60}$ CTV6 complex.

Comparing CTV6 and CTV5, the atom numbers of the three alkyl chains between two cyclotriveratrylenes were decreased from 11 to 10, but the atom numbers of the other three chains remains the same (14 atoms), the size of the molecular openings of the CTV6 was, thus, reduced. Therefore, $C_{60}$ but not C70 could enter the inner space of the CTV6, however, the complexes formed are not stable enough to be isolated through column chromatography.

Figure 20:
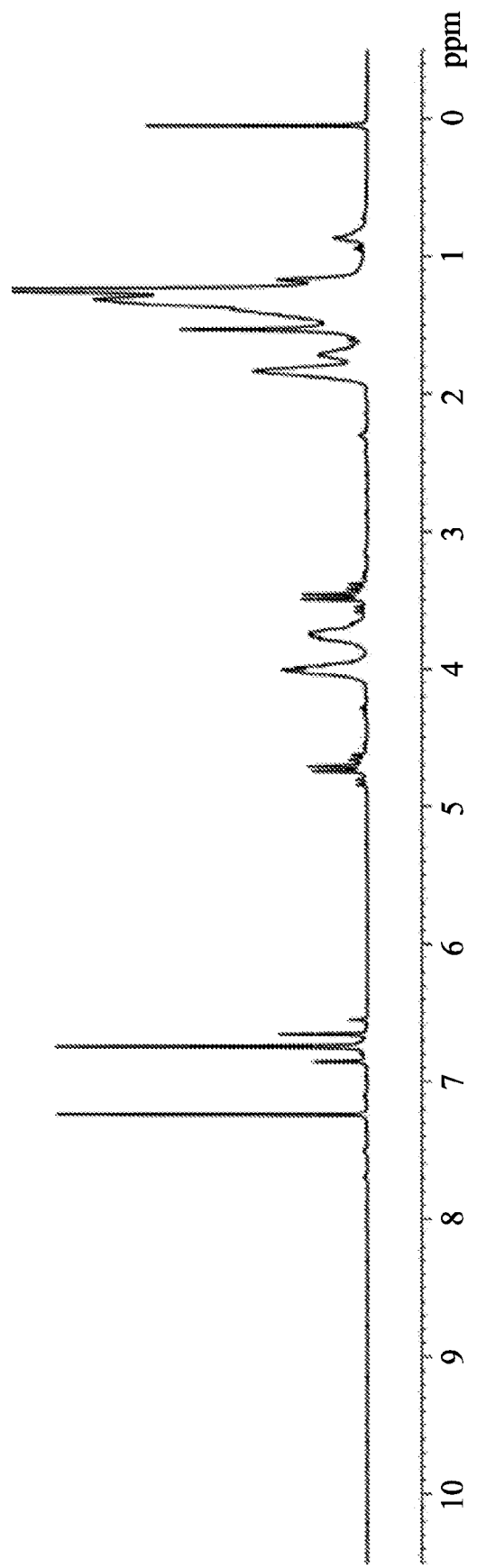
FIG. 20 is $^1$H NMR spectra of the purified C$_{76}$⊙CTV7 and C$_{78}$⊙CTV7 hemicarceplexes.

Synthesis of $C_{76}\odot CTV7$ and $C_{78}\odot CTV7$ Hemicarceplexes $C_{76}\odot CTV7$ and $C_{78}\odot CTV7$ hemicarceplexes were synthesized by the following steps. First, CTV7 (510 mg, 288 mmol) and high-order fullerene mixture (680 mg) were mixed in $CHCl_2CHCl_2$ (34 mL) and stirred at 35° C. for 40 h. Then, the residue was purified chromatographically ($SiO_2$; $CS_2$ then $CH_2Cl_2$/hexanes, 4:1) to afford $C_{76}\odot CTV7$ and $C_{78}$®CTV7 hemicarceplexes as a black solid (361 mg). The $^1H$ NMR spectra of the purified $C_{76}\odot CTV7$ and $C_{78}$®CTV7 hemicarceplex is shown in FIG. 20.

HR-MS of $C_{76}\odot CTV7$ (ESI): calcd for $C_{193}H_{175}O_{12}^+$ $[M+H]^+$, m/z 2684.3084. found, m/z 2684.3147. HR-MS of $C_{78}\odot CTV7$ (ESI): calcd for $C_{195}H_{175}O_{12}^+$ $[M+H]^+$, m/z 2708.3084. found, m/z 2708.3198.

Figure 21:
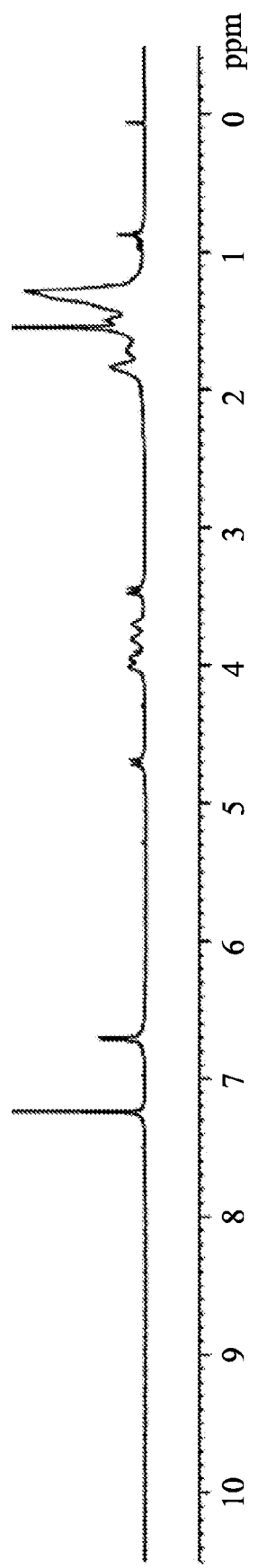
FIG. 21 is $^1$H NMR of the purified CO$_{84}$⊙CTV8 hemicarceplex.

Synthesis of $C_{84}\odot CTV8$ Hemicarceplex $C_{84}\odot CTV8$ hemicarceplex was synthesized by the following steps. First, CTV8 (243 mg, 134 mmol) and high-order fullerene mixture obtained from previous $C_{76}$ and $C_{78}$ extraction (243 mg) were mixed in $CHCl_2CHCl_2$ (45 mL) and stirred at 30° C. for 16 h. Then, the residue was purified chromatographically ($SiO_2$; $CS_2$ then $CH_2Cl_2$/hexanes, 4:1) to afford $C_{84}\odot CTV8$ hemicarceplex as a black solid (112 mg). The $^1H$ NMR of the purified $C_{84}\odot CTV8$ hemicarceplex is shown in FIG. 21. HR-MS of $C_{84}\odot CTV8$ (ESI): calcd for $C_{204}H_{180}O_{12}^+$ $[M]^+$, m/z 2821.3475. found, m/z 2821.3499.

Synthesis of fullerenes⊙CTV9 Complexes

Figure 22:
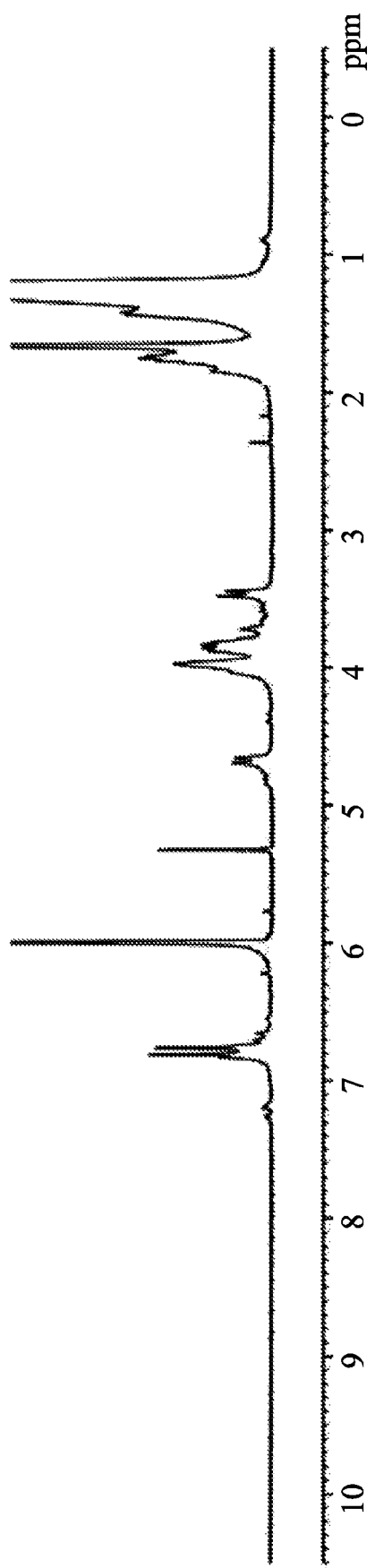
FIG. 22 is $^1$H NMR spectrum fullerenes⊙CTV9 complexes.

Fullerenes⊙CTV9 complexes were formed by mixing CTV9 (3 mg) and higher-order fullerene extract (3 mg) in $CDCl_2CDCl_2$ (0.5 mL) at room temperature. The appearance of several new set of signals for the complexed host CTV9 in the $^1H$ NMR spectrum in FIG. 22 similar to the ones observed in the case of the above fullerene-complexed CTV hosts, suggested the formation of the fullerenes⊙CTV9 complex under this condition.

Figure 23:
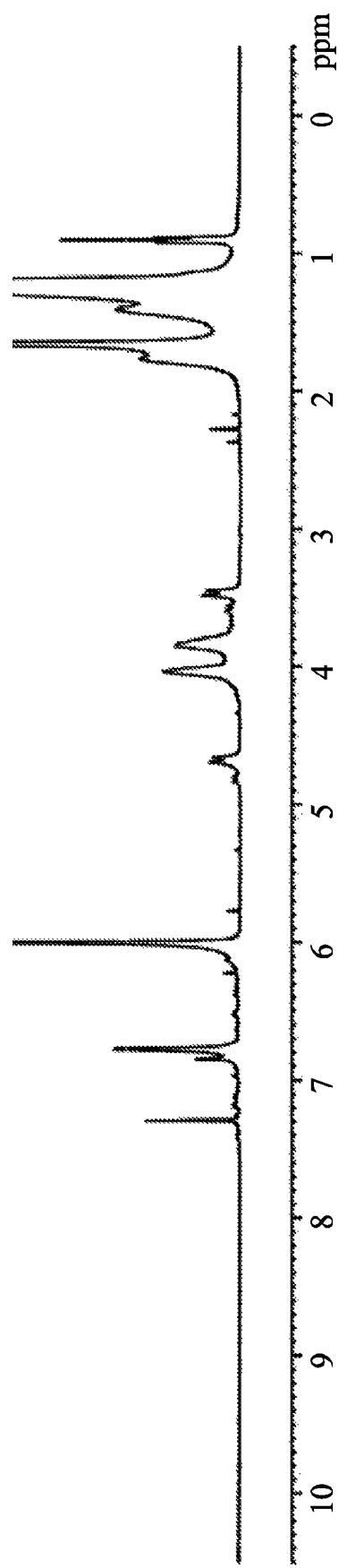
FIG. 23 is $^1$H NMR spectrum fullerenes⊙CTV10 complexes.

Synthesis of $C_{70}\odot CTV10$ Complex $C_{70}\odot CTV10$ complex was formed by mixing CTV10 (2.8 mg) and $C_{70}$ (1.2 mg) in $CDCl_2CDCl_2$ (0.4 mL) at room temperature. The appearance of a new set of signals for the complexed host CTV10 in the $^1H$ NMR spectrum in FIG. 23 similar to the ones observed in the case of the above fullerene-complexed CTV hosts, suggested the formation of the $C_{70}\odot CTV10$ complex under this condition.

Figure 24A:
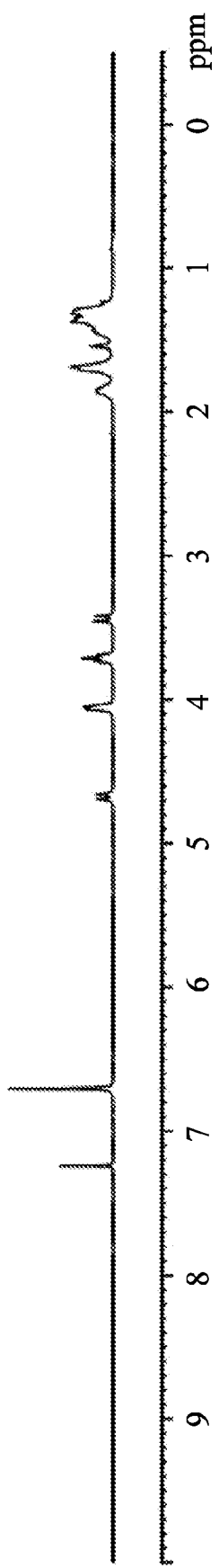
FIGS. 24A and 24B are $^1$H NMR and $^{13}$C NMR spectra of the purified C$_{60}$⊙CTV11 hemicarceplex, respectively.
Figure 24B:

Synthesis of $C_{60}\odot CTV11$ Hemicarceplex $C_{60}\odot CTV11$ hemicarceplex was synthesized by the following steps. First, CTV11 (40 mg, 26 μmol) and $C_{60}$ (40 mg, 56 μmol) was ball-milled at room temperature for 1 h and the solid residue was heated under vacuum at 250° C. for 15 h. The resulting solid was purified chromatographically ($SiO_2$; $CS_2$ then $CH_2Cl_2$/hexane, 4:1) to afford $C_{60}\odot CTV11$ as a brown solid (22 mg, 38%). The $^1H$ NMR and $^{13}C$ NMR spectra of the purified $C_{60}\odot CTV11$ hemicarceplex are shown in FIGS. 24A and 24B, respectively. All related spectral data are listed below.

$^1H$ NMR (400 MHz, $CDCl_3$, 298 K): δ=1.20-1.50 (m, 60H), 1.60-1.79 (m, 24H), 1.80-1.91 (m, 12H), 3.44 (d, J=13.6 Hz, 6H), 3.66-3.75 (m, 12H), 4.05-4.07 (m, 12H), 4.68 (d, J=13.6 Hz, 6H), 6.70 (s, 12H); $^{13}C$ NMR (100 MHz, $CDCl_3$, 298 K): δ=27.2, 30.2, 30.8, 30.9, 37.1, 68.6, 114.9, 132.1, 142.0, 147.7; HR-MS (ESI): calcd for $C_{162}H_{144}O_{12}^+$ $[M]^+$, m/z 2281.0658. found, m/z 2281.0689.

Figure 25A:
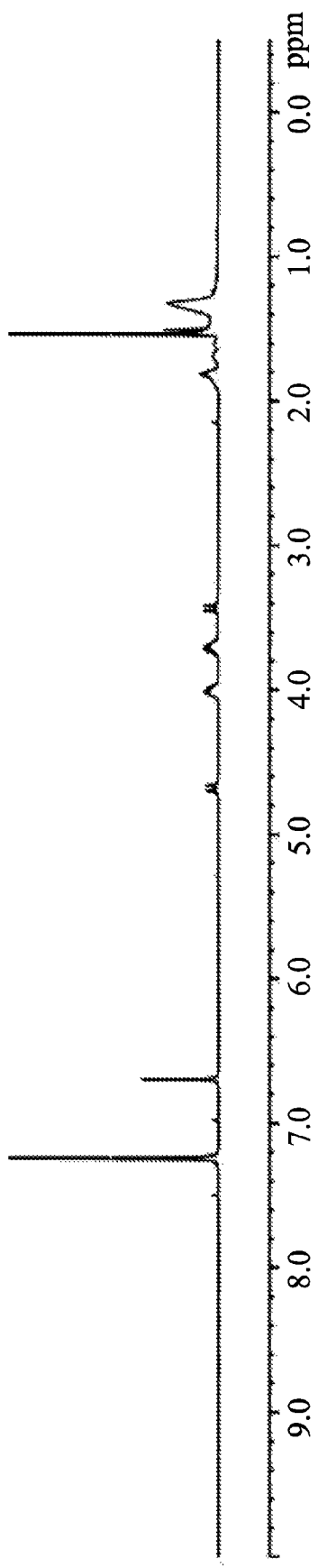
FIGS. 25A and 25B are $^1$H NMR and $^{13}$C NMR spectra of the purified C$_{60}$⊙CTV12 hemicarceplex, respectively.
Figure 25B:
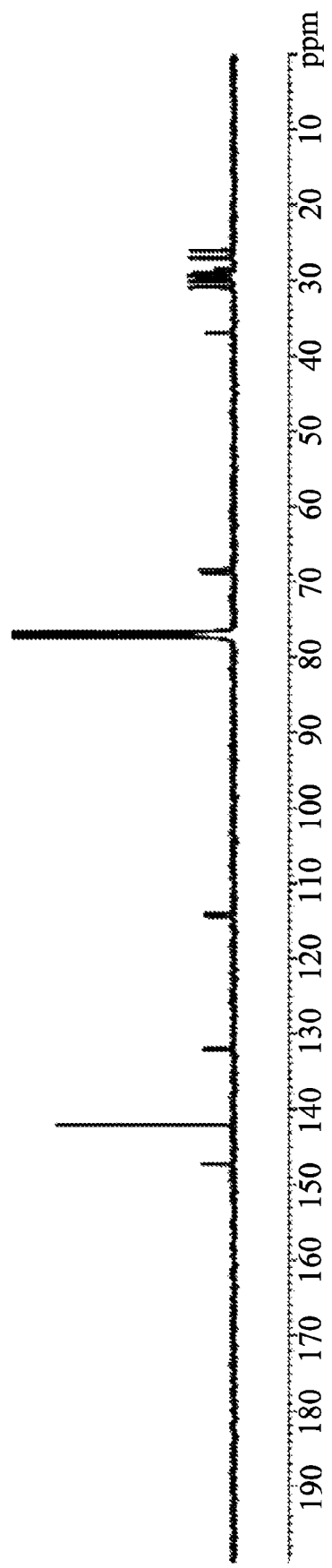

Synthesis of $C_{60}\odot CTV12$ Hemicarceplex $C_{60}\odot CTV12$ hemicarceplex was synthesized by the following steps. First, CTV12 (30 mg, 19 μmole) and $C_{60}$ (50 mg, 0.069 mmole) was ball-milled at room temperature for 1 h and the solid residue was heated under vacuum at 240° C. for 12 h. The resulting solid was purified chromatographically ($SiO_2$; $CS_2$ then $CH_2Cl_2$/hexane, 4:1) to afford $C_{60}\odot CTV12$ as a brown solid (27 mg, 61%). The $^1H$ NMR and $^{13}C$ NMR spectra of the purified $C_{60}\odot CTV12$ hemicarceplex are shown in FIGS. 25A and 25B, respectively. All related spectral data are listed below.

$^1H$ NMR (400 MHz, $CDCl_3$, 298 K): δ=1.28-1.52 (m, 78H), 1.57-1.93 (m, 24H), 3.43 (d, J=13.6 Hz, 6H), 3.65-3.77 (m, 12H), 3.95-4.08 (m, 12H), 4.68 (d, J=13.6, 6H), 6.70 (s, 12H); $^{13}C$ NMR (100 MHz, $CDCl_3$, 298 K): δ=26.0, 26.9, 28.4, 29.0, 29.3, 29.6, 30.0, 30.8, 30.9, 37.0, 68.3, 68.8, 114.0, 114.4, 131.8, 132.0, 142.1, 147.3, 147.4; HR-MS (ESI): calcd for $C_{165}H_{150}O_{12}Na^+$ $[M+Na]^+$, m/z 2346.1020. found, m/z 2346.0946.

Kinetic Data of $C_{60}$ CTV1 and $C_{70}$ CTV1

Complexation of the CTV1 with $C_{60}$

Experiments were performed in $CDCl_2CDCl_2$ using an equimolar (3 mM) mixture of the CTV1 and $C_{60}$ at 25° C.

In this experiment, a simplified second-order rate equation (1) shown below was used to calculate an association rate constant ($k_a$) of forming $C_{60}$ CTV1 complex at the early stage of complexation.

$$k_a = (1/[A_t] - 1/[A_0])/t = \{1/([A_0] - [P_t]) - 1/[A_0]\}/t \quad (1)$$

The initial concentration of free CTV, $[A_0]$, and the free $C_{60}$, $[B_0]$, were both 3 mM. $[A_t]$ is the concentration of the free CTV1 at time t, and $[P_t]$ is the concentration of the $C_{60}$ CTV1 complex at time t. $[A_t]$ and $[P_t]$ were determined based on the integration values of the signals at δ 6.80 ($H_p$, s, 12H) and δ 6.70 ($H_{p'}$, s, 12H), respectively. $[A_t]$ could also be determined based on $[A_0] - [P_t]$. Accordingly, based on a plot of $1/[A_t] - 1/[A_0]$ against t (s) at 298 K, the association rate constant ($k_a$) was obtained by calculating the slope of the plot. The obtained association rate constant ($k_a$) was $1.68 \times 10^{-1}$ $M^{-1} s^{-1}$.

The half-life time of the complexation reaction ($t_{1/2}$) was given by equation (2) below. The calculated half-life time of the complexation reaction ($t_{1/2}$) was 33.1 min.

$$t_{1/2} = 1/(k_a[A_0]) \quad (2)$$

The value of $\Delta G^{\ddagger}$ (kcal mol$^{-1}$) was calculated using the relationship shown in equation (3) below, where R, h, and $k_B$ are the gas, Planck, and Boltzmann constants, respectively. The calculated $\Delta G^{\ddagger}$ was 18.49 kcal mol$^{-1}$.

$$\Delta G^{\ddagger} = -RT \ln(kh/k_B T) \quad (3)$$

The equilibrium constant ($K_a$) of forming $C_{60}$ CTV1 complex at 25° C. was also determined. $^1$H NMR spectrum (400 MHz, CDCl$_2$CDCl$_2$, 298 K) of an equimolar ($C_M$=3 mM) mixture of $C_{60}$ and the CTV1 after heating at 298 K for 7 days was used to determine the equilibrium constant ($K_a$) of forming $C_{60}$ CTV1 complex. The integration values for the signals of the free ($I_f$, 6.8 ppm) and complexed ($I_c$, 6.7 ppm) species are 1.016 and 0.843, respectively. Therefore, the equilibrium constant ($K_a$) of forming $C_{60}$ CTV1 complex was determined by using equation (4) below to be 506 M$^{-1}$.

$$K_a = I_c(I_f + I_c)/(I_f^2 C_M) \quad (4)$$

Dissociation of the Hemicarceplex $C_{70}$ CTV1

The dissociation experiments were performed using constant concentrations of the hemicarceplex $C_{70}$ CTV1 (3 mM) in CDCl$_2$CDCl$_2$, d8-toluene, CDCl$_3$, CDCl$_3$/CD$_3$CN (95:5 and 90:10 in volume ratio), and CDCl$_3$/CD$_3$NO$_2$ (95:5 and 90:10 in volume ratio). $^1$H NMR spectra were recorded at regular intervals during the experiment. Because of the poor solubility of the CTV1 in toluene, trichloroethene was added as an internal standard to determine the concentration of the hemicarceplex during the dissociation.

The reverse reaction may be ignored during the early stages of the first-order decomplexation event. Therefore, using the first-order rate law shown in equation (5) below, the dissociation rate constants ($k_d$) were determined at the early stages of decomplexation from the slopes of the straight lines in the plots of $\ln([A_0]/[A_t])$ against t (s) at 25° C. The concentration of the $C_{70}$ CTV1 hemicarceplex, $[P_t]$, was determined from the integration of signals at ca. δ 6.90 ($H_p$, s, 12H).

$$k_d = \ln([P_0]/[P_t])/t \quad (5)$$

The half-life time of the decomplexation reaction ($t_{1/2}$) was given by equation (6) below.

$$t_{1/2} = \ln(2/k_d) \quad (6)$$

The values of $\Delta G^{\ddagger}$ (kcal mol$^{-1}$) were also calculated using the relationship shown in equation (3).

The obtained dissociation rate constants ($k_d$), $\Delta G^{\ddagger}$, and $t_{1/2}$ are listed in Table 1 below. From the dissociation rate constants ($k_d$) listed in Table 1, it may be known that the dissociation rate constant was decreased as the polarity of the solvent system was increased from CDCl$_2$CDCl$_2$ to CDCl$_3$/CD$_3$CN (90:10). This is because of the lipophilicity of $C_{70}$, which make the dissociation state of the hemicarceplex $C_{70}$ CTV1 to be more unstable.

TABLE 1

The obtained dissociation rate constants ($k_d$), $\Delta G^{\ddagger}$, and $t_{1/2}$ for the hemicarceplex $C_{70}$ CTV1 dissociated in various solvent system.

| Solvent | $k_d$ (s$^{-1}$) | $t_{1/2}$ (h) | $\Delta G^{\ddagger}$ (kcal mol$^{-1}$) |
|---|---|---|---|
| d8-toluene | $6.5 \pm 0.7 \times 10^{-5}$ | $3.0 \pm 0.3$ | $23.2 \pm 0.1$ |
| CDCl$_2$CDCl$_2$ | $6.3 \pm 0.7 \times 10^{-6}$ | $30.6 \pm 3.3$ | $24.6 \pm 0.1$ |
| CDCl$_3$ | $5.1 \pm 0.5 \times 10^{-6}$ | $37.8 \pm 3.3$ | $24.7 \pm 0.1$ |
| CDCl$_3$/CD$_3$NO$_2$ (95:5) | $5.0 \pm 0.5 \times 10^{-6}$ | $38.5 \pm 3.8$ | $247.8 \pm 0.1$ |
| CDCl$_3$/CD$_3$CN (95:5) | $4.3 \pm 0.4 \times 10^{-6}$ | $44.8 \pm 4.0$ | $24.7 \pm 0.1$ |
| CDCl$_3$/CD$_3$NO$_2$ (90:10) | $3.6 \pm 0.3 \times 10^{-6}$ | $53.5 \pm 4.0$ | $25.0 \pm 0.1$ |
| CDCl$_3$/CD$_3$CN (90:10) | $3.2 \pm 0.3 \times 10^{-6}$ | $60.2 \pm 4.9$ | $24.9 \pm 0.1$ |

Similarly, the relatively rapid dissociation of the hemicarceplex $C_{70}$ CTV1 in toluene-d$_8$ was because of $C_{70}$ stabilized more in the dissociated state than in the complex. Moreover, because of the poor solubility of the CTV1 in toluene-d$_8$, a white solid precipitated from the red solution during dissociation of the hemicarceplex $C_{70}$ CTV1 in this solvent. Correspondingly, the $^1$H NMR spectra revealed a gradual decrease in the intensity of signals belonging to the hemicarceplex, but without the appearance of any signals for the free CTV1. Accordingly, the relatively rapid dissociation rate and the precipitation of the free CTV1 from the red solution of the hemicarceplex $C_{70}$ CTV1 in toluene-d$_8$ suggested that toluene would be a good choice of solvent for dissociating the hemicarceplex into its free components on a practical scale.

The equilibrium constant ($K_a$) of forming $C_{70}$ CTV1 complex at 25° C. was also determined. $^1$H NMR spectrum (400 MHz, CDCl$_2$CDCl$_2$, 298 K) of the mixture obtained from the decomplexation of $C_{70}$⊙CTV1 ($C_M$=3 mM) at 298 K after 10 days was used to determine equilibrium constant ($K_a$) of forming $C_{70}$ CTV1 complex. The integration values for the signals of the free ($I_f$, 6.8 ppm) and complexed ($I_c$, 6.9 ppm) species are 0.324 and 1.000, respectively. Therefore, the equilibrium constant ($K_a$) of forming $C_{70}$ CTV1 complex was determined by using equation (4) above to be 4204 M$^{-1}$. In addition, the association rate constant ($k_a$) was determined to be 0.026 M$^{-1}$ s$^{-1}$. The determination methods were similar to the methods mentioned for the $C_{60}$ CTV1 complex above, and hence omitted here.

The Release of the Fullerenes Incarcerated in $C_{76}$⊙CTV7 and $C_{78}$⊙CTV7 Hemicarceplexes The $C_{76}$⊙CTV7 and $C_{78}$⊙CTV7 hemicarceplexes (188 mg) were dissolved in toluene (20 mL) and heated at 50° C. for 16 h. The toluene solution was removed via pipette after centrifugation. Another charge of toluene (5 mL) was added to wash the white solid and then the mixture was centrifuged again. The residue obtained after concentrating the combined toluene phases was suspended in CH$_2$Cl$_2$ (10 mL), in which the hemicarceplex mixtures are highly soluble, forming a black precipitate of fullerene mixtures, which were collected through centrifugation. The fullerene mixtures were then resuspended in CH$_2$Cl$_2$ (5 mL), centrifuged, separated from the solvent, and dried (43 mg).

Figure 26:
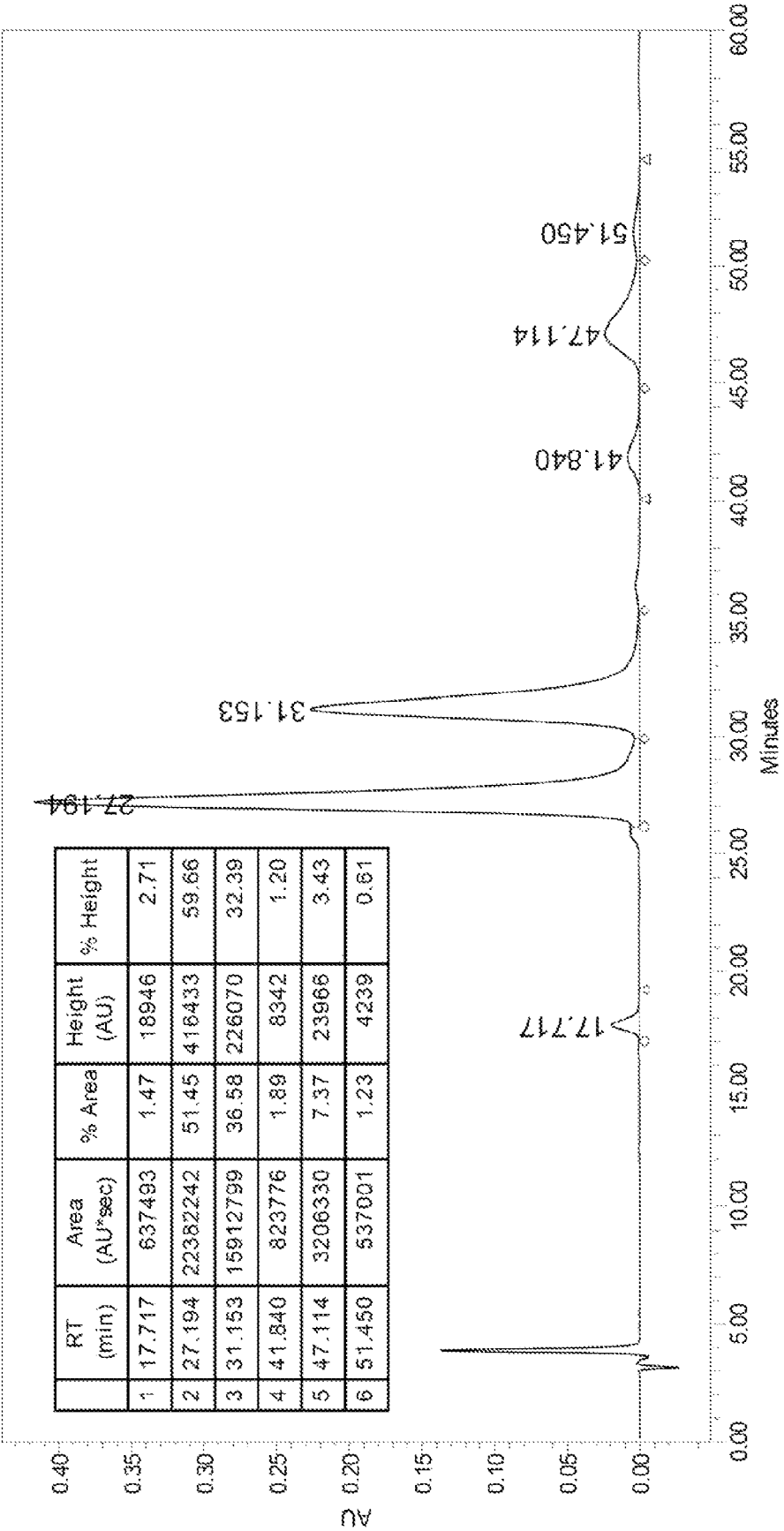
FIG. 26 is HPLC analysis results of the fullerene mixture released from C$_{76}$⊙CTV7 and C$_{78}$⊙CTV7 hemicarceplexes.

The purity was determined through HPLC analysis. The HPLC analysis results were shown in FIG. 26, which not only supported that the hemicarcerplexes do have $C_{76}$ and $C_{78}$ incarcerated but also suggested the formation of $C_{70}$⊙CTV7, $C_{82}\odot CTV7$, $C_{84}\odot CTV7$ and $C_{86}\odot CTV7$ as the minor products. The results indicated that selective isolation of $C_{76}$ and $C_{78}$ from high-order fullerene mixture may be achieved by using CTV7 as the entrapping host.

The Release of the Incarcerated $C_{84}$ from $C_{84}\odot CTV8$ Hemicarceplexes The $C_{84}\odot CTV8$ hemicarceplexes (122 mg) were dissolved in $CS_2$ (10 mL) at room temperature and stirred for 16 h. The $CS_2$ solution was removed via pipette after centrifugation. Another charge of $CS_2$ (5 mL) was added to wash the white solid and then the mixture was centrifuged again. The residue obtained after concentrating the combined toluene phases was suspended in $CH_2Cl_2$ (10 mL), in which the hemicarceplex mixtures are highly soluble, forming a black precipitate of fullerene mixtures, which were collected through centrifugation. The fullerene mixtures were then resuspended in $CH_2Cl_2$ (5 mL), centrifuged, separated from the solvent, and dried (30 mg).

Figure 27:
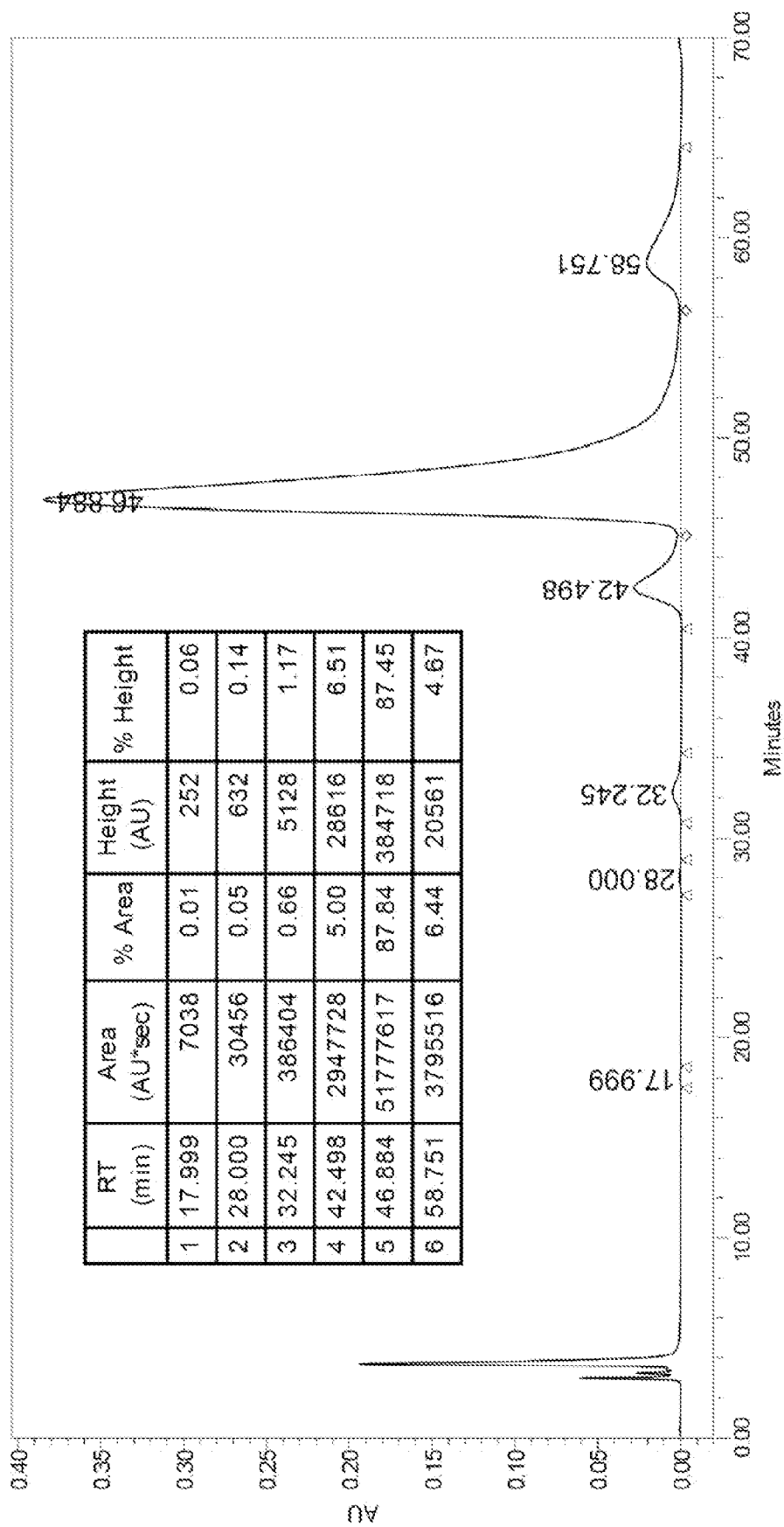
FIG. 27 is HPLC analysis results of the fullerene mixture released from C$_{84}$⊙CTV8 hemicarceplexes.

The purity was determined through HPLC analysis. The HPLC analysis results were shown in FIG. 27, which not only supported that the hemicarcerplexes do have $C_{84}$ incarcerated but also suggested the formation of $C_{70}\odot CTV8$, $C_{76}\odot CTV8$, $C_{78}\odot CTV8$, $C_{82}\odot CTV8$ and $C_{86}\odot CTV8$ as the minor products. The results indicated that selective isolation of $C_{84}$ from high-order fullerene mixture may be achieved by using CTV8 as the entrapping host.

Figure 28:
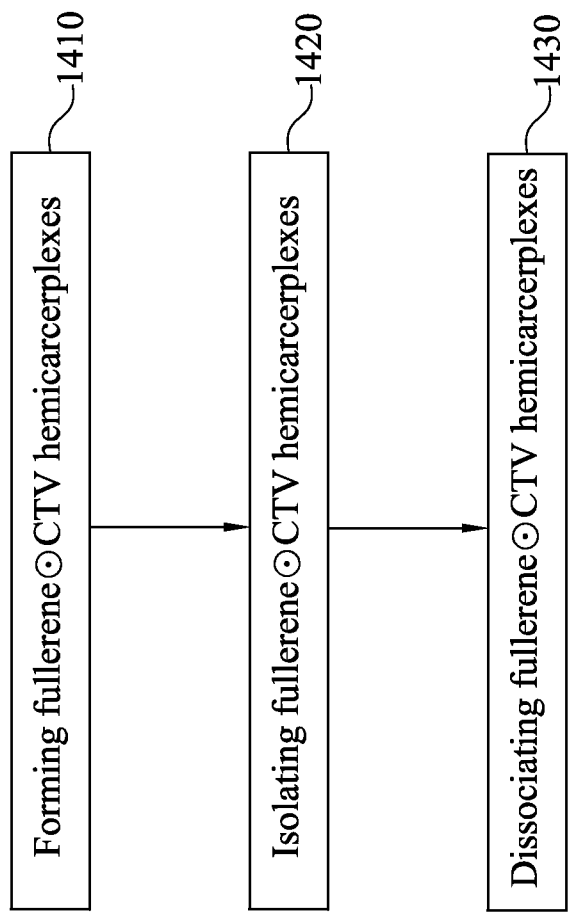
FIG. 28 is a process flow diagram of isolating fullerene⊙CTV hemicarceplexes by column chromatography.

Isolating Fullerenes from Fullerene Extracts by Using Fullerene CTV Hemicarceplexes Fullerenes or derivatives thereof may be isolated from their mixtures in high purity through the following steps: (1) selectively generating a fullerene⊙CTV hemicarceplex in solution, (2) isolating the fullerene⊙CTV hemicarceplexes by column chromatography, and (3) dissociating the fullerene⊙CTV hemicarceplexes to release the pure fullerenes. FIG. 28 is a process flow diagram of isolating fullerenes without using crystallization or HPLC.

In the step 1410 of FIG. 28, fullerene CTV hemicarceplexes has to be formed first. In step 1420, the fullerene CTV hemicarceplexes are then isolated by using column chromatography. In step 1430, the isolated fullerenes are obtained by dissociating the fullerene CTV hemicarceplexes. The related details of each step are described below.

In step 1410 of FIG. 28, fullerene CTV hemicarceplexes are formed by mixing a CTV host and a fullerene mixture, such as a fullerene extract, in a first solvent at a first temperature to form a first mixture solution. Then, the first mixture solution is concentrated under a reduced pressure to obtain a first solid residue.

The first solvent can dissolve both fullerenes and CTV host and do not have strong tendency to enter and compete with fullerenes in occupying the inner space of the CTV host. For example, the first solvent can majorly contain $CS_2$, $CH_2Cl_2$, $CHCl_3$ or $CHCl_2CHCl_2$ but is not limited thereto.

The formation of fullerene CTV hemicarceplexes may be inspected by either $^1H$ or $^{13}C$ NMR, such as those NMR spectra shown in FIGS. 13-17 discussed above. Accordingly, the lowest first temperature has to be sufficiently high to see that new NMR signals corresponding to the fullerene CTV hemicarceplexes appear within few hours. For example, the first temperature may be room temperature to 60° C., such as 40° C., but is not limited thereto.

Moreover, the needed reaction time can also be determined by either 1H or $^{13}C$ NMR. When the new NMR signals corresponding to the fullerene CTV hemicarceplexes grow to reach a maximum strength, the reaction may be stopped.

Next, a second solvent is added to the first solid residue to form a suspended solution. Then, the suspended solution is filtered to obtain filtrate of the suspended solution.

The CTV host and the fullerene CTV hemicarceplexes have better solubility in the second solvent than the free fullerenes. Therefore, most of the free fullerenes may be filtered off, and the filtrate contains the fullerene CTV hemicarceplexes. For example, the second solvent can majorly contain $CH_2Cl_2$, $CHCl_3$ or $CHCl_2CHCl_2$, but is not limited thereto.

In step 1420 of FIG. 28, the filtrate of the suspended solution in step 1410 is concentrated and then loaded onto a column of silica gel to prepare for a subsequent column chromatography. Then, a third solvent, a fourth solvent, and a fifth solvent were sequentially used to elute the free fullerenes, fullerene⊙CTV hemicarceplexes, and free CTV hosts from the column. Since the polarity of the free fullerenes, fullerene⊙CTV hemicarceplexes, and free CTV hosts are generally in an increasing order, the polarity of the third solvent, the fourth solvent, and the fifth solvents for eluting the molecules above are better also generally in an increasing order.

Accordingly, since the third solvent is used to remove any uncomplexed and/or dissociated fullerenes from the column, the third solvent has to be capable of dissolving free fullerenes. For examples, the third solvent can majorly contain $CS_2$, benzene, toluene or dichlorobenzene but is not limited thereto.

The fourth solvent is used to isolate the fullerene CTV hemicarceplexes from the column. Therefore, the fourth solvent has to be capable of dissolving the fullerene CTV hemicarceplexes. For example, the fourth solvent can majorly contains $CH_2Cl_2$ or $CHCl_3$, such as $CH_2Cl_2$ and hexane mixed in a volume ratio of 3:2, but is not limited thereto.

The fifth solvent is used to elute the free CTV host from the column, so that the free CTV host may be recover for the next use. Therefore, the fifth solvent has to be capable of dissolving the free CTV host. For example, the fifth solvent can majorly contains $CH_2Cl_2$ or $CHCl_3$, such as $CH_2Cl_2$ and MeOH mixed in a volume ratio of 49:1, but is not limited thereto.

In step 1430 of FIG. 28, the portion of the eluate containing the fullerene⊙CTV hemicarceplexes is concentrated, and a sixth solvent is then added to dissociate the fullerene CTV hemicarceplexes at a second temperature. In the best scenario, free fullerenes have good solubility in the sixth solvent, and the CTV host has a poor solubility in the sixth solvent. Therefore, the released fullerenes and fullerene CTV hemicarceplexes are still dissolved in the sixth solvent, but the free CTV host is precipitated as solid. Otherwise, the dissociated free fullerenes can still be separated from free cage and the hemicarceplexes by chromatographic methods. Accordingly, the sixth solvent can majorly contain $CS_2$, $CH_2Cl_2$, $CHCl_3$, $CHCl_2CHCl_2$, benzene, toluene, or dichlorobenzene, for example, but is not limited thereto.

Since the dissociation reaction is the reverse reaction the hemicarceplexe formation reaction, the dissociation reaction may also need heating. The lowest temperature for the second temperature also may be determined by NMR spectra when the NMR signals corresponding to the fullerene CTV hemicarceplexes decrease within few hours. For examples, the second temperature may be higher than room temperature, such as 30° C. to 80° C., but is not limited thereto.

Next, the solution of the sixth solvent was concentrated, and a seventh solvent is then added. For separating the released fullerenes and fullerene CTV hemicarceplexes, the released fullerenes have a poor solubility in the seventh solvent, and the fullerene CTV hemicarceplexes have a good solubility in the seventh solvent. Therefore, the seventh solvent can majorly contain $CH_2Cl_2$, or $CHCl_3$, for example, but is not limited thereto.

Since the seventh solvent has poor solubility for the free fullerenes, the free fullerenes are precipitated. Hence, a simple filtering step can obtain the free fullerenes.

Experiment 1

Using CTV1 to Isolate $C_{70}$ from Fullerene Extract: Small Scale (1) Forming $C_{70}\odot CTV1$ Hemicarceplex:

The CTV1 (50 mg) and the fullerene extract above (300 mg, purchased from SES Research) were dissolved in $CHCl_2CHCl_2$ (5 mL) and stirred at various temperatures for various periods of time for Examples 1-6. The organic solvent was removed under reduced pressure and the residue was dissolved in $CH_2Cl_2$ (40 mL). After filtration, the solvent was evaporated under reduced pressure to obtain various amounts of solid for Examples 1-6. The related data above were listed in Table 2 below.

TABLE 2

Related data of forming $C_{70}\odot CTV1$ hemicarceplex

| Examples | Stirring temp. (° C.) | Stirring time (h) | Solid amount (mg) |
|---|---|---|---|
| 1 | 40 | 16 | 86.4 |
| 2 | 40 | 16 | 101.1 |
| 3 | 40 | 16 | 111.2 |
| 4 | 50 | 16 | 72.8 |
| 5 | 40 | 40 | 91.4 |
| 6 | 40 | 16 | 98.4 |

(2) Using Column Chromatography to Isolate $C_{70}\odot CTV1$ Hemicarceplex:

The obtained solid above was purified through column chromatography (5 g of $SiO_2$). The eluents of $CS_2$, $CH_2Cl_2$/hexane (3:2 in volume ratio) and $CH_2Cl_2$/MeOH (49:1 in volume ratio) were sequentially used to sequentially elute free fullerenes, $C_{70}\odot CTV1$, and free CTV1 from the column. The eluate portions of the $CH_2Cl_2$/hexanes (3:2 in volume ratio) of Examples 1-6 were then respectively evaporated to obtain various amounts of $C_{70}\odot CTV1$. The using amounts of each eluent and the obtained amounts of $C_{70}\odot CTV1$ are all listed in Table 3 below.

TABLE 3

Related data of column chromatography

| | Eluents (mL) | | | |
|---|---|---|---|---|
| Examples | $CS_2$ | $CH_2Cl_2$/hexane (3:2) | $CH_2Cl_2$/MeOH (49:1) | $C_{70}\odot CTV1$ (mg) |
| 1 | 50 | 250 | 100 | 37.2 |
| 2 | 50 | 250 | 50 | 33.1 |
| 3 | 50 | 400 | 50 | 32.2 |
| 4 | 50 | 200 | 50 | 30.0 |
| 5 | 50 | 250 | 50 | 38.4 |
| 6 | 50 | 250 | 50 | 37.3 |

(3) Obtaining $C_{70}$ by Dissociating $C_{70}\odot CTV1$

The obtained $C_{70}\odot CTV1$ hemicarceplex was then dissolved in toluene (4 mL) and heated at a temperature for 12 h to dissociate the $C_{70}\odot CTV1$ hemicarceplex. The toluene solution was centrifuged to yield upper toluene solution and white precipitate. The upper toluene solution containing the free $C_{70}$ was removed via pipette. Another charge of toluene (5 mL) was added to wash the white solid of CTV1 to wash down the residue free $C_{70}$ from the white solid. Then, the two toluene solutions were mixed and centrifuged again to take the upper toluene solution. The white solid was recycled as the free CTV1.

The residue obtained after concentrating the combined toluene solutions was suspended in $CH_2Cl_2$ (5 mL) again to dissolve the highly soluble $C_{70}\odot CTV1$ hemicarceplex. However, the free $C_{70}$ formed red precipitate in the $CH_2Cl_2$. Therefore, the $C_{70}$ red precipitate in the $CH_2Cl_2$ was obtained by centrifuging the $CH_2Cl_2$ suspension and then drying, and the black $CH_2Cl_2$ solution was then dried to recycle $C_{70}\odot CTV1$ hemicarceplex.

The composition of the purchased fullerene extract and the purity of $C_{70}$ was determined through HPLC analysis (Cosmosil-packed 5PBB analytical column, 4.6×250 mm; mobile phase, toluene; UV detection, 285 nm; elution rate, 1 mL $min^{-1}$). Accordingly, the compositions of the purchased fullerene extract and the purity of $C_{70}$ were determined by dividing the integration value of the corresponding signal by the total integration values of the $C_{60}$, $C_{70}$, $C_{76}$, $C_{78}$, and $C_{84}$ signals.

Accordingly, the dissociation temperatures and the obtained amounts and purity of $C_{70}$ for Examples 1-6 were listed in Table 4, and the amounts of the recycled $C_{70}\odot CTV1$ hemicarceplex and recovered CTV1 for Examples 1-6 were listed in Table 5. The compositions of the purchased fullerene extract and the purified $C_{70}$ of Example 1 are listed in Table 6 below.

TABLE 4

Related data of dissociating $C_{70}\odot CTV1$ hemicarceplex

| Examples | Dissociation temp. (° C.) | Obtained $C_{70}$ (mg) | Purity of obtained $C_{70}$ (%) |
|---|---|---|---|
| 1 | 30 | 7.1 | 99.1 |
| 2 | 30 | 6.5 | 99.0 |
| 3 | 30 | 6.7 | 99.1 |
| 4 | 30 | 8.2 | 93.5 |
| 5 | 30 | 8.0 | 96.4 |
| 6 | 40 | 8.3 | 96.7 |

TABLE 5

Recovered amounts of the $C_{70}\odot CTV1$ hemicarceplex and CTV1

| Examples | $C_{70}\odot CTV1$ (mg) | CTV1 (mg) |
|---|---|---|
| 1 | 15.0 | 30.3 |
| 2 | 12.8 | 30.5 |
| 3 | 12.3 | 30.6 |
| 4 | — | 27.6 |
| 5 | — | 30.4 |
| 6 | — | 31.6 |

TABLE 6

Analyzing compositions of the purchased fullerene extract and the purified $C_{70}$ of Examples 1-6 by HPLC

| Examples | $C_{60}$ (%) | $C_{70}$ (%) | $C_{76}$ (%) | $C_{78}$ (%) | $C_{84}$ (%) |
|---|---|---|---|---|---|
| 1 | 0.03 | 99.1 | 0.83 | 0 | 0 |
| 2 | 0.14 | 99.0 | 0.88 | 0 | 0 |
| 3 | 0.03 | 99.1 | 0.90 | 0 | 0 |

TABLE 6-continued

Analyzing compositions of the purchased fullerene extract
and the purified $C_{70}$ of Examples 1-6 by HPLC

| Examples | $C_{60}$ (%) | $C_{70}$ (%) | $C_{76}$ (%) | $C_{78}$ (%) | $C_{84}$ (%) |
|---|---|---|---|---|---|
| 4 | 0.21 | 93.5 | 2.75 | 0.13 | 0 |
| 5 | 0.35 | 96.4 | 2.99 | 0.27 | 0 |
| 6 | 0.07 | 96.7 | 1.66 | 0.13 | 0 |
| Fullerene extract | 65.97 | 24.02 | 1.75 | 1.85 | 2.62 |

Experiment 2

Using CTV1 to Isolate $C_{70}$ from Fullerene Extract: Large Scale

After obtaining consistent results when repeating the isolation as shown above, the scale was increased to ten-fold of the previous small scale experiments.

The CTV1 (500 mg) and the fullerene extract (3.0 g) were dissolved in $CHCl_2CHCl_2$ (50 mL) and stirred at 40° C. for 16 h. The organic solvent was removed under reduced pressure and the residue was dissolved in $CH_2Cl_2$ (250 mL). After filtration, the solvent was evaporated under reduced pressure to afford a solid (950 mg), which was purified through column chromatography [$SiO_2$ (25 g); eluent: $CS_2$ (250 mL) followed by $CH_2Cl_2$/hexane, 3:2 (1550 mL), and $CH_2Cl_2$/MeOH, 49:1 (600 mL)].

The hemicarceplex (366.1 mg) obtained was then dissolved in toluene (20 mL) and heated at 30° C. for 12 h. The toluene solution was removed via pipette after centrifugation. Another charge of toluene (20 mL×2) was added to wash the white solid and then the mixture was centrifuged again. The white solid was recycled as the free CTV1. The residue obtained after concentrating the combined toluene phases was suspended in $CH_2Cl_2$ (20 mL), in which the hemicarceplex C70⊙CTV1 is highly soluble, to form a red precipitate of $C_{70}$, which was collected through centrifugation. The solid $C_{70}$ was then resuspended in $CH_2Cl_2$ (20 mL×2), centrifuged, separated from the solvent, and dried (72.6 mg). The purity of $C_{70}$, determined through HPLC analysis, was 99.0%. The black $CH_2Cl_2$ solution was then concentrated to recycle 96.4 mg of the hemicarceplex C70⊙CTV1. The total amount of recovered CTV1 was 360 mg (72% recovery).

The recycled hemicarceplex (96.4 mg) was redissolved in toluene (10 mL) and heated at 30° C. for 12 h. The suspension was centrifuged to afford the CTV1 as a white precipitate. The organic solution was removed via pipette and concentrated to give a black solid, which was dissolved in $CH_2Cl_2$ (10 mL) and centrifuged. The solid $C_{70}$ was then resuspended in $CH_2Cl_2$ (10 mL×2), centrifuged, separated from the solvent, and dried (6.6 mg). The purity of the $C_{70}$, determined through HPLC analysis, was 92.6%. The black $CH_2Cl_2$ solution was concentrated to obtain 78.6 mg of the recycled hemicarceplex C70⊙CTV1. The amount of recycled CTV1 was 13.8 mg (26% recovery).

Accordingly, the compositions of the large-scale purified $C_{70}$ obtained in the first round and second round of isolation process and the purchased fullerene extract are listed in Table 7 below. The percentages of each component were determined by the HPLC method mentioned in the small scale experiment above.

TABLE 7

Analyzing the compositions of the large-scale purified C70 obtained
in the first round and second round of isolation process by HPLC

| composition | $C_{60}$ (%) | $C_{70}$ (%) | $C_{76}$ (%) | $C_{78}$ (%) | $C_{84}$ (%) |
|---|---|---|---|---|---|
| First round | 0.03 | 99.0 | 0.90 | 0.10 | 0 |
| Second round | 0.05 | 92.6 | 6.00 | 0.65 | 0 |
| Fullerene extract | 65.97 | 24.02 | 1.75 | 1.85 | 2.62 |

Accordingly, the isolated $C_{70}$ in the first round isolation process was not only in approximately 10 times the amount (72.6 mg) of the previous small scale experiments, but also in similar purity (99.0%) to the previous small scale experiments. Thus, the amount of $C_{70}$ isolated in a single purification cycle should be scalable to even greater levels if a greater amount of CTV1 is applied.

In this large-scale experiment, the total amount of the CTV1 that we recovered after chromatography and precipitation from toluene was 360 mg (72% recovery). Concentrating the $CH_2Cl_2$ phase obtained after dissociation of the hemicarceplex under reduced pressure allowed recycling of 96 mg of the hemicarceplex $C_{70}$⊙CTV1 (26% recovery, containing 64 mg of CTV1). Therefore, the mass loss of the CTV1 throughout the whole isolation process was approximately 15%. Because the dissociation of the hemicarceplex did not require competing guests, the recycled CTV1 could be used directly in a subsequent isolation cycle without the need for any specific treatment or purification process.

In the second round of isolation process, dissociation of the recycled hemicarceplex under similar conditions afforded $C_{70}$ in 92.6% purity (HPLC analysis). Notably, based on HPLC analysis, the $C_{70}$ isolated using this method was only negligibly contaminated with $C_{60}$ (0.05%); its major impurities were $C_{76}$ (6.00%) and $C_{78}$ (0.65%). Therefore, the CTV1 appears to also isolate $C_{76}$ and $C_{78}$ from the fullerene extract. Based on HPLC analysis of the commercial fullerene extract that we tested in this study, the ratio of $C_{76}$, $C_{78}$, and $C_{84}$ was approximately 1:1.1:1.6 (i.e., $C_{76}$ was a relatively minor component). Therefore, our CTV1 appears to be capable of kinetically differentiating these three buckyballs through the effective formation of the hemicarceplex $C_{76}$⊙CTV1 under the developed experimental conditions.

Experiment 3

Using CTV1 to Obtain a Mixture of $C_{70}$, $C_{76}$ and $C_{78}$ from High Fullerene Extract The CTV1 (50 mg) and the high fullerene extract (50 mg; purchased from MER Corp.) were mixed in $CHCl_2CHCl_2$ (5 mL) and stirred at 40° C. for 18 h. The organic solvent was evaporated under reduced pressure and the residue was dissolved in $CH_2Cl_2$ (20 mL). After filtration, the solvent was evaporated under reduced pressure to afford a solid, which was purified through column chromatography [$SiO_2$ (8 g); eluent: $CS_2$ (50 mL) followed by $CH_2Cl_2$/hexane, 3:2 (400 mL), and $CH_2Cl_2$/MeOH, 49:1 (100 mL)].

The hemicarceplex mixtures (32.0 mg) were obtained and the above experiment was repeated three times and collected hemicarceplex mixture (105 mg) was then dissolved in toluene (5 mL) and heated at 30° C. for 6 h. The toluene solution was removed via pipette after centrifugation. Another charge of toluene (5 mL) was added to wash the white solid and then the mixture was centrifuged again. The white solid was recycled as the free CTV1.

The residue obtained after concentrating the combined toluene phases was suspended in $CH_2Cl_2$ (5 mL), in which the hemicarceplex mixtures are highly soluble, forming a red precipitate of fullerene mixtures, which were collected through centrifugation. The fullerene mixtures were then resuspended in $CH_2Cl_2$ (5 mL), centrifuged, separated from the solvent, and dried (4.8 mg). The purity was determined through HPLC analysis. The HPLC analysis results were listed in Table 8 below. From the HPLC result, it may be known that the mixture of $C_{70}$, $C_{76}$ and $C_{78}$ may be isolated from the mixture of the high fullerene extract.

TABLE 8

Analyzing the compositions of the purchased high fullerene extract and the purity of the obtained black solid fullerene mixtures by HPLC

| composition | $C_{60}$ (%) | $C_{70}$ (%) | $C_{76}$ (%) | $C_{78}$ (%) | $C_{84}$ (%) |
|---|---|---|---|---|---|
| High fullerene extract | 4.2 | 6.8 | 12.9 | 14.0 | 65.8 |
| Obtained fullerene mixtures | 0 | 7.2 | 52.5 | 40.3 | 0 |

Experiment 4

Using CTV5 to Obtain Mixture of $C_{76}$ and $C_{78}$ from Mixture of $C_{70}$, $C_{76}$ and $C_{78}$ The CTV5 (1.5 mg) and the fullerene mixture [0.75 mg; the one contains only $C_{70}$, $C_{76}$ and $C_{78}$ obtained from the Experiment 3] were mixed in $CHCl_2CHCl_2$ (0.4 mL) at 27° C. for 21 h. The organic solvent was evaporated under reduced pressure to afford a solid, which was purified through column chromatography [$SiO_2$ (0.4 g); eluent: $CS_2$ (2 mL) followed by EA/hexane, 3:7 in volume ratio (10 mL)]. The hemicarceplex mixture was then dissolved in toluene (0.8 mL) and heated at 50° C. for 40 h. The toluene solution was analyzed by HPLC. The HPLC analysis results were listed in Table 9 below. From the HPLC analysis result, it may be known that the mixture of $C_{76}$ and $C_{78}$ may be isolated from the mixture of $C_{70}$, $C_{76}$ and $C_{78}$.

TABLE 9

HPLC analysis result

| composition | $C_{70}$ (%) | $C_{76}$ (%) | $C_{78}$ (%) |
|---|---|---|---|
| Initial fullerene mixture | 7.2 | 52.5 | 40.3 |
| Isolated fullerene mixture | 3.9 | 44.8 | 51.3 |

In light of the foregoing, various CTV hosts can form complexes or hemicarceplexes with various fullerenes. The hemicarceplexes of fullerene⊙CTV may be used to isolate a fullerene or a fullerene mixture within a certain steric size range from a fullerene mixture, without using HPLC or recrystallization techniques. The most remarkable is that CTV1 may be used to isolate $C_{70}$ in high purity (≥99.0%) from a commercial fullerene extract.

The preparation of hemicarcerands that isolate $C_{70}$ and higher fullerenes suggests the possibility of not only isolating and stabilizing these novel molecules, their analogues, and derivatives but also applying them practically as useful photovoltaic materials by significantly increasing their solubility in less-polar solvents without covalently disrupting their unique pi-surfaces. Moreover, by elongating or shortening the linking spacers of the CTV hosts, selective trapping of fullerenes with various sizes and the possibility of using them as photovoltaic materials are allowed.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. A fullerene⊙CTV complex formed by trapping a fullerene guest or a derivative thereof (abbreviated as a guest molecule below) in a cyclotriveratrylene-based molecular cage (abbreviated as CTV below) having a chemical structure below:

CTV

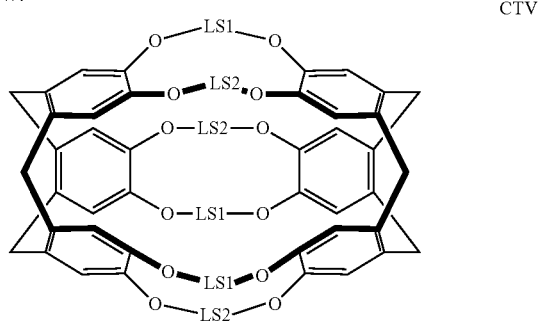

wherein LS1 and LS2 are first and second linking spacers respectively, wherein the cyclotriveratrylene-based molecular cage is CTV1
(LS1 = LS2 = —(CH₂)₁₂—), CTV2
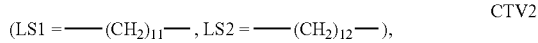
(LS1 = —(CH₂)₁₁—, LS2 = —(CH₂)₁₂—), CTV3
(LS1 = —(CH₂)₁₀—, LS2 = —(CH₂)₁₂—), CTV4
(LS1 = —(CH₂)₁₂—,
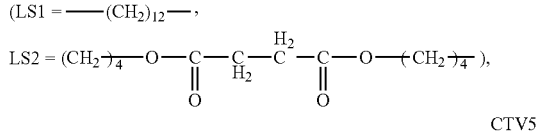
LS2 = (CH₂)₄—O—C(=O)—CH₂—C(H₂)—CH₂—C(=O)—O—(CH₂)₄—), CTV5
(LS1 = —(CH₂)₁₁—,
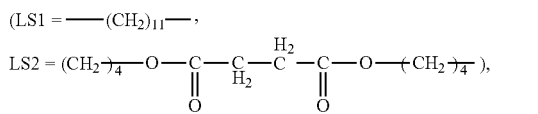
LS2 = (CH₂)₄—O—C(=O)—CH₂—C(H₂)—CH₂—C(=O)—O—(CH₂)₄—), CTV6
(LS1 = —(CH₂)₁₀—,
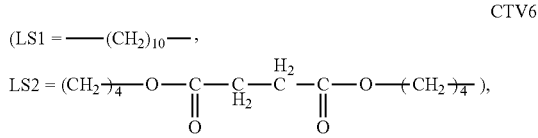
LS2 = (CH₂)₄—O—C(=O)—CH₂—C(H₂)—CH₂—C(=O)—O—(CH₂)₄—), CTV7
(LS1 = (CH₂)₁₂, LS2 = (CH₂)₁₃), CTV8
(LS1 = (CH₂)₁₂, LS2 = (CH₂)₁₄), CTV9
(LS1 = (CH₂)₁₂, LS2 = (CH₂)₁₅), CTV10
(LS1 = (CH₂)₁₃, LS2 = (CH₂)₁₄), CTV11
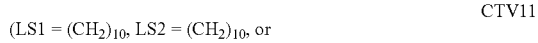
(LS1 = (CH₂)₁₀, LS2 = (CH₂)₁₀, or CTV12
(LS1 = (CH₂)₁₀, LS2 = (CH₂)₁₁).

2. The complex of claim 1, wherein the complex is $C_{60}\odot CTV1$, $C_{70}\odot CTV1$, $C_{76}\odot CTV1$, $C_{78}\odot CTV1$, $C_{60}\odot CTV2$, $C_{70}\odot CTV2$, $C_{60}\odot CTV3$, $Sc_3N@C_{80}\odot CTV4$, $C_{60}\odot CTV5$, $C_{70}\odot CTV5$, $C_{76}\odot CTV5$ or $C_{78}\odot CTV5$, $C_{60}\odot CTV6$, $C_{70}\odot CTV7$, $C_{76}\odot CTV7$, $C_{78}\odot CTV7$, $C_{82}CTV7$, $C_{84}\odot CTV7$, $C_{86}\odot CTV7$, $C_{70}\odot CTV8$, $C_{76}\odot CTV8$, $C_{78}\odot CTV8$, $C_{82}\odot CTV8$, $C_{84}\odot CTV8$, $C_{86}\odot CTV8$, $C_{70}\odot CTV9$, $C_{60}\odot CTV11$, or $C_{60}\odot CTV12$.

* * * * *